US008008283B2

(12) United States Patent
Hochman et al.

(10) Patent No.: US 8,008,283 B2
(45) Date of Patent: Aug. 30, 2011

(54) METHODS AND COMPOSITIONS FOR THE TREATMENT OF NEUROPSYCHIATRIC DISORDERS

(75) Inventors: Daryl W. Hochman, Bahama, NC (US); John J. Partridge, Chapel Hill, NC (US)

(73) Assignee: Neurotherapeutics Pharma, Inc., Chicago, IL (US)

( * ) Notice: Subject to any disclaimer, the term of this patent is extended or adjusted under 35 U.S.C. 154(b) by 1045 days.

(21) Appl. No.: 11/251,724

(22) Filed: Oct. 17, 2005

(65) Prior Publication Data
US 2006/0089350 A1    Apr. 27, 2006

(51) Int. Cl.
C07C 303/00    (2006.01)
C07C 307/00    (2006.01)
C07C 309/00    (2006.01)
C07C 311/00    (2006.01)

(52) U.S. Cl. .......................................... 514/183; 564/84

(58) Field of Classification Search .................. 514/183; 564/84
See application file for complete search history.

(56) References Cited

U.S. PATENT DOCUMENTS

| | | |
|---|---|---|
| 3,058,882 A | 10/1962 | Sturm et al. |
| 3,634,583 A | 1/1972 | Feit |
| 3,665,002 A | 5/1972 | Popelak |
| 3,676,454 A | 7/1972 | Vida |
| 3,806,354 A | 4/1974 | Feit |
| 3,806,534 A | 4/1974 | Feit |
| 3,971,819 A | 7/1976 | Feit |
| 3,985,777 A | 10/1976 | Feit |
| 3,991,097 A | 11/1976 | Bormann et al. |
| 4,005,201 A | 1/1977 | Yurugi et al. |
| 4,010,273 A | 3/1977 | Bormann |
| 4,018,929 A | 4/1977 | Delarge |
| 4,154,652 A | 5/1979 | Sawamura et al. |
| 4,247,550 A * | 1/1981 | Feit et al. ................. 514/211.15 |
| 4,261,985 A | 4/1981 | Biollaz |
| 4,309,348 A | 1/1982 | Asselin et al. |
| 4,340,737 A | 7/1982 | Johnson |
| 4,351,833 A | 9/1982 | Johnson |
| 4,663,348 A | 5/1987 | Chafetz et al. |
| 4,895,807 A | 1/1990 | Cherksey |
| 4,973,600 A | 11/1990 | Takamura et al. |
| 5,034,109 A | 7/1991 | Fujibayashi et al. |
| 5,073,641 A | 12/1991 | Bundgaard et al. |
| 5,128,327 A | 7/1992 | Chakravarty et al. |
| 5,162,325 A | 11/1992 | Chakravarty et al. |
| 5,201,318 A | 4/1993 | Rava et al. |
| 5,256,687 A | 10/1993 | Becker et al. |
| 5,318,024 A | 6/1994 | Kittrell et al. |
| 5,475,008 A | 12/1995 | Carling et al. |
| 5,486,530 A | 1/1996 | Boelke et al. |
| 5,498,519 A | 3/1996 | Rubin et al. |
| 5,571,842 A | 11/1996 | Kleemann et al. |
| 5,585,401 A | 12/1996 | Brandt et al. |
| 5,627,077 A | 5/1997 | Dyllick-Brenzinger et al. |
| 5,654,335 A | 8/1997 | Schoenwald et al. |
| 5,658,786 A | 8/1997 | Smith et al. |
| 5,660,181 A | 8/1997 | Ho et al. |
| 5,753,651 A | 5/1998 | DePadova |
| 5,763,491 A | 6/1998 | Brandt et al. |
| 5,834,466 A | 11/1998 | Ramasamy et al. |
| 5,902,732 A | 5/1999 | Hochman |
| 5,976,825 A | 11/1999 | Hochman |
| 6,040,331 A | 3/2000 | Yamamoto et al. |
| 6,130,234 A | 10/2000 | Bigge et al. |
| 6,228,873 B1 | 5/2001 | Brandt et al. |
| 6,369,094 B1 | 4/2002 | Bentley et al. |
| 6,395,781 B1 | 5/2002 | Roman et al. |
| 6,420,405 B2 | 7/2002 | Inada et al. |
| 6,432,986 B2 | 8/2002 | Levin |
| 6,495,601 B1 | 12/2002 | Hochman |
| 6,669,951 B2 | 12/2003 | Rothbard et al. |
| 6,894,030 B2 | 5/2005 | Hartley |
| 7,199,139 B2 | 4/2007 | Takaoka et al. |
| 7,282,519 B2 | 10/2007 | Garvey et al. |
| 2002/0082252 A1 | 6/2002 | Hochman |
| 2002/0147197 A1 | 10/2002 | Newman et al. |
| 2005/0065086 A1 | 3/2005 | Kirk et al. |
| 2005/0203169 A1 | 9/2005 | Moskowitz |
| 2005/0234107 A1 | 10/2005 | Wank |
| 2005/0267103 A1 | 12/2005 | Hochman |
| 2006/0035914 A1 | 2/2006 | Hochman |
| 2006/0089350 A1 | 4/2006 | Hochman et al. |
| 2006/0111397 A1 | 5/2006 | Moskowitz |
| 2007/0043034 A1 | 2/2007 | Staley et al. |
| 2007/0092510 A1 | 4/2007 | De Koninck et al. |
| 2007/0155729 A1 | 7/2007 | Morgan et al. |
| 2007/0293463 A1 | 12/2007 | Dittrich et al. |

FOREIGN PATENT DOCUMENTS

| | | |
|---|---|---|
| DE | 2517183 A1 | 4/1975 |
| GB | 2207129 | 1/1999 |
| WO | WO 00/37616 | 6/2000 |
| WO | WO 00/37616 A1 | 6/2000 |
| WO | WO 03/013434 A2 | 2/2003 |
| WO | WO 2005/082350 | 9/2005 |
| WO | WO 2006/058008 A1 | 6/2006 |
| WO | WO 2006/110187 | 10/2006 |
| WO | WO 2006/110187 A2 | 10/2006 |
| WO | WO 2007/042504 A2 | 4/2007 |
| WO | WO 2008/052190 | 5/2008 |

OTHER PUBLICATIONS

Dorwald F. A. (Side reactions in organic synthesis, 2005, Wiley, VCH, Weinheim, p. IX of Preface).*

(Continued)

Primary Examiner — Marcos L Sznaidman
(74) Attorney, Agent, or Firm — Hunton & Williams LLP

(57) ABSTRACT

The present invention relates to methods and compositions for treating neuropathic pain and neuropsychiatric disorders by administering agents that are effective in reducing the effective amount, inactivating, and/or inhibiting the activity of a $Na^+$—$K^+$-$2Cl^-$ (NKCC) cotransporter. In certain embodiments, the $Na^+$—$K^+$-$2Cl^-$ co-transporter is NKCC1.

5 Claims, 12 Drawing Sheets

OTHER PUBLICATIONS

Bundgaard, Hans et al., "Photodegradation and Hydrolysis of Furosemide and Furosemide Esters in Azueous Solutions," *International Journal of Pharmaceutics*, vol. 42, pp. 217-224 (1988).

Bundgaard, Hans et al., "Glycolamide Esters as a Novel Biolabile Prodrug Type for Non-Steroidal Anti-Inflammatory Carboxylic Acid Drugs," *International Journal of Pharmaceutics*, vol. 43, pp. 101-110 (1988).

Granados-Soto, Vinicio et al., "Peripheral and Central Antinociceptive Action of $Na^+$ -$K^+$ -$2Cl^-$ Cotransporter Blockers on Formalin-Induced Nociception in Rats," *Pain*, vol. 114, pp. 231-238 (2005).

Hannaert, P. et al., "Rat NKCC2/NKCC1 Cotransporter Selectivity for Loop Diuretic Drugs," *Naunyn-Schmiedeberg's Arch. Pharmacol.*, vol. 365, pp. 193-199 (2002).

Haglund, Michael M. et al., "Furosemide and Mannitol Suppression of Epileptic Activity in the Human Brain," *J. Neurophysiol.*, vol. 94, pp. 907-918 (2005).

Mork, Niels et al., "Furosemide Prodrugs: Synthesis, Enzymatic Hydrolysis and Solubility of Various Furosemide Esters," *International Journal of Pharmaceutics*, vol. 60, pp. 163-169 (1990).

Prandi, C. et al., "Development of Absorption Furosemide Prodrugs: Synthesis, In Vitro and In Vivo Evaluation," *Il Farmaco*, vol. 42, No. 2, pp. 249-263 (1992).

Prandi, Carolina et al., "Bioavailability Study of Furosemide Prodrugs in Rats," *Il Farmaco*, vol. 47, No. 9, pp. 1225-1230 (1992).

"Burinex® K," intekom.com, Malahyde Information Systems (1996-2004).

"Strategies for Optimizing Migraine Management," *Proceedings From A CME Teleconference Series*, 1-26 (especially p. 8, para. 5) (2001).

"The Migraineur's Guide to Migraine," http://www.headachecare.com (2000).

Ahmad et al., "Controlled Trial of Furosemide As An Antiepileptic Drug In Focal Epilepsy" *Br. J. Clin Pharmac.* 3: 621-625 (1976).

Akerman, S., Goadsby, P. J., "Topiramate inhibits cortical spreading depression in rat and cat: impact in migraine aura," *Neuroreport* 16(12): 1383-7 (Abstract) (2005).

Barbaro, N. M. et al., "A Potential Role for Astrocytes in Mediating the Antiepileptic Actions of Furosemide In Vitro," *Neuroscience* 128: 655-663 (2004).

Batham et al., "Diazepam in Combination with Antiepileptic Drugs—An Experimental Study," *Indian J. Med. Res.* 66: 872-875 (1977).

Bazil, Carl W. et al., "Advances in the Medical Treatment of Epilepsy," *Annu. Rev. Med.* 49: 135-162 (1998).

Bikson, M. et al., "Inhibition of Nonsynaptic Epileptiform Activity in the Hippocampus," *Society for Neuroscience* 24: 1213 (Abstract) (1998).

Carter, C. H., "Status Epilepticus Treated by Intravenous Urea," *Epilepsia* 3: 198-200 (1962).

Collins, M. A. et al., "Brian damage due to episodic alcohol exposure in vivo and in vitro: furosemide neuroprotection implicates edema-based mechanism," *FASEB J.* 12: 221-230 (1998).

Cragoe, E. J., Jr., et al., "Agents for the treatment of brain injury. 1. (Aryloxy)alkanoic acids," *J. Med. Chem.* 25(5): 567-579 (May 1982).

Diener, H. C. et al., "Emerging Treatments in Headache," *European Neurology* 38(3): 167-174 (Abstract) (1997).

Dzhala et al., "NKCC1 Transporter Facilitates Seizures in the Developing Brain," *Nature Medicine* 11(11): 1205-1213 (2005).

Ebersberger, Andrea et al., "Is There a Correlation Between Spreading Depression, Neurogenic Inflammation, and Nociception That Might Cause Migraine Headache?" *Ann. Neurol.* 49(1): 7-13 (Jan. 2001).

Ellory, J. C.; Stewart, G. W. "The Human Erythrocyte Cl-Dependent Na-K Cotransport System as a Possible Model for Studying the Action of Loop Diuretics," *Br. J. Pharmac.* 75(1): 183-188 (1982).

Espinosa, X. Jimenez "Efecto Anticonvulsivante Del Seguril" *Tomo 61*(361): 280-282 (1969).

Ettmayer et al., "Lessons Learned from Marketed and Investigational Prodrugs" *J. Med. Chem.* 47(10): 2394-2404 (2004).

Feit, P. W., "Aminobenzoic Acid Diuretics. 2. 4-Substituted-3-amino-5-sulfamylbenzoic Acid Derivatives," *Journal of Med. Chem.* 14(5): 432-439 (1971).

Feit, P. W. et al., "Purification of Proteins of the Na/Cl Cotransporter from Membranes of Ehrlich Ascites Cells Using a Bumetanide-Sepharose Affinity Column," *J. Membrane Biol.* 103: 135-147 (1988).

Figure "azosemide" *Merck Index 13*: 924 (2001); U.S. Appl. No. 11/549,274, p. 25.

Figure "bumetanide" *Merck Index 13*: 1471 (2001); U.S. Appl. No. 11/549,274, p. 25.

Figure "furosemide" *Merck Index 13*: 4330 (2001); U.S. Appl. No. 11/549,274, p. 25.

Figure "piretanide" *Merck Index 13*: 7575 (2001); U.S. Appl. No. 11/549,274, p. 25.

Figure "toresemide" *Merck Index 13*: 9629; U.S. Appl. No. 11/549,274, p. 26.

Gamba et al., "Primary structure and functional expression of a cDNA encoding the thiazide-sensitive, electroneutral sodium-chloride cotransporter," *Proc. Natl. Acad. Sci. USA 90*: 2749-2753 (Apr. 1993).

González et al., "Acetyloxymethyl 4-chloro-N-furfuryl-5-sulfamoylanthranilate, an Absorption f urosemide Prodrug" *Acta Crystallographica, Section C C52*(11): 2875-2878 (1996); *Chem. Abstracts 126*: 25037 (1996).

Gutschmidt et al., "Anticonvulsant Actions of Furosemide in Vitro," *Neuroscience* 91(4): 1471-1481 (1999).

Haglund, Michael M. et al., "Enhanced Optical Imaging of Human Gliomas and Tumor Margins," *Neurosurgery* 38(2): 308-317 (Feb. 1996).

Haglund, Michael M. et al., "Enhanced Optical Imaging of Rat Gliomas and Tumor Margins," *Neurosurgery* 35(5): 930-941 (Nov. 1994).

Haglund, Michael M. et al., "Optical Imaging of Epileptiform and Functional Activity in Human Cerebral Cortex," *Nature* 358: 668-671 (1992).

Hesdorfer, Dale C. et al., "Are Certain Diuretics Also Anticonvulsants?" *Ann. Neurol.* 50(4): 458-462 (Oct. 2001).

Hesdorfer, Dale C. et al., "Severe, Uncontrolled Hypertension and Adult-Onset Seizures: A Case-Control Study in Rochester, Minnesota," *Epilepsia* 37(8): 736-741.

Hochman, D. W. et al., "Dissociation of Synchronization and Excitability of Furosemide Blockade of Epileptiform Activity," *Science* 270: 99-102 (Oct. 1995).

Hochman, D. W.; Schwartzkroin, P. A., "Extracellular Chloride and the Maintenance of Epileptiform Activity in Hippocampal Slices," *Society for Neuroscience* 23 (Part 2): 2425 (1997).

Hochman, Daryl W. et al., "Extracellular Chloride and the Maintenance of Spontaneous Epileptiform Activity in Rat Hippocampal Slices," *J. Neurophysiol.* 81: 49-59 (1999).

Hochman, Daryl W., "Intrinsic Optical Changes in Neuronal Tissue," *Neurosurgery Clinics of North America* 8(3): 393-412 (Jul. 1997).

Hochman, Daryl W.; Schwartzkroin, Philip A. "Chloride-Cotransport Blockade Desynchronizes Neuronal Discharge in the 'Epileptic' Hippocampal Slice," *J. Neurophysiol.* 83: 406-417 (2000).

Inoue, M. et al., "Intracerebroventricular injections of ethacrynic acid induces status epilepticus," *Eur. J. Pharmacol.* 166(1): 101-106 (and Abstract—*BIOSIS*) (1989).

James, M. F. et al., "Cortical spreading depression and migraine: new insights from imaging?" *Trends Neurosci.* 24(5): 266-271 (Abstract) (May 2001).

Jauch et al., "Effects of Barium, Furosemide, Ouabaine and 4,4'-Diisothiocyanatostilbene-2,2'-disulfonic acid (DIDS) on Ionophoretically-Induced Changes in Extracellular Potassium Concentration in Hippocampal Slices from Rats and from Patients with Epilepsy," *Brain Research* 925: 18-27 (2002).

Jefferys, John G. R., "Mechanisms and Experimental Models of Seizure Generation," *Current Opinion in Neurology* 11: 123-127 and 174-180 (1998).

Jin et al., "Impaired $Cl^-$ extrusion in Layer V Pyramidal Neurons of Chronically Injured Epileptogenic Neocortex," *J. Neurophysiol* 93: 2117-2126 (2005).

Johnson, Bankole A. et al., "Oral topiramate for treatment of alcohol dependence: a randomised controlled trial," *Lancet* 361: 1677-1685 (2003).

Kempski, O. et al., "Glial ion transport and volume control," *Ann. N.Y. Acad. Sci.* 633: 306-317 (Abstract) (1991).

Kimelberg, H. K., "Anisotonic media and glutamate-induced ion transport and volume responses in primary astrocyte cultures," *J. Physiol.* (Paris) 82(4): 294-303 (Abstract) (1987).

Kimelberg, H. K.; Frangakis, M. V. "Furosemide- and bumetanide-sensitive ion transport and volume control in primary astrocyte cultures from rat brain," *Brain Res.* 361(1-2): 125-134 (Abstract) (Dec. 1985).

Lambert et al., "Cortical spreading depression reduces dural blood flow a possible mechanism for migraine pain," *Cephalalgia* 14(6): 430-436 (see also Abstract and discussion 393-394) (1994).

Lowenstein, Daniel H. et al., "Status Epilepticus," *The New England Journal of Medicine* 338(14): 970-976 (1998).

MacDonald, Robert L. et al., "Mechanisms of Action of New Antiepileptic Drugs," *Current Opinion in Neurology* 10: 121-128 (1997).

Margineanu et al., "Differential Effects of Cation-Chloride Co-Transport-Blocking Diuretics in a Rat Hippocampal Slice Model of Epilepsy," *Epilepsy Research* 69: 93-99 (2006).

Masereel et al., "Anticonvulsant Activity of Pyrid-3-yl-Sulfonyl Ureas and Thioreas," *Epilepsia* 38(3): 334-337 (1997).

Mathew, N. T. et al., "Coexistence of migraine and idiopathic intracranial hypertension without papilledema," *Neurology* 46: 1226-1230 (May 1996).

McElroy, Susan L. et al., "Topiramate in the Treatment of Binge Eating Disorder.Associated with Obesity: A Randomized, Placebo-Controlled Trial," *Am. J. Psychiatry* 160(2): 255-261 (Feb. 2003).

McLeod, M.S., "The Mysterious Etiology of Head Pain," *Medical Sciences Bulletin* (1996).

Merkel, Wulf et al., "Selektive Reduktion von Imiden mit funktionellen Gruppen," *Liebigs Ann. Chem.* 4: 461-469 (1979).

Misiuk, N. S. et al., "Effect of glycerol, mannitol and lasix on cerebrospinal fluid pressure in the acute period of a stroke," Abstract—*Medline* (1981).

Misiuk, N. S. et al., *Zhurnal Nevropatologii I Psikhiatrii Imeni S. S. Korsakova* 81(8): 1149-1152 (1981).

Mombru et al., "Two Absorption Furosemide Prodrugs" *Acta Crystallographics, Section C* C55(3): 413-416 (1999); *Chem. Abstracts* 130: 289414 (1999).

Muraki et al., "Aminoaluminum Hydride as New Reducing Agents. I. Selective Reduction of Carboxylic Acids to Aldehydes" *Chemistry Letters*, 1447-1450 (1974) and *CHEM Letters* 215-218 (1975).

Ngohou-Bonevat et al., "Treatment of Convulsive Ecalmpsia Crisis by Therapeutic Combination; Diazepam, Dihydralazine, Furosemide," *Bulletin De La Federation Des Societes De Gynecologie et a D Obstertrique De Langue Francaise* (Dec. 1971).

Noble et al., *Org. Synth., Coll.* Vol. IV, John Wiley & Sons, Inc., pp. 924-927 (1963).

Obrenovitch, T. P., Zilkha, E., "Inhibition of cortical spreading depression by L-701, 324, a novel antagonist at the glycine site of the N-methyl-D-aspartate receptor complex," *British Journal of Pharmacology* 117(5): 931-937 (Mar. 1997).

Parsons, A. A., "Cortical Spreading Depression: Its Role in Migraine Pathogenesis and Possible Therapeutic Intervention Strategies," *Current Pain and Headache Reports* 8: 410-416 (2004).

Parsons, A. A., "Recent advances in mechanisms of spreading depression," *Current Opinion in Neurology* 11: 227-231 (1998).

Pasantes-Morales et al., "Volumn-sensitive release of taurine from cultured astrocytes: properties and mechanism," *Glia* 3(5): 427-432 (Abstract) (1990).

Petzinger, E. et al., "Interaction of bumetanide derivatives with hepatocellular bile acid uptake," *Am. J. Physiol.* 265(5): G942-G954 (1993).

Pinegin, L. E. et al., "Effect of furosemide on intracranial pressure in patients with intracranial hypertension," Abstract—*Medline* (1983).

Pinegin, L. E. et al., *Zhurnal Nevropatologii I Psikhiatrii Imeni S. S. Korsakova* 83(5): 675-677 (1983).

Prandi et al., "A Bioavailability Study of Furosemide Prodrug in Humans" *Acta Farmaceutica Bonaerense* 12(3): 131-136 (1993); *Chem. Abstracts* 122: 89212 (1995).

Prandi et al., "Studies on the Relation Between Structure-Lipophilicity-Hydrolysis Kinetics of a Combination of Albumin with a Series of Furosemide Prodrugs" *Revista Portuguesa de Farmacia* 44(4):164-169 (1994); *Chem. Abstracts* 123: 47371 (1995).

Read et al., *Cephalgia* 17: 826 (1997).

Read, S. J. et al., "Furosemide inhibits regenerative cortical spreading depression in anaesthetized cats," *Abstract—BIOSIS* (Dec. 1997).

Reed, Donal J. et al., "The Effect of Hypertonic Urea Solution on Electroshock Seizure Threshold and Electrolyte Distribution in Rats," *Reed and Woodbury* 146: 154-159 (1964).

Reid et al., "Agents which Block Potassium-Chloride Contransport Prevent Sound-Triggered Seizures in Post-Ischemic Audiogenic Seizure-Prone Rats," *Brain Research* 864: 134-137 (2000).

Rivera, C. et al., "The $K^+/Cl^-$ Co-Transporter KCC2 Renders GABA Hyperpolarizing During Neuronal Maturation," *Nature* 397(6716): 251-255 (Abstract) (1999).

Rozen, T. D., "Treatment of a Prolonged Migrainous Aura with Intravenous Furosemide," *Neurology* 55: 732-733 (Sep. 2000).

Sato et al., "Effect of Acetazolamide on the Antioconvulsant Potency of Phenobarbital in Mice," *J. Pharm. Dyn.* 4: 952-960 (1981).

Schlatter, E. et al., "Effect of "High Ceiling" Diuretics on Active Salt Transport in the Cortical Thick Ascending Limb of Henle's Loop of Rabbit Kidney: Correlation of Chemical Structure and Inhibitory Potency," *Pflüger Arch.* 396: 210-217 (1983).

Schwartzkroin, Philip A. et al., "Osmolarity, Ionic Flux, and Changes in Brain Excitability," *Epilepsy Research* 32: 275-285 (1998).

SciFinder search on "Furosemide" 1-96 (2006).

Shani, J. et al., "Structure Activity Correlation for Diuretic Furosemide Congeners," *Pharmacology* 26(3): 172-180 (Mar. 1983).

Shirai et al., "Acetazolamide Testing of Cerebral Vasodilator Capacity Provokes "Vascular" But Not Tension Headaches," *The Journal of Head and Face Pain* 36(10): 589 (Abstract) (1996).

Sinha, S. R.; Saggau, P., "Effects of Furosemide on Normal and Epileptiform Evoked Activity in Area CA1 of Guinea Pig Hippocampal Slice," *Society for Neuroscience* 23(Part 2): 2425 (1997).

Snow, R. W. et al., "Electrophysiological and Optical Changes in Slices of Rat Hippocampus During Spreading Depression," *Journal of Neurophysiology* 50(3): 561-572 (1983).

Stringer et al., "Effect of Seizures and Diuretics on the Osmolality of the Cerebrospinal Fluid," *Brain Research* 745: 328-330 (1997).

Sturm et al., "Synthesen von 5-Sulfamoyl-anthranilsaure-Derivaten," *Chem. Ber.*, Weinheim, v. 99: 328-344 (1966).

Suescun et al., "Three Isostructural Furosemide Prodrugs" *Acta Crystallographica, Section C* C54(12): 1911-1915; *Chem. Abstracts* 130: 117642 (1999).

Thevis et al., "Effect of the Location of Hydrogen Abstraction on the Fragmentation of Diuretics in Negative Electrospray Ionization Mass Spectrometry," *J. Am. Soc. for Mass Spectrom.* 14: 658-670 (2003).

Tongia S. K., "Frusemide Suppressing Audiogenic Seizure," *Ind. J. Physiol. Pharmac.—Letter to the Editor* 91-92 (1981).

Tongia S. K., "Potentiated Anticonvulsant Effect Against Audiogenic Seizure with Frusemide and Diphenylhydantoin Sodium," *Ind. J. Physiol. Pharmac.—Letter to the Editor* 25(3): 292-294 (1981).

Upton, Neil, "Mechanisms of Action of New Antiepileptic Drugs: Rational Design and Serendipitous Findings," *TiPS* 15: 456-463 (1994).

Walz, W. et al., "Intense Furosemide-Sensitive Potassium Accumulation in Astrocytes in the Presence of Pathologically High Extracellular Potassium Levels," *J. Cerebral Blood Flow and Metabolism* 4: 301-304 (1984).

Walz, W., "Role of astrocytes in the spreading depression signal between ischemic core and penumbra," *Neurosci. Biobehav. Rev.* 21(2): 135-142 (Abstract) (1997).

Walz, W., "Role of Na/K/Cl cotransport in astrocytes," *Can. J. Physiol. Pharmacol.* 70 (Suppl.): S260-S262 (Abstract) (1992).

Welch, K. M. A., "Cortical Hyperexcitability Seen As Mechanism for Migraine With Aura," *Reuters Health Information Bulletin* (Jun. 20, 1997).

Welch, K. M. A., "Current opinions in headache pathogenesis: introduction and synthesis," *Current Opinion in Neurology 11*: 193-197 (1998).
Welch, K. M. A., "Pathogenesis of Migraine," *Seminars in Neurology 17*(4): 335-341 (1997).
Welch, K. M. et al., "The Concept of Migraine as a State of Central Neuronal Hyperexcitability," *Neural Clin. 8*: 817-828 (Abstract) (1990).
Welch, M., "Brain Imaging Studies Support Neuroelectric Etiology of Migraine Aura," *Reuters Health Information*, 2 pages (Abstract) (May 10, 1999).
Worthley, L. I. G., Thomas, P. D., "Treatment of Hyponatraemic Seizures with Intravenous 29.2% Saline," *Br. Med. J. 292*: 168-170 (Jan. 1986).
European Journal of Pharmacology 344: 269-277 (1998).
European Journal of Medicinal Chemistry (1976), 11(5), 399-406.
Ellory, et al., "The Human Erythrocyte Cl-Dependent Na-K Cotransport System as a Possible Model for Studying the Action of Loop Diretics", British Journal Pharmacology, vol. 75, pp. 183-188, (1982).
Feit, et al., Purification of Proteins of the Na/Cl Cotransporter from Membranes of Ehrlich Ascites Cells Using a Bumetanide-Sepharose Affinity Column, Journal of Membrane Biology, vol. 103, pp. 135-147, (1988).
Hochman, et al., "Chloride-Cotransport Blockade Desynchronizes Neuronal Discharge in the 'Epileptic' Hippocampal Slices", The American Physiological Society, pp. 406-417, (2000).
Hochman, et al., "Extracellular Chloride and the Maintenance of Spontaneous Epileptiform Activity in Rat Hippocampal Slices", The American Physiological Society, pp. 49-59, (1999).
Merkel, et al., "Selektive Reduktion von Imiden mit Funktionellen Gruppen", Liebigs Ann. Chem., pp. 461-469, (1979).
Mork, et al., "Furosemide Prodrugs: Synthesis, Enzymatic Hydrolysis and Solubility of Various Furosemide Esters", International Journal of Pharmaceutics—Elsevier, pp. 163-169, (1990).
Petzinger, et al. Interaction of Bumetanide Derivatives with Hepatocellular Bile Acid Uptake, American Journal of Physiology, vol. 265, No. 5, pp. G942-G954, (1993).
Schlatter, et al., "Effect of 'High Ceiling' Diuretics on Active Salt Transport in the Cortical Thick Ascending Limb of Henle's Loop of Rabbit Kidney", Pflugers Archiv., vol. 369, pp. 210-217, (1983).
Shani, J., et al., Structure Activity Correlation for Diuretic Furosemide Congeners, Pharmacology 26: p. 172-180 (1983).
International Search Report for International Application No. PCT/US2006/040108 mailed May 9, 2007.
International Preliminary Report on Patentability International Application No. PCT/US2006/040108 mailed Oct. 17, 2005.
Written Opinion of the International Searching Authority International Application No. PCT/US2006/040108 mailed Oct. 17, 2005.
Database Biosis [Online] Biosciences Information Service, Philadelphia, PA, US; 2003, Valencia DE ITA S et al: "The Role Of The Na+ -K+ -2Cl-Cotransporter in the Development Of Capsaicin-Induced Neurogenic Inflammation." XP002523057.
Delpire, E. et al., "Human and Murine Phenotypes Associated with Defects in Cation-Chloride Cotransport", Annual Review of Physiology 2002 US, vol. 64, pp. 803-843, XP002523054.
Granados-Soto, V. et al., "Peripheral and Central Antinocieptive Action of $N^+$-$K^+$-$2Cl^-$ Cotransporter Blockers on Formalin-Induced Nociception in Rats", Pain Elsevier Science publishers, Amsterdam, NL, vol. 114, No. 1-2, Mar. 2005.
Haglund, M. et al., "Furosemide and Mannitol Supperssion of Epileptic Activity in the Human Brain", Journal of NeuroPhysiology 200508 US, vol. 94, No. 2, XP002523053, pp. 907-918, Aug. 2005.
Laird, J. et al., "Presynaptic Inhibition and Spinal Pain Processing in Cition-Chloride Co-Transporter in Hyperalgesia", Neuroscience Letters 20040506 IE, vol. 361, No. 13, pp. 200-203.
Sung, K W et al: "Abnormal GABAA receptor-mediated currents in dorsal root ganglion neurons isolated from Na-K-2Cl cotransporter null mice." The Journal of Neuroscience : The Official Journal of the Society for Neuroscience Oct. 15, 2000, vol. 20, No. 20, Oct. 15, 2000, pp. 7531-7538, XP002523056.
Extended European Search Report for International Application No. PCT/US2005/043177, mailed Jun. 4, 2009.

* cited by examiner

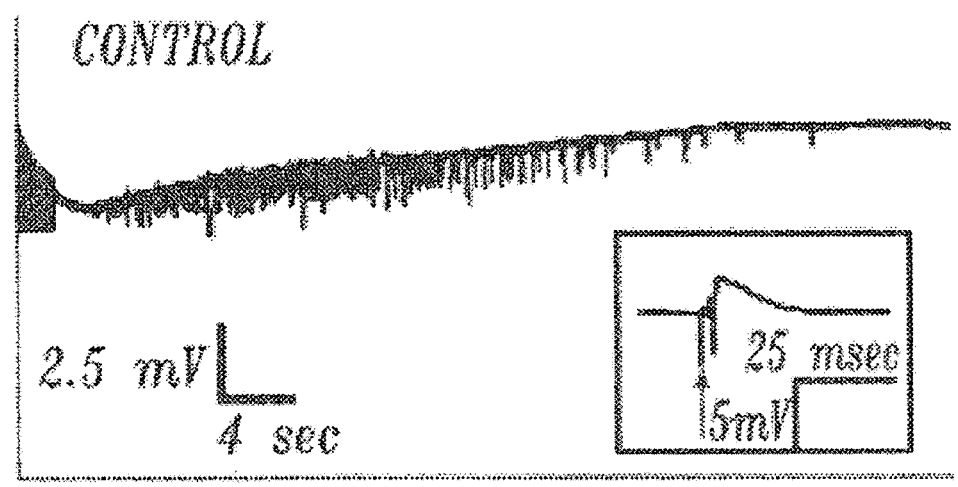
Fig. 1A
Fig. 1A1

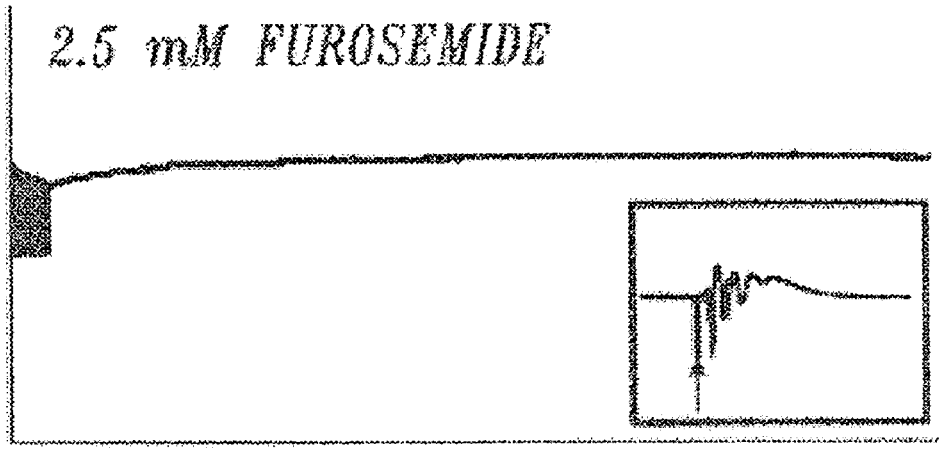
Fig. 1B
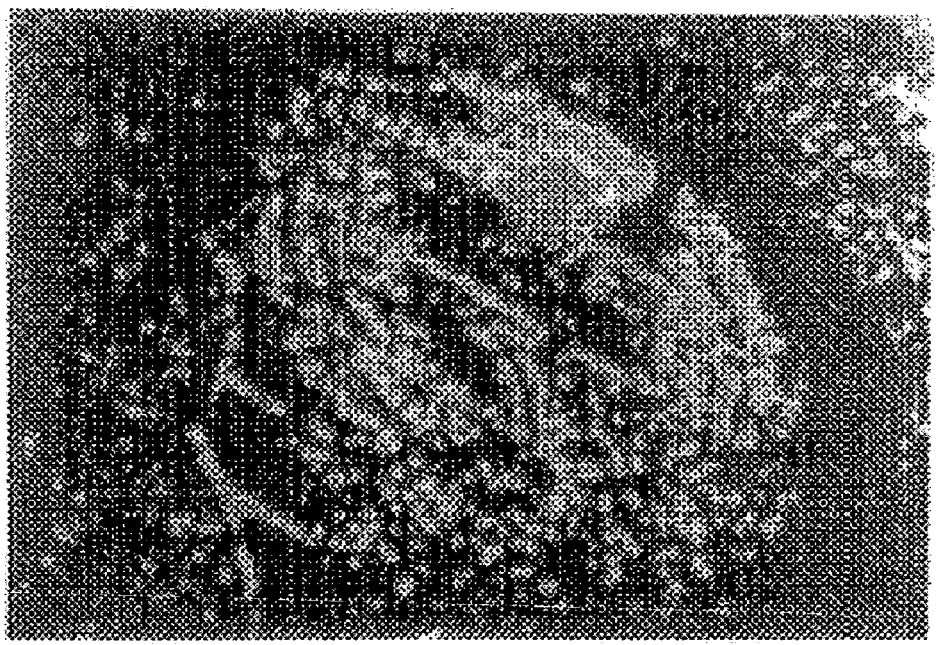
Fig. 1B1

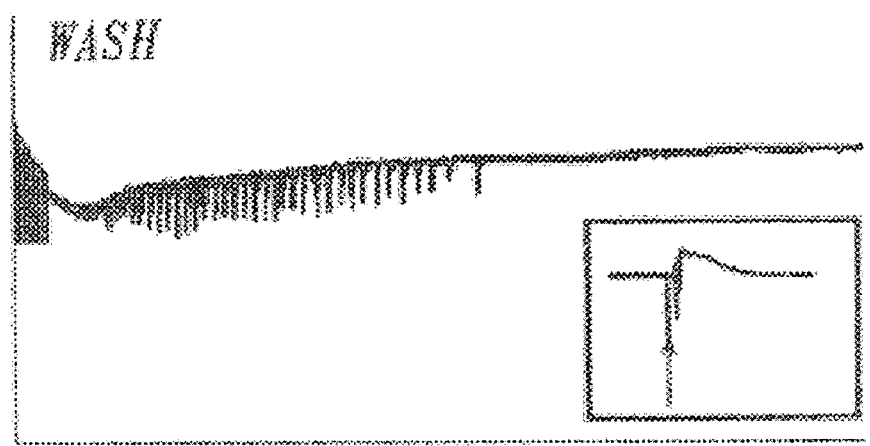
Fig. 1C
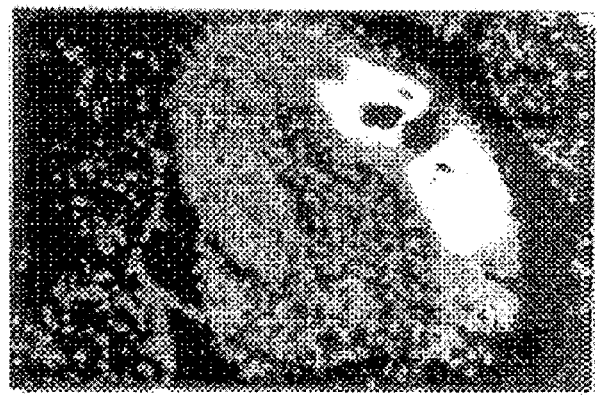
Fig. 1C1
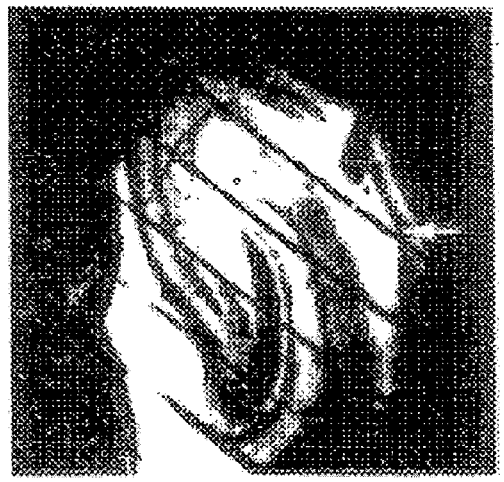
Fig. 1D 1 s / 5 mV 1 s / 5 mV

Fig. 2K
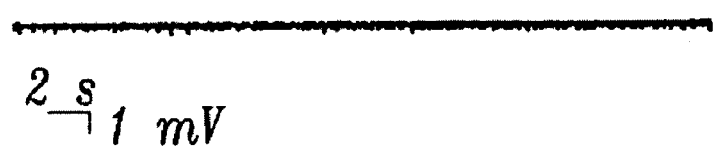
Fig. 2L
Fig. 2M
Fig. 2N
Fig. 2O
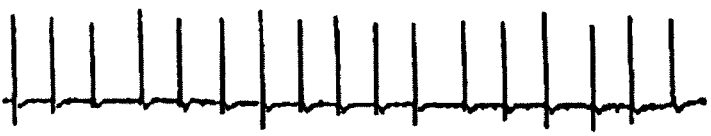
Fig. 2P
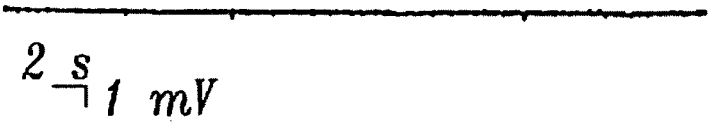
Fig. 2Q
Fig. 2R

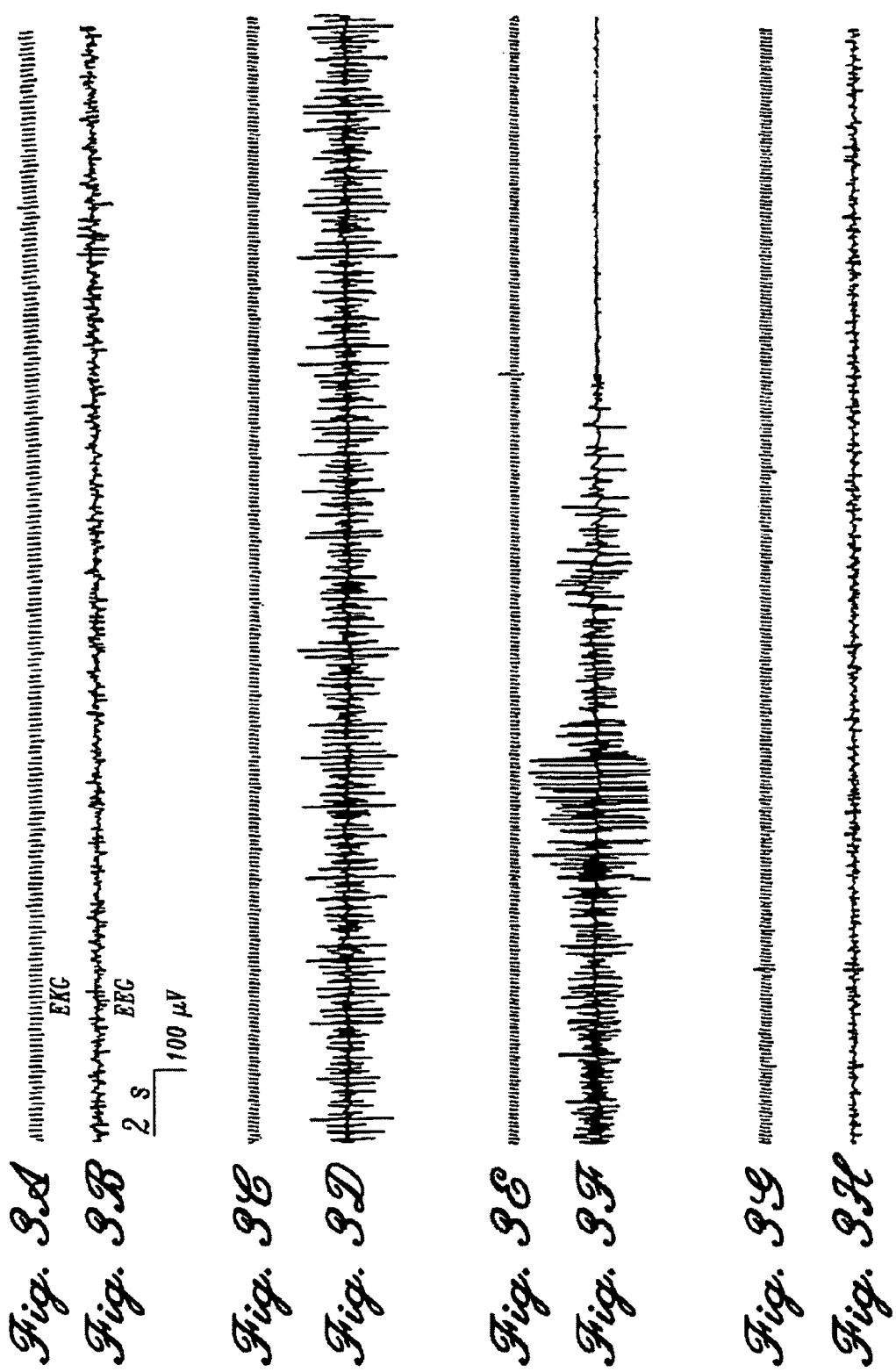

SEQUENCE LISTING

<160> NUMBER OF SEQ ID NOS: 2

<210> SEQ ID NO 1
<211> LENGTH: 1212
<212> TYPE: PRT
<213> ORGANISM: Human

<400> SEQUENCE: 1

```
Met Glu Pro Arg Pro Thr Ala Pro Ser Ser Gly Ala Pro Gly Leu Ala
 1               5                   10                  15

Gly Val Gly Glu Thr Pro Ser Ala Ala Ala Leu Ala Ala Ala Arg Val
            20                  25                  30

Glu Leu Pro Gly Thr Ala Val Pro Ser Val Pro Glu Asp Ala Ala Pro
        35                  40                  45

Ala Ser Arg Asp Gly Gly Gly Val Arg Asp Glu Gly Pro Ala Ala Ala
    50                  55                  60

Gly Asp Gly Leu Gly Arg Pro Leu Gly Pro Thr Pro Ser Gln Ser Arg
65                  70                  75                  80

Phe Gln Val Asp Leu Val Ser Glu Asn Ala Gly Arg Ala Ala Ala Ala
                85                  90                  95

Ala Ala Ala Ala Ala Ala Ala Ala Ala Ala Gly Ala Gly Ala Gly
            100                 105                 110

Ala Lys Gln Thr Pro Ala Asp Gly Glu Ala Ser Gly Glu Ser Glu Pro
        115                 120                 125

Ala Lys Gly Ser Glu Glu Ala Lys Gly Arg Phe Arg Val Asn Phe Val
    130                 135                 140

Asp Pro Ala Ala Ser Ser Ser Ala Glu Asp Ser Leu Ser Asp Ala Ala
145                 150                 155                 160

Gly Val Gly Val Asp Gly Pro Asn Val Ser Phe Gln Asn Gly Gly Asp
                165                 170                 175

Thr Val Leu Ser Glu Gly Ser Ser Leu His Ser Gly Gly Gly Gly
            180                 185                 190

Ser Gly His His Gln His Tyr Tyr Tyr Asp Thr His Thr Asn Thr Tyr
        195                 200                 205

Tyr Leu Arg Thr Phe Gly His Asn Thr Met Asp Ala Val Pro Arg Ile
    210                 215                 220

Asp His Tyr Arg His Thr Ala Ala Gln Leu Gly Glu Lys Leu Leu Arg
```

-continued

```
                225                 230                 235                 240
Pro Ser Leu Ala Glu Leu His Asp Glu Leu Glu Lys Glu Pro Phe Glu
                    245                 250                 255
Asp Gly Phe Ala Asn Gly Glu Glu Ser Thr Pro Thr Arg Asp Ala Val
                260                 265                 270
Val Thr Tyr Thr Ala Glu Ser Lys Gly Val Lys Phe Gly Trp Ile
            275                 280                 285
Lys Gly Val Leu Val Arg Cys Met Leu Asn Ile Trp Gly Val Met Leu
        290                 295                 300
Phe Ile Arg Leu Ser Trp Ile Val Gly Gln Ala Gly Ile Gly Leu Ser
305                 310                 315                 320
Val Leu Val Ile Met Met Ala Thr Val Val Thr Ile Thr Gly Leu
                    325                 330                 335
Ser Thr Ser Ala Ile Ala Thr Asn Gly Phe Val Arg Gly Gly Gly Ala
                340                 345                 350
Tyr Tyr Leu Ile Ser Arg Ser Leu Gly Pro Glu Phe Gly Gly Ala Ile
            355                 360                 365
Gly Leu Ile Phe Ala Phe Ala Asn Ala Val Ala Val Ala Met Tyr Val
        370                 375                 380
Val Gly Phe Ala Glu Thr Val Val Glu Leu Leu Lys Glu His Ser Ile
385                 390                 395                 400
Leu Met Ile Asp Glu Ile Asn Asp Ile Arg Ile Ile Gly Ala Ile Thr
                    405                 410                 415
Val Val Ile Leu Leu Gly Ile Ser Val Ala Gly Met Glu Trp Glu Ala
                420                 425                 430
Lys Ala Gln Ile Val Leu Leu Val Ile Leu Leu Ala Ile Gly Asp
            435                 440                 445
Phe Val Ile Gly Thr Phe Ile Pro Leu Glu Ser Lys Lys Pro Lys Gly
        450                 455                 460
Phe Phe Gly Tyr Lys Ser Glu Ile Phe Asn Glu Asn Phe Gly Pro Asp
465                 470                 475                 480
Phe Arg Glu Glu Glu Thr Phe Phe Ser Val Phe Ala Ile Phe Phe Pro
                    485                 490                 495
Ala Ala Thr Gly Ile Leu Ala Gly Ala Asn Ile Ser Gly Asp Leu Ala
                500                 505                 510
Asp Pro Gln Ser Ala Ile Pro Lys Gly Thr Leu Leu Ala Ile Leu Ile
            515                 520                 525
Thr Thr Leu Val Tyr Val Gly Ile Ala Val Ser Val Gly Ser Cys Val
        530                 535                 540
Val Arg Asp Ala Thr Gly Asn Val Asn Asp Thr Ile Val Thr Glu Leu
545                 550                 555                 560
Thr Asn Cys Thr Ser Ala Ala Cys Lys Leu Asn Phe Asp Phe Ser Ser
                    565                 570                 575
Cys Glu Ser Ser Pro Cys Ser Tyr Gly Leu Met Asn Asn Phe Gln Val
                580                 585                 590
Met Ser Met Val Ser Gly Phe Thr Pro Leu Ile Ser Ala Gly Ile Phe
            595                 600                 605
Ser Ala Thr Leu Ser Ser Ala Leu Ala Ser Leu Val Ser Ala Pro Lys
        610                 615                 620
Ile Phe Gln Ala Leu Cys Lys Asp Asn Ile Tyr Pro Ala Phe Gln Met
625                 630                 635                 640
Phe Ala Lys Gly Tyr Gly Lys Asn Asn Glu Pro Leu Arg Gly Tyr Ile
                    645                 650                 655
```

-continued

```
Leu Thr Phe Leu Ile Ala Leu Gly Phe Ile Leu Ile Ala Glu Leu Asn
            660                 665                 670

Val Ile Ala Pro Ile Ile Ser Asn Phe Leu Ala Ser Tyr Ala Leu
        675                 680                 685

Ile Asn Phe Ser Val Phe His Ala Ser Leu Ala Lys Ser Pro Gly Trp
    690                 695                 700

Arg Pro Ala Phe Lys Tyr Tyr Asn Met Trp Ile Ser Leu Leu Gly Ala
705                 710                 715                 720

Ile Leu Cys Cys Ile Val Met Phe Val Ile Asn Trp Trp Ala Ala Leu
                725                 730                 735

Leu Thr Tyr Val Ile Val Leu Gly Leu Tyr Ile Tyr Val Thr Tyr Lys
            740                 745                 750

Lys Pro Asp Val Asn Trp Gly Ser Ser Thr Gln Ala Leu Thr Tyr Leu
        755                 760                 765

Asn Ala Leu Gln His Ser Ile Arg Leu Ser Gly Val Glu Asp His Val
    770                 775                 780

Lys Asn Phe Arg Pro Gln Cys Leu Val Met Thr Gly Ala Pro Asn Ser
785                 790                 795                 800

Arg Pro Ala Leu Leu His Leu Val His Asp Phe Thr Lys Asn Val Gly
                805                 810                 815

Leu Met Ile Cys Gly His Val His Met Gly Pro Arg Arg Gln Ala Met
            820                 825                 830

Lys Glu Met Ser Ile Asp Gln Ala Lys Tyr Gln Arg Trp Leu Ile Lys
        835                 840                 845

Asn Lys Met Lys Ala Phe Tyr Ala Pro Val His Ala Asp Asp Leu Arg
    850                 855                 860

Glu Gly Ala Gln Tyr Leu Met Gln Ala Ala Gly Leu Gly Arg Met Lys
865                 870                 875                 880

Pro Asn Thr Leu Val Leu Gly Phe Lys Lys Asp Trp Leu Gln Ala Asp
                885                 890                 895

Met Arg Asp Val Asp Met Tyr Ile Asn Leu Phe His Asp Ala Phe Asp
            900                 905                 910

Ile Gln Tyr Gly Val Val Val Ile Arg Leu Lys Glu Gly Leu Asp Ile
        915                 920                 925

Ser His Leu Gln Gly Gln Glu Glu Leu Leu Ser Ser Gln Gly Lys Ser
    930                 935                 940

Pro Gly Thr Lys Asp Val Val Ser Val Glu Tyr Ser Lys Lys Ser
945                 950                 955                 960

Asp Leu Asp Thr Ser Lys Pro Leu Ser Glu Lys Pro Ile Thr His Lys
                965                 970                 975

Val Glu Glu Glu Asp Gly Lys Thr Ala Thr Gln Pro Leu Leu Lys Lys
            980                 985                 990

Glu Ser Lys Gly Pro Ile Val Pro Leu Asn Val Ala Asp Gln Lys Leu
        995                 1000                1005

Leu Glu Ala Ser Thr Gln Phe Gln Lys Lys Gln Gly Lys Asn Thr Ile
    1010                1015                1020

Asp Val Trp Trp Leu Phe Asp Asp Gly Gly Leu Thr Leu Leu Ile Pro
1025                1030                1035                1040

Tyr Leu Leu Thr Thr Lys Lys Lys Trp Lys Asp Cys Lys Ile Arg Val
                1045                1050                1055

Phe Ile Gly Gly Lys Ile Asn Arg Ile Asp His Asp Arg Arg Ala Met
            1060                1065                1070

Ala Thr Leu Leu Ser Lys Phe Arg Ile Asp Phe Ser Asp Ile Met Val
        1075                1080                1085
```

```
Leu Gly Asp Ile Asn Thr Lys Pro Lys Lys Glu Asn Ile Ile Ala Phe
    1090                1095                1100
Glu Glu Ile Ile Glu Pro Tyr Arg Leu His Gly Asp Lys Glu Gln
1105                1110                1115                1120
Asp Ile Ala Asp Lys Met Lys Glu Asp Glu Pro Trp Arg Ile Thr Asp
            1125                1130                1135
Asn Glu Leu Glu Leu Tyr Lys Thr Lys Thr Tyr Arg Gln Ile Arg Leu
        1140                1145                1150
Asn Glu Leu Leu Lys Glu His Ser Ser Thr Ala Asn Ile Ile Val Met
    1155                1160                1165
Ser Leu Pro Val Ala Arg Lys Gly Ala Val Ser Ser Ala Leu Tyr Met
    1170                1175                1180
Ala Trp Leu Glu Ala Leu Ser Lys Asp Leu Pro Pro Ile Leu Leu Val
1185                1190                1195                1200
Arg Gly Asn His Gln Ser Val Leu Thr Phe Tyr Ser
            1205                1210

<210> SEQ ID NO 2
<211> LENGTH: 6891
<212> TYPE: DNA
<213> ORGANISM: Human

<400> SEQUENCE: 2
ggtggcctct gtggccgtcc aggctagcgg cggcccgcag gcggcgggga gaaagactct      60
ctcacctggt cttgcggctg tggccaccgc cggccagggg tgtggagggc gtgctgccgg     120
agacgtccgc cgggctctgc agttccgccg ggggtcgggc agctatggag ccgcggccca     180
cggcgccctc ctccgcgccc ccgggactgg ccggggtcgg ggagacgccg tcagccgctg     240
cgctggccgc agccagggtg gaactgcccg gcacggctgt gccctcggtg ccggaggatg     300
ctgcgcccgc gagccgggac ggcggcgggg tccgcgatga gggccccgcg gcggccgggg     360
acgggctggg cagacccttg ggcccacccc gagccagag ccgtttccag gtggacctgg      420
tttccgagaa cgccgggcgg gccgctgctg cggcggcggc ggcggcggcg gcagcggcgg     480
cggctggtgc tggggcgggg gccaagcaga cccccgcgga cggggaagcc agcggcgaga     540
gcgagccggc taaaggcagc gaggaagcca agggccgctt ccgcgtgaac ttcgtggacc     600
cagctgcctc ctcgtcggct gaagacagcc tgtcagatgc tgccggggtc ggagtcgacg     660
ggcccaacgt gagcttccag aacgcggggg acacggtgct gagcgagggc agcagcctgc     720
actccggcgg cggcggcggc agtgggcacc accagcacta ctattatgat acccacacca     780
acacctacta cctgcgcacc ttcggccaca caccatggat cgctgtgccc aggatcgatc     840
actaccggca cacagccgcg cagctgggcg agaagctgct ccggcctagc ctggcggagc     900
tccacgacga gctggaaaag gaaccttttg aggatggctt tgcaaatggg aagaaagta      960 ctccaaccag agatgctgtg gtcacgtata ctgcagaaag taaggagtc gtgaagtttg     1020 gctggatcaa gggtgtatta gtacgttgta tgttaaacat ttggggtgtg atgcttttca    1080
ttagattgtc atggattgtg ggtcaagctg aataggtct atcagtcctt gtaataatga     1140
tggccactgt tgtgacaact atcacaggat tgtctacttc agcaatagca actaatggat    1200
ttgtaagagg aggaggagca tattatttaa tatctagaag tctagggcca gaatttggtg    1260
gtgcaattgg tctaatcttc gcctttgcca acgctgttgc agttgctatg tatgtggttg    1320
gatttgcaga aaccgtggtg gagttgctta aggaacattc catacttatg atagatgaaa    1380
tcaatgatat ccgaattatt ggagccatta cagtcgtgat tcttttaggt atctcagtag    1440
```

```
ctggaatgga gtgggaagca aaagctcaga ttgttctttt ggtgatccta cttcttgcta   1500
ttggtgattt cgtcatagga acatttatcc cactggagag caagaagcca aaagggtttt   1560
ttggttataa atctgaaata tttaatgaga actttgggcc cgattttcga gaggaagaga   1620
cttctttttc tgtatttgcc atcttttttc ctgctgcaac tggtattctg ctggagcaa    1680
atatctcagg tgatcttgca gatcctcagt cagccatacc caaggaaca ctcctagcca    1740
ttttaattac tacattggtt tacgtaggaa ttgcagtatc tgtaggttct tgtgttgttc   1800
gagatgccac tggaaacgtt aatgacacta tcgtaacaga gctaacaaac tgtacttctg   1860
cagcctgcaa attaaacttt gattttcat cttgtgaaag cagtccttgt tcctatgcc     1920
taatgaacaa cttccaggta atgagtatgg tgtcaggatt tacaccacta atttctgcag   1980
gtatattttc agccactctt tcttcagcat tagcatccct agtgagtgct cccaaaatat   2040
ttcaggctct atgtaaggac aacatctacc cagctttcca gatgtttgct aaaggttatg   2100
ggaaaaataa tgaacctctt cgtggctaca tcttaacatt cttaattgca cttggattca   2160
tcttaattgc tgaactgaat gttattgcac caattatctc aaacttcttc cttgcatcat   2220
atgcattgat caattttca gtattccatg catcacttgc aaaatctcca ggatggcgtc    2280
ctgcattcaa atactacaac atgtggatat cacttcttgg agcaattctt tgttgcatag   2340
taatgttcgt cattaactgg tgggctgcat tgctaacata tgtgatagtc cttgggctgt   2400
atatttatgt tacctacaaa aaaccagatg tgaattgggg atcctctaca caagccctga   2460
cttacctgaa tgcactgcag cattcaattc gtctttctgg agtggaagac cacgtgaaaa   2520
actttaggcc acagtgtctt gttatgacag gtgctccaaa ctcacgtcca gctttacttc   2580
atcttgttca tgatttcaca aaaaatgttg gtttgatgat ctgtggccat gtacatatgg   2640
gtcctcgaag acaagccatg aaagagatgt ccatcgatca agccaaatat cagcgatggc   2700
ttattaagaa caaaatgaag gcattttatg ctccagtaca tgcagatgac ttgagagaag   2760
gtgcacagta tttgatgcag gctgctggtc ttggtcgtat gaagccaaac acacttgtcc   2820
ttggatttaa gaaagattgg ttgcaagcag atatgaggga tgtggatatg tatataaact   2880
tatttcatga tgcttttgac atacaatatg gagtagtggt tattcgccta aaagaaggtc   2940
tggatatatc tcatcttcaa ggacaagaag aattattgtc atcacaagag aaatctcctg   3000
gcaccaagga tgtggtagta agtgtggaat atagtaaaaa gtccgattta gatacttcca   3060
aaccactcag tgaaaaacca attacacaca aagttgagga agaggatggc aagactgcaa   3120
ctcaaccact gttgaaaaaa gaatccaaag ccctattgt gcctttaaat gtagctgacc    3180
aaaagcttct tgaagctagt acacagtttc agaaaaaaca aggaaagaat actattgatg   3240
tctggtggct ttttgatgat ggaggtttga ccttattgat accttacctt ctgacgacca   3300
agaaaaaatg gaaagactgt aagatcagag tattccattgg tggaaagata aacagaatag   3360
accatgaccg gagagcgatg gctactttgc ttagcaagtt ccggatagac ttttctgata   3420
tcatggttct aggagatatc aataccaaac caaagaaaga aaatattata gcttttgagg   3480
aaatcattga gccatacaga cttcatgaag atgataaaga gcaagatatt gcagataaaa   3540
tgaaagaaga tgaaccatgg cgaataacag ataatgagct tgaactttat aagaccaaga   3600
cataccggca gatcaggtta aatgagttat taaaggaaca ttcaagcaca gctaatatta   3660
ttgtcatgag tctcccagtt gcacgaaaag gtgctgtgtc tagtgctctc tacatggcat   3720
ggttagaagc tctatctaag gacctaccac caatcctcct agttcgtggg aatcatcaga   3780
gtgtccttac cttctattca taaatgttct atacagtgga cagccctcca gaatggtact   3840
```

```
tcagtgccta gtgtagtaac tgaaatcttc aatgacacat taacatcaca atggcgaatg   3900 gtgactttc tttcacgatt tcattaattt gaaagcacac aggaaagttg ctccattgat    3960
aacgtgtatg gagacttcgg ttttagtcaa ttccatatct caatcttaat ggtgattctt   4020
ctctgttgaa ctgaagtttg tgagagtagt tttcctttgc tacttgaata gcaataaaag   4080
cgtgttaact ttttgattga tgaaagaagt acaaaaagcc tttagccttg aggtgccttc    4140
tgaaattaac caaatttcat ccatatatcc tcttttataa acttatagaa tgtcaaactt    4200
tgccttcaac tgttttatt tctagtctct tccactttaa aacaaaatga acactgcttg     4260
tcttcttcca ttgaccattt agtgttgagt actgtatgtg ttttgttaat tctataaagg   4320
tatctgttag atattaaagg tgagaattag ggcaggttaa tcaaaaatgg ggaaggggaa    4380
atggtaacca aaaagtaacc ccatggtaag gtttatatga gtatatgtga atatagagct   4440
aggaaaaaaa gcccccccaa ataccttttt aaccctctg attggctatt attactatat    4500
ttattattat ttattgaaac cttagggaag attgaagatt catcccatac ttctatatac   4560
catgcttaaa aatcacgtca ttctttaaac aaaaatactc aagatcattt atatttattt   4620
ggagagaaaa ctgtcctaat ttagaatttc cctcaaatct gagggacttt taagaaatgc    4680
taacagattt ttctggagga aatttagaca aaacaatgtc atttagtaga atatttcagt   4740
atttaagtgg aatttcagta tactgtacta tccttataa gtcattaaaa taatgtttca    4800
tcaaatggtt aaatggacca ctggtttctt agagaaatgt ttttaggctt aattcattca   4860
attgtcaagt acacttagtc ttaatacact caggtttgaa cagattattc tgaatattaa   4920
aatttaatcc attcttaata ttttaaaact tttgttaaga aaaactgcca gtttgtgctt   4980
ttgaaatgtc tgttttgaca tcatagtcta gtaaaatttt gacagtgcat atgtactgtt    5040
actaaaagct ttatatgaaa ttattaatgt gaagttttc atttataatt caaggaagga    5100
tttcctgaaa acatttcaag ggatttatgt ctacatattt gtgtgtgtgt gtgtatatat    5160
atgtaatatg catacacaga tgcatatgtg tatatataat gaaatttatg ttgctggtat   5220
tttgcatttt aaagtgatca agattcatta ggcaaacttt ggtttaagta aacatatgtt    5280
caaaatcaga ttaacagata caggtttcat agagaacaaa ggtgatcatt tgaagggcat   5340
gctgtaattt cacacaattt tccagttcaa aaatggagaa tacttcgcct aaaatactgt   5400
taagtgggtt aattgataca agtttctgtg gtggaaaatt tatgcaggtt ttcacgaatc    5460
cttttttttt tttttttttt tttttgagac ggagtcttgc tctgttgcca cgctggaatg    5520
cagtaacgtg atcttggctc actgcgacct ccacctcccc agttcaagcg attctcctgc   5580
ctcagcctcc ctagtagctg ggactacggg tgcacgccac catgcccagc taattttgt     5640 attttgagta gagacagggt ttcaccgtgt tggctaggat ggtgtctatc tcttgacctt    5700
gtgatccacc cgcctcagcc tcccagagtg ctgggattac aggtgcgagc cactgcgcct   5760
ggctggtttt catgaatctt gatagacatc tataacgtta ttatttcag tggtgtgcag    5820 cattttgct tcatgagtat gacctaggta tagagatctg ataacttgaa ttcagaatat     5880
taagaaaatg aagtaactga ttttctaaaa aaaaaaaaa aaaaatttc tacattataa     5940 ctcacagcat tgttccattg caggttttgc aatgtttggg ggtaaagaca gtagaaatat   6000
tattcagtaa acaataatgt gtgaactttt aagatggata atagggcatg gactgagtgc   6060
tgctatcttg aaatgtgcac aggtacactt accttttttt tttttttttt taagtttttc    6120
ccattcagga aaacaacatt gtgatctgta ctacaggaac caaatgtcat gcgtcataca    6180
tgtgggtata aagtacataa aatatatcta actattcata atgtggggtg ggtaatactg   6240
```

```
tctgtgaaat aatgtaagaa gcttttcact taaaaaaaat gcattacttt cacttaacac    6300
tagacaccag gtcgaaaatt ttcaaggtta tagtacttat ttcaacaatt cttagagatg    6360
ctagctagtg ttgaagctaa aaatagcttt atttatgctg aattgtgatt tttttatgcc    6420
aaattttttt tagttctaat cattgatgat agcttggaaa taaataatta tgccatggca    6480
tttgacagtt cattattcct ataagaatta aattgagttt agagagaatg gtggtgttga    6540
gctgattatt aacagttact gaaatcaaat atttatttgt tacattattc catttgtatt    6600
ttaggtttcc ttttacattc tttttatatg cattctgaca ttacatattt tttaagacta    6660
tggaaataat ttaaagattt aagctctggt ggatgattat ctgctaagta agtctgaaaa    6720
tgtaatattt tgataatact gtaatatacc tgtcacacaa atgcttttct aatgttttaa    6780
ccttgagtat tgcagttgct gctttgtaca gaggttactg caataaagga agtggattca    6840
ttaaacctat ttaatgtcca aaaaaaaaaa aaaaaaaaa aaaaaaaaa a               6891
```

METHODS AND COMPOSITIONS FOR THE TREATMENT OF NEUROPSYCHIATRIC DISORDERS

TECHNICAL FIELD OF THE INVENTION

The present invention relates to methods and compositions for treating selected conditions of the central and peripheral nervous systems employing non-synaptic mechanisms. More specifically, the present invention relates to methods and compositions for treating neuropsychiatric disorders by administering agents that modulate expression and/or activity of sodium-potassium-chloride co-transporters.

BACKGROUND OF THE INVENTION

Neuropathic pain and nociceptive pain differ in their etiology, pathophysiology, diagnosis and treatment. Nociceptive pain occurs in response to the activation of a specific subset of peripheral sensory neurons, the nociceptors. It is generally acute (with the exception of arthritic pain), self-limiting and serves a protective biological function by acting as a warning of on-going tissue damage. It is typically well localized and often has an aching or throbbing quality. Examples of nociceptive pain include post-operative pain, sprains, bone fractures, burns, bumps, bruises, inflammation (from an infection or arthritic disorder), obstructions and myofascial pain. Nociceptive pain can usually be treated with opioids and non-steroidal anti-inflammatory drugs (NSAIDS).

Neuropathic pain is a common type of chronic, non-malignant, pain, which is the result of an injury or malfunction in the peripheral or central nervous system and serves no protective biological function. It is estimated to affect more than 1.6 million people in the U.S. population. Neuropathic pain has many different etiologies, and may occur, for example, due to trauma, diabetes, infection with herpes zoster (shingles), HIV/AIDS peripheral neuropathies, late-stage cancer, amputation (including mastectomy), carpal tunnel syndrome, chronic alcohol use, exposure to radiation, and as an unintended side-effect of neurotoxic treatment agents, such as certain anti-HIV and chemotherapeutic drugs.

In contrast to nociceptive pain, neuropathic pain is frequently described as "burning", "electric", "tingling" or "shooting" in nature. It is often characterized by chronic allodynia (defined as pain resulting from a stimulus that does not ordinarily elicit a painful response, such as light touch) and hyperalgesia (defined as an increased sensitivity to a normally painful stimulus), and may persist for months or years beyond the apparent healing of any damaged tissues.

Neuropathic pain is difficult to treat. Analgesic drugs that are effective against normal pain (e.g., opioid narcotics and non-steroidal anti-inflammatory drugs) are rarely effective against neuropathic pain. Similarly, drugs that have activity in neuropathic pain are not usually effective against nociceptive pain. The standard drugs that have been used to treat neuropathic pain appear to often act selectively to relieve certain symptoms but not others in a given patient (for example, relief of allodynia, but not hyperalgesia). For this reason, it has been suggested that successful therapy may require the use of multiple different combinations of drugs and individualized therapy (see, for example, Bennett, *Hosp. Pract.* (Off Ed). 33:95-98, 1998). Treatment agents typically employed in the management of neuropathic pain include tricylic antidepressants (for example, amitriptyline, imipramine, desimipramine and clomipramine), systemic local anesthetics, and anti-convulsants (such as phenytoin, carbamazepine, valproic acid, clonazepam and gabapentin).

Many anti-convulsants originally developed for the treatment of epilepsy and other seizure disorders have found application in the treatment of non-epileptic conditions, including neuropathic pain, mood disorders (such as bipolar affective disorder), and schizophrenia (for a review of the use of anti-epileptic drugs in the treatment of non-epileptic conditions, see Rogawski and Loscher, *Nat. Medicine,* 10:685-692, 2004). It has thus been suggested that epilepsy, neuropathic pain and affective disorders have a common pathophysiological mechanism (Rogawski & Loscher, ibid; Ruscheweyh & Sandkuhler, *Pain* 105:327-338, 2003), namely a pathological increase in neuronal excitability, with a corresponding inappropriately high frequency of spontaneous firing of neurons. However, only some, and not all, antiepileptic drugs are effective in treating neuropathic pain, and furthermore such antiepileptic drugs are only effective in certain subsets of patients with neuropathic pain (McCleane, *Expert. Opin. Pharmacother.* 5:1299-1312, 2004).

Epilepsy is characterized by abnormal discharges of cerebral neurons and is typically manifested as various types of seizures. Epileptiform activity is identified with spontaneously occurring synchronized discharges of neuronal populations that can be measured using electrophysiological techniques. This synchronized activity, which distinguishes epileptiform from non-epileptiform activity, is referred to as "hypersynchronization" because it describes the state in which individual neurons become increasingly likely to discharge in a time-locked manner with one another. Hypersynchronized activity is typically induced in experimental models of epilepsy by either increasing excitatory or decreasing inhibitory synaptic currents, and it was therefore assumed that hyperexcitability per se was the defining feature involved in the generation and maintenance of epileptiform activity. Similarly, neuropathic pain was believed to involve conversion of neurons involved in pain transmission from a state of normal sensitivity to one of hypersensitivity (Costigan & Woolf, *Jnl. Pain* 1:35-44, 2000). The focus on developing treatments for both epilepsy and neuropathic pain has thus been on suppressing neuronal hyperexcitability by either: (a) suppressing action potential generation; (b) increasing inhibitory synaptic transmission; or (c) decreasing excitatory synaptic transmission. However, it has been shown that hypersychronous epileptiform activity can be dissociated from hyperexcitability and that the cation chloride cotransport inhibitor furosemide reversibly blocked synchronized discharges without reducing hyperexcited synaptic responses (Hochman et al. *Science* 270:99-102, 1995).

Both abnormal expression of sodium channel genes (Waxman, *Pain* 6:S133-140, 1999; Waxman et al. *Proc. Natl. Acad. Sci USA* 96:7635-7639, 1999) and pacemaker channels (Chaplan et al. *J. Neurosci.* 23:1169-1178, 2003) are believed to play a role in the molecular basis of neuropathic pain.

Neuropsychiatric disorders, including anxiety disorders, are generally treated by counseling and/or with drugs. Many of the drugs currently employed in the treatment of such disorders have significant negative side effects, such as tendencies to induce dependence.

The cation-chloride co-transporters (CCCs) are important regulators of neuronal chloride concentration that are believed to influence cell-to-cell communication, and various aspects of neuronal development, plasticity and trauma. The CCC gene family consists of three broad groups: $Na^+$—$Cl^-$ co-transporters (NCCs), $K^+$—$Cl^-$ co-transporters (KCCs) and $Na^+$—$K^+$-$2Cl^-$ co-transporters (NKCCs). Two NKCC isoforms have been identified: NKCC1 is found in a wide variety of secretory epithelia and non-epithelial cells, whereas NKCC2 is principally expressed in the kidney. For a review of NKCC1 structure, function and regulation see, Haas and Forbush, *Annu. Rev. Physiol.* 62:515-534, 2000. Randall et al. have identified two splice variants of the Slc12a2 gene that encodes NKCC1, referred to as NKCC1a and NKCC1b (*Am. J. Physiol.* 273 (*Cell Physiol.* 42):C1267-1277, 1997). The NKCC1 a gene has 27 exons, while the splice variant NKCC1b lacks exon 21. The NKCC1b splice variant is expressed primarily in the brain. NKCC1b is believed to be more than 10% more active than NKCC1a, although it is proportionally present in a much smaller amount in the brain than is NKCC1a. It has been suggested that differential splicing of the NKCC1 transcript may play a regulatory role in human tissues (Vibat et al. *Anal. Biochem.* 298:218-230, 2001). Na—K—Cl co-transport in all cell and tissues is inhibited by loop diuretics, including furosemide, bumetanide and benzmetanide.

Na—K-2Cl co-transporter knock-out mice have been shown to have impaired nociception phenotypes as well as abnormal gait and locomotion (Sung et al. *Jnl. Neurosci.* 20:7531-7538, 2000). Delpire and Mount have suggested that NKCC1 may be involved in pain perception (*Ann. Rev. Physiol.* 64:803-843, 2002). Laird et al. recently described studies demonstrating reduced stroking hyperalgesia in NKCC1 knock-out mice compared to wild-type and heterozygous mice (*Neurosci. Letts.* 361:200-203, 2004). However, in this acute pain model no difference in punctuate hyperalgesia was observed between the three groups of mice. Morales-Aza et al. have suggested that, in arthritis, altered expression of NKCC1 and the K—Cl co-transporter KCC2 may contribute to the control of spinal cord excitability and may thus represent therapeutic targets for the treatment of inflammatory pain (*Neurobiol. Dis.* 17:62-69, 2004). Granados-Soto et al. have described studies in rats in which formalin-induced nociception was reduced by administration of the NKCC inhibitors bumetanide, furosemide or piretanide (*Pain* 114:231-238, 2005). While the formalin-induced acute pain model is extensively used, it is believed to have little relevance to chronic pain conditions (Walker et al. *Mol. Med. Today* 5:319-321, 1999). Co-treatment of brain damage induced by episodic alcohol exposure with an NMDA receptor antagonist, non-NMDA receptor and $Ca^{2+}$ channel antagonists together with furosemide has been shown to reduce alcohol-dependent cerebrocortical damage by 75-85%, while preventing brain hydration and electrolyte elevations (Collins et al, *FASEB J.,* 12:221-230, 1998). The authors stated that the results suggest that furosemide and related agents might be useful as neuroprotective agents in alcohol abuse. Willis et al. have published studies indicating that nedocromil sodium, furosemide and bumetanide inhibit sensory nerve activation to reduce the itch and flare responses induced by histamine in human skin in vivo. Espinosa et al. and Ahmad et al. have previously suggested that furosemide might be useful in the treatment of certain types of epilepsy (*Medicina Espanola* 61:280-281, 1969; and *Brit. J. Clin. Pharmacol.* 3:621-625, 1976).

As with epilepsy, the focus of pharmacological intervention in neuropathic pain has been on reducing neuronal hyperexcitability. Most agents currently used to treat neuropathic pain target synaptic activity in excitatory pathways by, for example, modulating the release or activity of excitatory neurotransmitters, potentiating inhibitory pathways, blocking ion channels involved in impulse generation, and/or acting as membrane stabilizers. Conventional agents and therapeutic approaches for the treatment of neuropathic pain and neuropsychiatric disorders thus reduce neuronal excitability and inhibit synaptic firing. One serious drawback of these therapies is that they are nonselective and exert their actions on both normal and abnormal neuronal populations. This leads to negative and unintended side effects, which may affect normal CNS functions, such as cognition, learning and memory, and produce adverse physiological and psychological effects in the treated patient. Common side effects include over-sedation, dizziness, loss of memory and liver damage. There is therefore a continuing need for methods and compositions for treating neuronal disorders that disrupt hyper-synchronized neuronal activity without diminishing the neuronal excitability and spontaneous synchronization required for normal functioning of the peripheral and central nervous systems.

SUMMARY OF THE INVENTION

The treatment compositions and methods of the present invention are useful for treating conditions including neuropathic pain and neuropsychiatric disorders, such as bipolar disorders, anxiety disorders (including panic disorder, social anxiety disorder, obsessive compulsive disorder, posttraumatic stress disorder, generalized anxiety disorder and specific phobia (American Psychiatric Association, Diagnostic and Statistical Manual of Mental Disorders, $4^{th}$ edition—Text Revision, 2000)), depression and schizophrenia, that are characterized by neuronal hypersynchrony. The inventive compositions and methods may be employed to reduce neuronal hypersynchrony associated with neuropathic pain and/or neuropsychiatric disorders without suppressing neuronal excitability, thereby avoiding the unwanted side effects often associated with agents currently employed for the treatment of, neuropathic pain and neuropsychiatric disorders.

The methods and compositions disclosed herein generally involve via non-synaptic mechanisms and modulate, generally reduce, the synchronization of neuronal population activity. The synchronization of neuronal population activity is modulated by manipulating anionic concentrations and gradients in the central and/or peripheral nervous systems. More specifically, the inventive compositions are capable of reducing the effective amount, inactivating, and/or inhibiting the activity of a $Na^+$—$K^+$-$2Cl^-$ (NKCC) co-transporter. Especially preferred treatment agents of the present invention, exhibit a high degree of NKCC co-transporter antagonist activity in cells of the central and/or peripheral nervous system, e.g., glial cells, Schwann cells and/or neuronal cell populations, and exhibit a lesser degree of activity in renal cell populations. In one embodiment, the inventive compositions are capable of reducing the effective amount, inactivating, and/or inhibiting the activity of the co-transporter NKCC1. NKCC1 antagonists are especially preferred treatment agents for use in the inventive methods. NKCC co-transporter antagonists that may be usefully employed in the inventive treatment compositions include, but are not limited to, CNS-targeted NKCC co-transporter antagonists such as furosemide, bumetanide, ethacrynic acid, torsemide, azosemide, muzolimine, piretanide, tripamide and the like, as well as thiazide and thiazide-like diuretics, such as bendroflumethiazide, benzthiazide, chlorothiazide, hydrochlorothiazide, hydroflumethiazide, methylclothiazide, polythiazide, trichlormethiazide, chlorthalidone, indapamide, metolazone and quinethazone, together with analogs and functional derivatives of such components.

Analogs of CNS-targeted NKCC co-transporter antagonists such as furosemide, bumetanide, piretanide, azosemide and torsemide that may be usefully employed in the inventive compositions and methods include those provided below as Formulas I-V. The inventors believe that such analogs have increased lipophilicity and reduced diuretic effects compared to the CNS-targeted NKCC co-transporter antagonists from which they are derived and thus result in fewer undesirable side effects when employed in the inventive treatment methods.

In one embodiment, the level of diuresis that occurs following administration of an effective amount of an analog provided below as Formula I-V, is less than 99%, 90%, 80%, 70%, 60%, 50%, 40%, 30%, 20% or 10% of that which occurs following administration of an effective amount of the parent molecule from which the analog is derived. For example, the analog may be less diuretic than the parent molecule when administered at the same mg/kg dose. Alternatively, the analog may be more potent than the parent molecule from which it is derived, so that a smaller dose of the analog is required for effective relief of symptoms, thereby eliciting less of a diuretic effect. Similarly, the analog may have a longer duration of effect in treating disorders than the parent molecule, so that the analog may be administered less frequently than the parent molecule, thus leading to a lower total diuretic effect within any given period of time.

Other treatment agents that may be usefully employed in the inventive compositions and methods include, but are not limited to: antibodies, or antigen-binding fragments thereof, that specifically bind to NKCC1; soluble NKCC1 ligands; small molecule inhibitors of NKCC1; anti-sense oligonucleotides to NKCC1; NKCC1-specific small interfering RNA molecules (siRNA or RNAi); and engineered soluble NKCC1 molecules. Preferably, such antibodies, or antigen-binding fragments thereof, and small molecule inhibitors of NKCC1 specifically bind to the domains of NKCC1 involved in bumetanide binding, as described, for example, in Haas and Forbush II, *Annu. Rev. Physiol.* 62:515-534, 2000. The polypeptide sequence for human NKCC1 is provided in SEQ ID NO: 1, with the corresponding cDNA sequence being provided in SEQ ID NO: 2.

As the methods and treatment agents of the present invention employ "non-synaptic" mechanisms, little or no suppression of neuronal excitability occurs. More specifically, the inventive treatment agents cause little (less than a 1% change compared to pre-administration levels) or no suppression of action potential generation or excitatory synaptic transmission. In fact, a slight increase in neuronal excitability may occur upon administration of certain of the inventive treatment agents. This is in marked contrast to conventional anti-epileptic drugs currently used in the treatment of neuropathic pain, which do suppress neuronal excitability. The methods and treatment agents of the present invention affect the synchronization, or relative synchrony, of neuronal population activity. Preferred methods and treatment agents modulate the extracellular anionic chloride concentration and/or the gradients in the central or peripheral nervous system to reduce neuronal synchronization, or relative synchrony, without substantially affecting neuronal excitability.

In one aspect, the present invention relates to methods and agents for relieving neuropathic pain, or the abnormal perception of pain, by affecting or modulating spontaneous hypersynchronized bursts of neuronal activity and the propagation of action potentials or conduction of impulses in certain cells and nerve fibers of the peripheral nervous system, for example, primary sensory afferent fibers, pain fibers, dorsal horn neurons, and supraspinal sensory and pain pathways.

The inventive treatment agents may be employed in combination with other, known, treatment agents, such as those presently used in the treatment of neuropsychiatric disorders. One of skill in the art will appreciate that the combination of a treatment agent of the present invention with another, known, treatment agent may involve both synaptic and non-synaptic mechanisms.

Treatment compositions and methods of the present invention may be used therapeutically and episodically following the onset of symptoms or prophylactically, prior to the onset of specific symptoms. For example, treatment agents of the present invention can be used to treat existing neuropathic pain or to protect nerves from neurotoxic injury and neuropathic pain secondary to chemotherapy, radiotherapy, exposure to infectious agents, and the like.

In certain embodiments, the treatment agents employed in the inventive methods are capable of crossing the blood brain barrier, and/or are administered using delivery systems that facilitate delivery of the agents to the central nervous system. For example, various blood brain barrier (BBB) permeability enhancers can be used, if desired, to transiently and reversibly increase the permeability of the blood brain barrier to a treatment agent. Such BBB permeability enhancers may include leukotrienes, bradykinin agonists, histamine, tight junction disruptors (e.g., zonulin), hyperosmotic solutions (e.g., mannitol), cytoskeletal contracting agents, short chain alkylglycerols (e.g., 1-O-pentylglycerol), and others which are currently known in the art.

The above-mentioned and additional features of the present invention, together with the manner of obtaining them, will be best understood by reference to the following more detailed description. All references disclosed herein are hereby incorporated by reference in their entirety as if each was incorporated individually.

BRIEF DESCRIPTION OF THE DRAWINGS

FIGS. 1A, 1A1, 1B, 1B1, 1C, 1C1 and 1D show the effect of furosemide on stimulation evoked after discharge activity in rat hippocampal slices.

FIGS. 3A-3H show furosemide blockade of kainic acid-evoked electrical "status epilepticus" in urethane-anesthetized rats, with EKG recordings shown in the upper traces and cortical EEG recordings shown in the bottom traces.

DETAILED DESCRIPTION OF THE INVENTION

Figure 2A:
FIGS. 2A-2R show furosemide blockade of spontaneous epileptiform burst discharges across a spectrum of in vitro models.

As discussed above, preferred treatment agents and methods of the present invention, for use in treating neuropathic pain and/or neuropsychiatric disorders, modulate or disrupt the synchrony of neuronal population activity in areas of heightened synchronization by reducing the activity of NKCC co-transporters. As described in detail below and illustrated in the examples, movement of ions and modulation of ionic gradients by means of ion-dependent co-transporters, preferably cation-chloride dependent co-transporters, is critical to regulation of neuronal synchronization. Chloride co-transport function has long been thought to be directed primarily to movement of chloride out of cells. The sodium independent transporter, which has been shown to be neuronally localized, moves chloride ions out of neurons. Blockade of this transporter, such as by administration of the loop diuretic furosemide, leads to hyperexcitability, which is the short-term response to cation-chloride co-transporters such as furosemide. However, the long-term response to furosemide demonstrates that the inward, sodium-dependent movement of chloride ions, mediated by the glial associated $Na^+$—$K^+$-$2Cl^-$ co-transporter NKCC1, plays an active role in blocking neuronal synchronization, without affecting excitability and stimulus-evoked cellular activity. Haglund and Hochman have demonstrated that furosemide is able to block epileptic activity in humans while not affecting normal brain activity (*J. Neurophysiol.* (Feb. 23, 2005) doi:10.1152/jn.00944.2004). These results provide support for the belief that the inventive methods and compositions may be effectively employed in the treatment of neuropathic pain without giving rise to undesirable side effects often seen with conventional treatments.

As discussed above, the NKCC1 splice variant referred to as NKCC1b is more active than the NKCC1a variant. A central or peripheral nervous system which expresses a few more percentage NKCC1b may thus be more prone to disorders such as neuropathic pain and epilepsy. Similarly, a treatment agent that is more specific for NKCC1b compared to NKCC1a may be more effective in the treatment of such disorders.

The inventive methods may be used for the treatment and/or prophylaxis of neuropathic pain having, for example, the following etiologies: alcohol abuse; diabetes; eosinophilia-myalgia syndrome; Guillain-Barre syndrome; exposure to heavy metals such as arsenic, lead, mercury, and thallium; HIV/AIDS; exposure to anti-HIV/AIDS drugs; malignant tumors; medications including amiodarone, aurothioglucose, cisplatinum, dapsone, stavudine, zalcitabine, didanosine, disulfiram, FK506, hydralazine, isoniazid, metronidazole, nitrofurantoin, paclitaxel, phenytoin and vincristine; monoclonal gammopathies; multiple sclerosis; post-stroke central pain, postherpetic neuralgia; trauma including carpal tunnel syndrome, cervical or lumbar radiculopathy, complex regional pain syndrome, spinal cord injury and stump pain; trigeminal neuralgia; vasculitis; vitamin B6 megadosing; and certain vitamin deficiencies (B12, B1, B6, E). Neuropsychiatric disorders that may be effectively treated using the inventive methods include, but are not limited to, bipolar disorders, anxiety disorders, panic disorders, depression, schizophrenia, obsessive-compulsive disorders and post-traumatic stress syndrome.

Compositions that may be effectively employed in the inventive methods are capable of reducing the effective amount, inactivating, and/or inhibiting the activity of a $Na^+$—$K^+$-$2Cl^-$ (NKCC) co-transporter. Preferably such compositions are capable of reducing the effective amount, inactivating, and/or inhibiting the activity of the co-transporter NKCC1. In certain embodiments, the inventive compositions comprise at least one treatment agent selected from the group consisting of: antagonists of NKCC1 (including but not limited to, small molecule inhibitors of NKCC1, antibodies, or antigen-binding fragments thereof, that specifically bind to NKCC1 and soluble NKCC1 ligands); anti-sense oligonucleotides to NKCC1; NKCC1-specific small interfering RNA molecules (siRNA or RNAi); and engineered soluble NKCC1 molecules. In preferred embodiments, the treatment agent is selected from the group consisting of: CNS-targeted NKCC co-transporter antagonists such as furosemide, bumetanide, ethacrynic acid, torsemide, azosemide, muzolimine, piretanide, tripamide and the like; thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; and analogs and functional derivatives of such components.

Analogs of CNS-targeted NKCC co-transporter antagonists that may be employed in the inventive methods include compounds according to formula I, II and/or III:

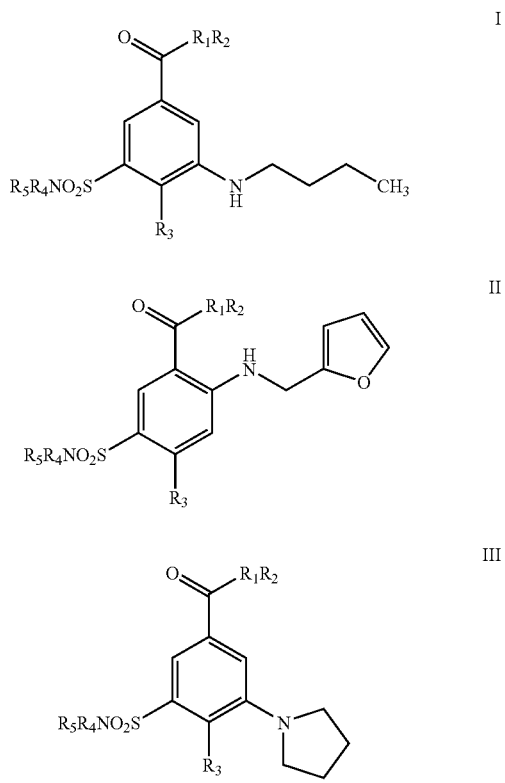

or a pharmaceutically acceptable salt, solvate, tautomer or hydrate thereof, wherein R₁ is not present, H or O;

R₂ is H or when R₁ is O, is selected from the group consisting of: alkylaminodialkyl, alkylaminocarbonyldialkyl, alkyloxycarbonylalkyl, alkylaldehyde, alkylketoalkyl, alkylamide, an alkylammonium group, alkylcarboxylic acid, alkylheteroaryls, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkylalkyl and methylthioalkaryl, unsubstituted or substituted, and when R₁ is not present, R₂ is selected from the group consisting of: hydrogen, dialkylamino, diarylamino, dialkylaminodialkyl, dialkylcarbonylaminodialkyl, dialkylesteralkyl, dialkylaldehyde, dialkylketoalkyl, dialkylamido, dialkylcarboxylic acid, and dialkylheteroaryls, unsubstituted or substituted;

R₃ is selected from the group consisting of: aryl, halo, hydroxy, alkoxy, and aryloxy, unsubstituted or substituted; and R₄ and R₅ are each independently selected from the group consisting of: hydrogen, alkylaminodialkyl, alkylhydroxyaminodiakyl, unsubstituted or substituted:

In some embodiments of the present invention, the analog can be bumetanide aldehyde, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, bumetanide methoxy(polyethyleneoxy)$_{n-1}$-ethyl ester, _____ bumetanide benzyltrimethylammonium salt, and bumetanide cetyltrimethylammonium salt.

According to further embodiments of the present invention, the analog can be furosemide aldehyde, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide dibenzylamide, furosemide benzyltrimethylammonium salt, furosemide cetyltrimethylammonium salt, furosemide N,N-dimethylglycolamide ester, furosemide methoxy(polyethyleneoxy)$_{n-1}$-ethyl ester, furosemide pivaxetil ester and furosemide propaxetil ester.

In still further embodiments of the present invention, the analog can be piretanide aldehyde, piretanide methyl ester, piretanide cyanomethyl ester, piretanide benzyl ester, piretanide morpholinoethyl ester, piretanide 3-(dimethylaminopropyl) ester, piretanide N,N-diethylglycolamide ester, piretanide diethylamide, piretanide dibenzylamide, piretanide benzylltrimethylammonium salt, piretanide cetylltrimethylammonium salt, piretanide N,N-dimethylglycolamide ester, piretanide methoxy(polyethyleneoxy)$_{n-1}$-ethyl ester, piretanide pivaxetil ester and/or piretanide propaxetil ester.

Analogs of CNS-targeted NKCC co-transporter anatagonists that may be usefully employed in the methods of the present invention further include compounds according to formula IV:

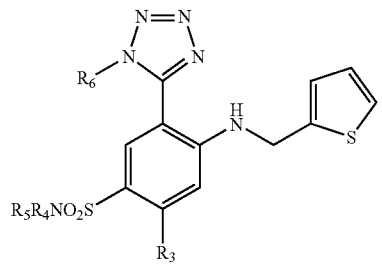

or a pharmaceutically acceptable salt, solvate, tautomer or hydrate thereof, wherein R₃, R₄ and R₅ are defined above; and R₆ is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted.

In some embodiments of the present invention, the analog may be selected from the group consisting of: tetrazolyl-substituted azosemides (such as methoxymethyl tetrazolyl-substituted azosemides, methylthiomethyl tetrazolyl-substituted azosemides and N-mPEG350-tetrazolyl-substituted azosemides), azosemide benzyltrimethylammonium salt and/or azosemide cetyltrimethylammonium salt.

Analogs that may usefully be employed in the inventive methods further include compounds according to formula V:

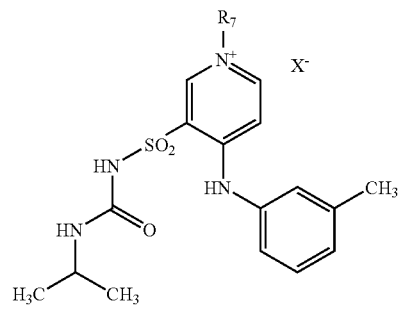

or a pharmaceutically acceptable salt, solvate, tautomer or hydrate thereof, wherein R₇ is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted; and X⁻ is a halide such as bromide, chloride, fluoride, iodide or an anionic moiety such as mesylate or tosylate; alternatively, X⁻ is not present and the compound forms an "inner" or zwitterionic salt by loss of a proton from the sulfonylurea moiety (—SO₂—NH—CO—).

In some embodiments of the present invention, the analog may be selected from the group consisting of: pyridine-substituted torsemide quaternary ammonium salts or the corresponding inner salts (zwitterions). Examples include, but are not limited to, methoxymethyl pyridinium torsemide salts, methylthiomethyl pyridinium torsemide salts and N-mPEG350-pyridinium torsemide salts.

Any of the R groups as defined herein can be excluded from the analogs disclosed herein.

Intermediate compounds formed through the synthetic methods described below to provide the compounds of formula I, II, III, IV and/or V may also possess utility as a therapeutic agent for neuropsychiatric disorders described herein.

Modification of the CNS-targeted NKCC co-transport antagonists employed in the inventive methods can include reacting the antagonist with a functional group and/or compound selected from the group consisting of: an aluminum hydride, alkyl halide, alcohol, aldehyde, aryl halide, alkyl amide, aryl amine and quaternary ammonium salt, unsubstituted or substituted, or combinations thereof. Non-limiting examples of compounds that may be used as a starting material are exemplified below.

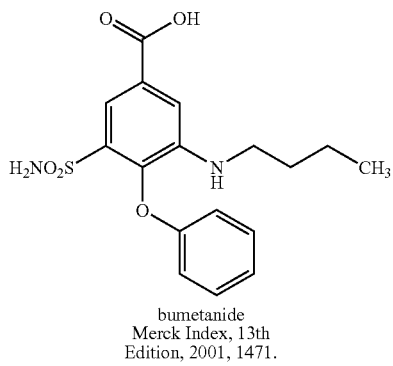

bumetanide
Merck Index, 13th
Edition, 2001, 1471.

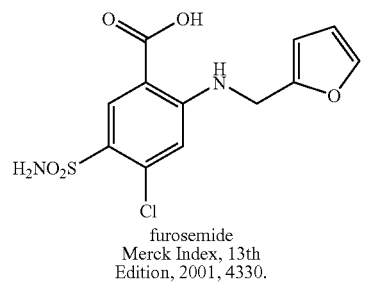

furosemide
Merck Index, 13th
Edition, 2001, 4330.

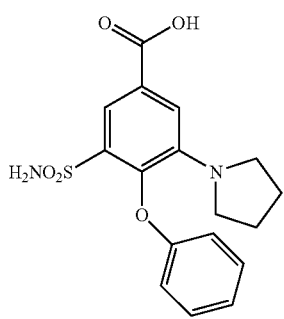

piretanide
Merck Index, 13th
Edition, 2001, 7575.

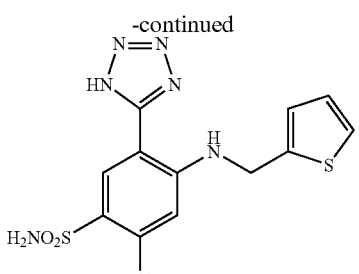

azosemide
Merck Index, 13th
Edition, 2001, 924.

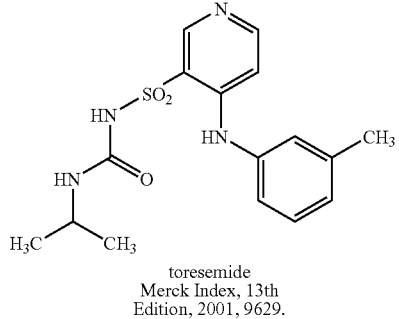

toresemide
Merck Index, 13th
Edition, 2001, 9629.

The term "alkyl" as used herein refers to a straight or branched chain saturated or partially unsaturated hydrocarbon radical. Examples of alkyl groups include, but are not limited to, methyl, ethyl, isopropyl, tert-butyl, n-pentyl and the like. By "unsaturated" is meant the presence of 1, 2 or 3 double or triple bonds, or a combination thereof. Such alkyl groups may be optionally substituted as described below.

The term "alkylene" as used herein refers to a straight or branched chain having two terminal monovalent radical centers derived by the removal of one hydrogen atom from each of the two terminal carbon atoms of straight-chain parent alkane.

The term "aryl" as used herein refers to an aromatic group or to an optionally substituted aromatic group fused to one or more optionally substituted aromatic groups, optionally substituted with suitable substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

The term "halo" as used herein refers to bromo, chloro, fluoro or iodo. Alternatively, the term "halide" as used herein refers to bromide, chloride, fluoride or iodide.

The term "hydroxy" as used herein refers to the group —OH.

The term "alkoxy" as used herein alone or as part of another group, refers to an alkyl group, as defined herein, appended to the parent molecular moiety through an oxy group. Representative examples of alkoxy include, but are not limited to, methoxy, ethoxy, propoxy, 2-propoxy, butoxy, tert-butoxy, pentyloxy, hexyloxy and the like.

The term "aryloxy" as used herein refers to the group —ArO wherein Ar is aryl or heteroaryl. Examples include, but are not limited to, phenoxy, benzyloxy and 2-naphthyloxy.

The term "amino" as used herein refers to —NH$_2$ in which one or both of the hydrogen atoms may optionally be replaced by alkyl or aryl or one of each, optionally substituted.

The term "alkylthio" as used herein alone or as part of another group, refers to an alkyl group, as defined herein, appended to the parent molecular moiety through a sulfur moiety. Representative examples of alkylthio include, but are not limited to, methylthio, ethylthio, n-propylthio, isopropylthio, n-butylthio, and the like.

The term "carboxy" as used herein refers to the group —CO₂H.

The term "quaternary ammonium" as used herein refers to a chemical structure having four bonds to the nitrogen with a positive charge on the nitrogen in the "onium" state, i.e., "R₄N⁺" or "quaternary nitrogen," wherein R is an organic substituent such as alkyl or aryl. The term "quaternary ammonium salt" as used herein refers to the association of the quaternary ammonium with a cation.

The term "substituted" as used herein refers to replacement of one or more of the hydrogen atoms of the group replaced by substituents known to those skilled in the art and resulting in a stable compound as described below. Examples of suitable replacement groups include, but are not limited to, alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, ureido and the like. Substitutions are permissible when such combinations result in compounds stable for the intended purpose. For example, substitutions are permissible when the resultant compound is sufficiently robust to survive isolation to a useful degree of purity from a reaction mixture, and formulation into a therapeutic or diagnostic agent.

The term "solvate" as used herein is intended to refer to a pharmaceutically acceptable solvate form of a specified compound that retains the biological effectiveness of such compound, for example, resulting from a physical association of the compound with one or more solvent molecules. Examples of solvates, without limitation, include compounds of the invention in combination with water, isopropanol, ethanol, methanol, DMSO, ethyl acetate, acetic acid, or ethanolamine.

The term "hydrate" as used herein refers to the compound when the solvent is water.

The term "biocompatible polymer" as used herein refers to a polymer moiety that is substantially non-toxic and does not tend to produce substantial immune responses, clotting or other undesirable effects. Polyalkylene glycol is a biocompatible polymer where, as used herein, polyalkylene glycol refers to straight or branched polyalkylene glycol polymers such as polyethylene glycol, polypropylene glycol, and polybutylene glycol, and further includes the monoalkylether of the polyalkylene glycol. In some embodiments of the present invention, the polyalkylene glycol polymer is a lower alkyl polyalkylene glycol moiety such as a polyethylene glycol moiety (PEG), a polypropylene glycol moiety, or a polybutylene glycol moiety. PEG has the formula —HO(CH₂CH₂O)$_n$H, where n can range from about 1 to about 4000 or more. In some embodiments, n is 1 to 100, and in other embodiments, n is 5 to 30. The PEG moiety can be linear or branched. In further embodiments, PEG can be attached to groups such as hydroxyl, alkyl, aryl, acyl or ester. In some embodiments, PEG can be an alkoxy PEG, such as methoxy-PEG (or mPEG), where one terminus is a relatively inert alkoxy group, while the other terminus is a hydroxyl group.

The compounds of formula I, II, III, IV and/or V can be synthesized using traditional synthesis techniques well known to those skilled in the art. More specific synthesis routes are described below.

The bumetanide analogs are synthesized by reacting the carboxylic acid moiety of bumetanide with various reagents. For example, bumetanide may undergo esterification via reaction with alcohols, including linear, branched, substituted, or unsubstituted alcohols. Bumetanide may also be alkylated via reaction with suitable substituted and unsubstituted alkyl halides and aryl halides, including chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like, or alkyloxy(polyalkyloxy)alkyl tosylates such as MeO-PEG1000-OTs and the like. "Axetil"-type esters may also be formed by alkylation using alkyl halides such as chloromethyl pivalate or chloromethyl propionate. Bumetanide may also undergo amidation by reaction with suitable substituted or unsubstituted alkyl amines or aryl amines, either after conversion to the acid chloride or by using an activator, such as 1-ethyl-3-(3-dimethylaminopropyl)carbodiimide (EDC). Bumetanide may also be reacted with a quaternary ammonium hydroxide, such as benzyltrimethylammonium hydroxide or cetyltrimethylammonium hydroxide, to form bumetanide quaternary ammonium salts. Schemes 1 and 7 below presents a synthesis scheme of some exemplary compounds according to formula I.

Scheme 1. Synthesis of Exemplary Compounds According to Formula I.

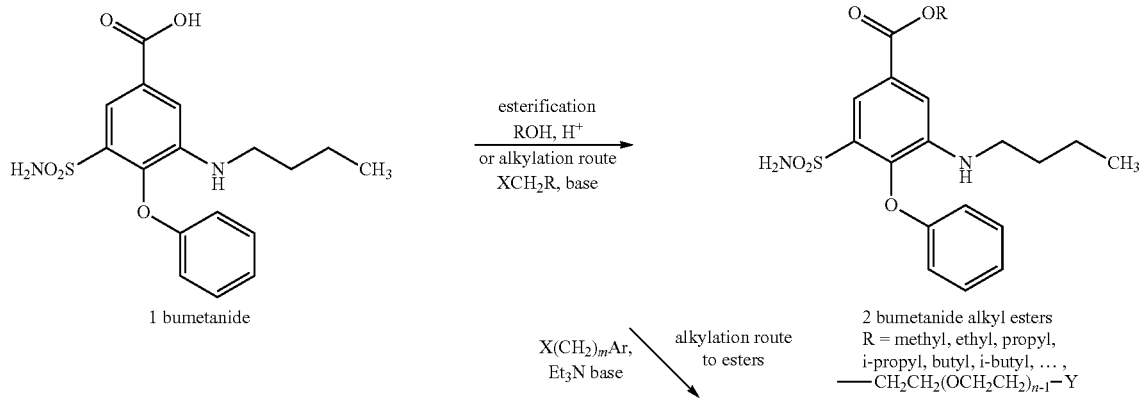

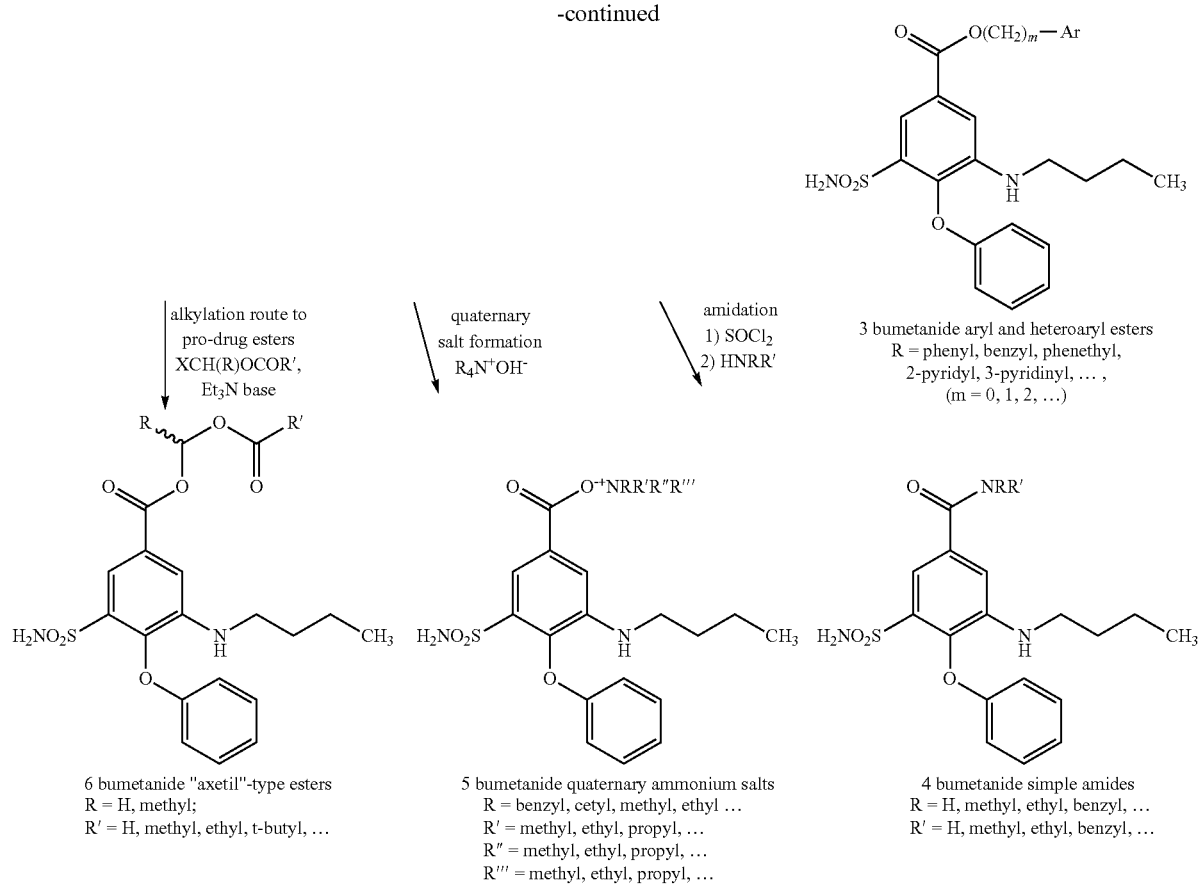

The furosemide analogs are synthesized by methods analogous to those used in the synthesis of the bumetanide analogs. Specifically, furosemide may undergo esterification via reaction with alcohols, including linear, branched, substituted, or unsubstituted alcohols. Furosemide may also be alkylated via reaction with suitable substituted and unsubstituted alkyl halides and aryl halides, including for example, chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like, or alkyloxy(polyalkyloxy)alkyl tosylates such as MeO-PEG1000-OTs and the like. "Axetil"-type esters may also be formed by alkylation using alkyl halides such as chloromethyl pivalate or chloromethyl propionate. Furosemide may also undergo amidation by reaction with suitable substituted or unsubstituted alkyl amines or aryl amines, either after conversion to the acid chloride or by using an activator, such as 1-ethyl-3-(3-dimethylaminopropyl)carbodiimide (EDC). Furosemide may also be reacted with a quaternary ammonium hydroxide, such as benzyltrimethylammonium hydroxide or cetyltrimethylammonium hydroxide, to form furosemide quaternary ammonium salts. Scheme 2 below presents a synthesis scheme of some exemplary compounds according to formula II.

Scheme 2. Synthesis of Exemplary Compounds According to Formula II.

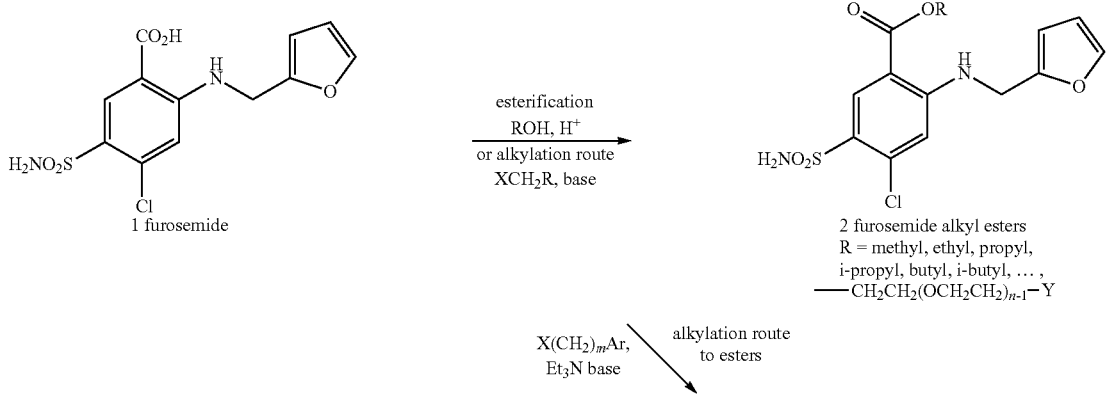

-continued

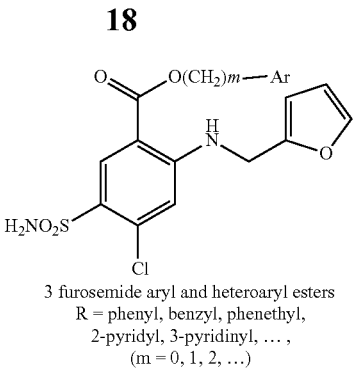

3 furosemide aryl and heteroaryl esters
R = phenyl, benzyl, phenethyl,
2-pyridyl, 3-pyridinyl, ... ,
(m = 0, 1, 2, ...)

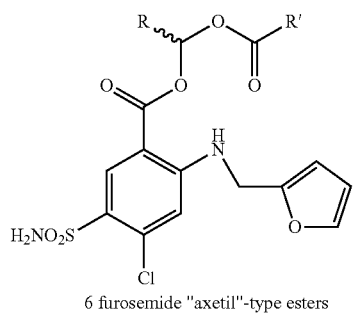

6 furosemide "axetil"-type esters
R = H, methyl;
R' = H, methyl, ethyl, t-butyl, ...

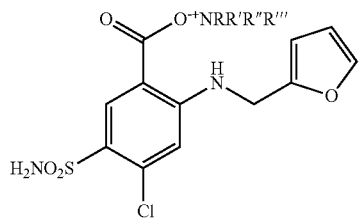

5 furosemide quaternary ammonium salts
R = benzyl, cetyl, methyl, ethyl ...
R' = methyl, ethyl, propyl, ...
R'' = methyl, ethyl, propyl, ...
R''' = methyl, ethyl, propyl, ...

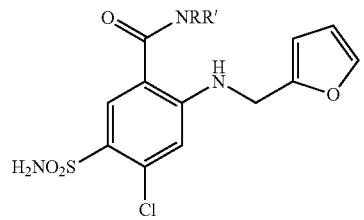

4 furosemide simple amides
R = H, methyl, ethyl, benzyl, ...
R' = H, methyl, ethyl, benzyl, ...

The piretanide analogs are synthesized by methods analogous to those used in the synthesis of the bumetanide analogs. Specifically, piretanide may undergo esterification via reaction with alcohols, including linear, branched, substituted, or unsubstituted alcohols. Piretanide may also be alkylated via reaction with suitable substituted and unsubstituted alkyl halides and aryl halides, including chloroacetonitrile, benzyl chloride, 1-(dimethylamino)propyl chloride, 2-chloro-N,N-diethylacetamide, and the like. PEG-type esters may be formed by alkylation using alkyloxy(polyalkyloxy)alkyl halides such as MeO-PEG350-Cl and the like, or alkyloxy(polyalkyloxy)alkyl tosylates such as MeO-PEG1000-OTs and the like. "Axetil"-type esters may also be formed by alkylation by using alkyl halides such as chloromethyl pivalate or chloromethyl propionate. Piretanide may also undergo amidation by reaction with suitable substituted or unsubstituted alkyl amines or aryl amines, either after conversion to the acid chloride or by using an activator, such as 1-ethyl-3-(3-dimethylaminopropyl)carbodiimide (EDC). Piretanide may also be reacted with a quaternary ammonium hydroxide, such as benzyltrimethylammonium hydroxide or cetyltrimethylammonium hydroxide, to form piretanide quaternary ammonium salts. Scheme 3 below presents a synthesis scheme of some exemplary compounds according to formula III.

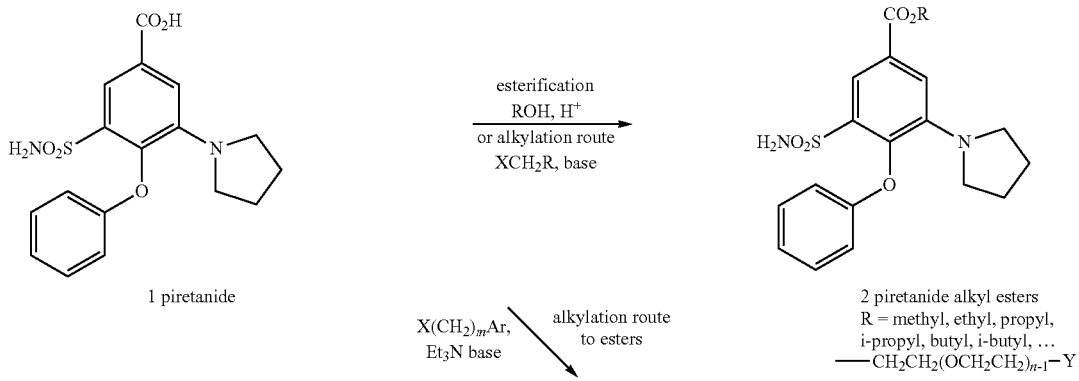

Scheme 3. Synthesis of Exemplary Compounds According to Formula III.

-continued

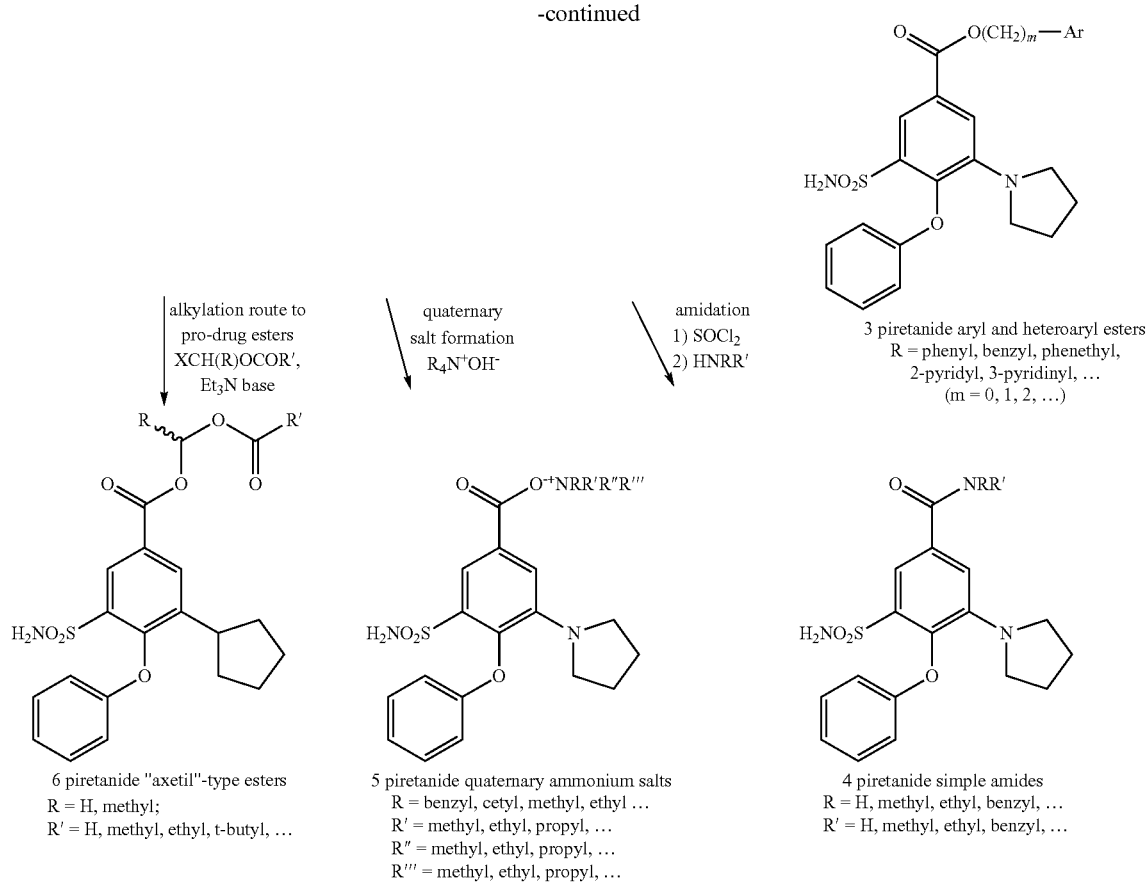

The azosemide analogs are synthesized by the reaction of various reagents with the tetrazolyl moiety of azosemide. Azosemide may undergo hydroxyalkylation with the addition of an aldehyde, whereby a hydroxyalkyl functionality is formed. An alcohol may optionally be reacted along with the aldehyde to obtain an ether. An alkyl thiol may optionally be added with the aldehyde to form a thioether. Azosemide may also be alkylated by the addition of suitable alkyl halides or aryl halides, including alkyl or aryl halides comprising an ether or thioether linkage, such as methyl chloromethyl ether and benzyl chloromethyl thioether. PEG-type ethers may be formed by alkylation using alkyloxy(polyalkyloxy)alkyl halides such as MeO-PEG350-Cl and the like, or alkyloxy (polyalkyloxy)alkyl tosylates such as MeO-PEG1000-OTs and the like. "Axetil"-type analogs may also be formed via addition of alkyl or aryl halides, such as chloromethyl pivalate or chloromethyl propionate. Azosemide may be reacted with a quaternary ammonium salt, such as benzyltrimethylammoniumbromide and base such as sodium hydroxide or cetyltrimethylammonium bromide and base such as sodium hydroxide, in order to form an azosemide quaternary ammonium salt. Scheme 4 below presents a synthesis scheme of some exemplary compounds according to formula IV.

Scheme 4. Synthesis of Exemplary Compounds According to Formula IV.

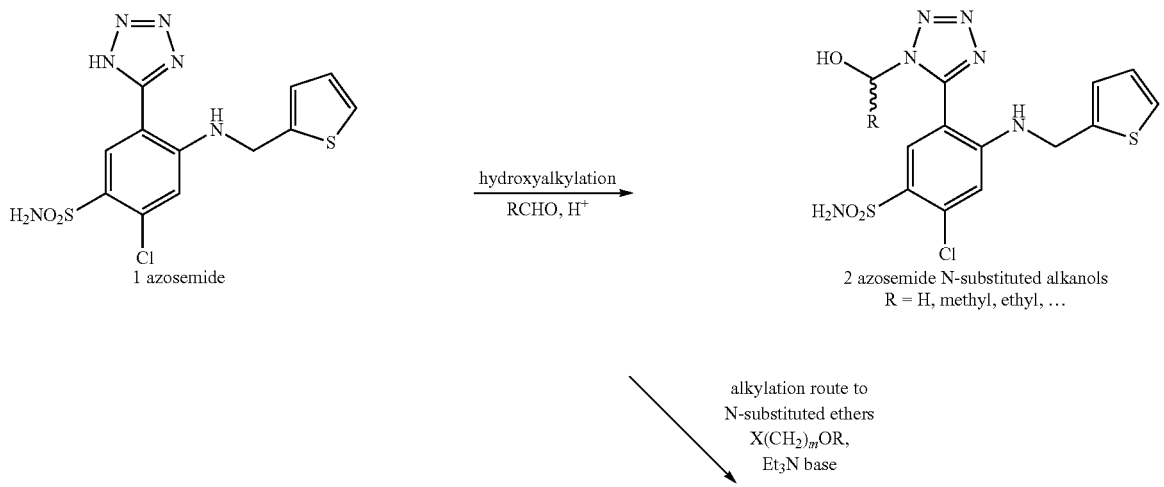

-continued

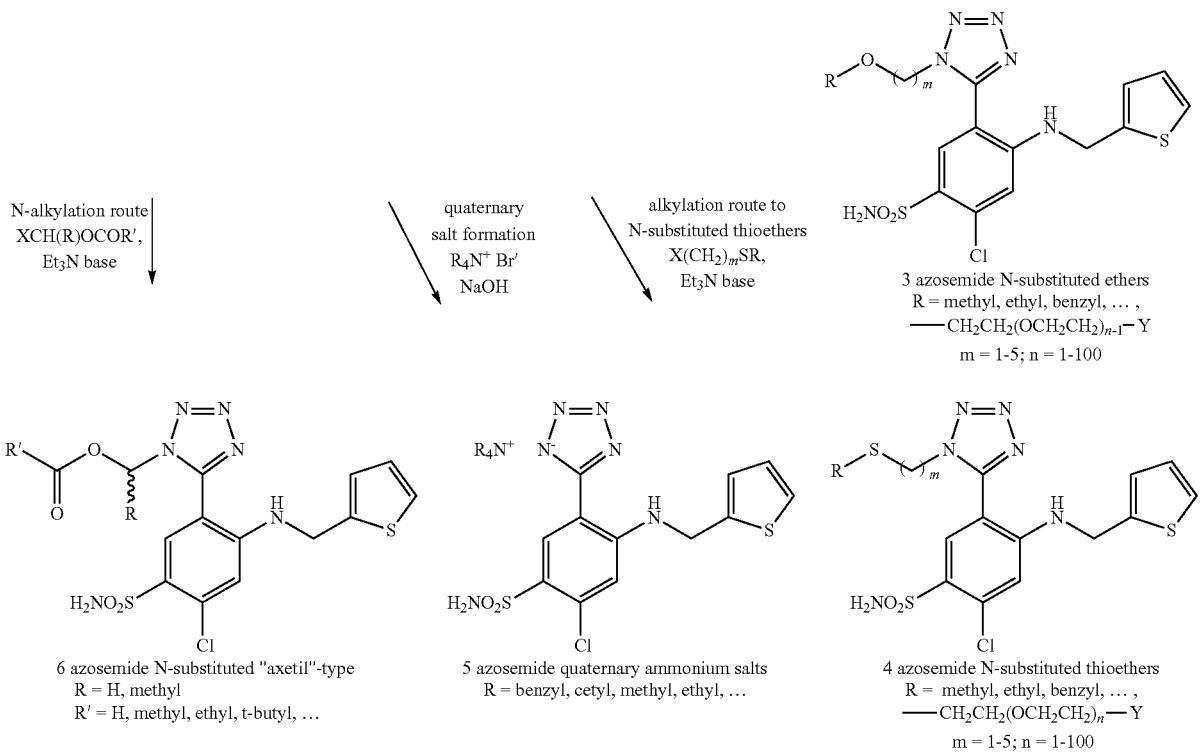

The torsemide (also known as torasemide) analogs are synthesized by the reaction of various reagents with the pyridine moiety of torsemide. Torsemide may undergo alkylation by the addition of suitable alkyl or aryl halides, including benzyl chloride, to form N-substituted quaternary ammonium salts. Alkyl halides and aryl halides comprising an ether linkage, including methyl chloromethyl ether and benzyl chloromethyl ether, may be used to form N-substituted ether quaternary ammonium salts. Alkyl halides and aryl halides comprising a thioether linkage, including methyl chloromethyl thioether and benzyl chloromethyl thioether, may be used to form N-substituted thioether quaternary ammonium salts. PEG-type ether-containing quaternary ammonium salts may be formed by alkylation using alkyloxy(polyalkyloxy)alkyl halides such as MeO-PEG350-Cl and the like, or alkyloxy(polyalkyloxy)alkyl tosylates such as MeO-PEG1000-OTs and the like. "Axetil"-type quaternary ammonium salts may also be formed via the addition of alkyl halides such as chloromethyl pivalate or chloromethyl propionate. Scheme 5 below presents a synthesis scheme of some exemplary compounds according to formula V.

Scheme 5. Synthesis of Exemplary Compounds According to Formula V.

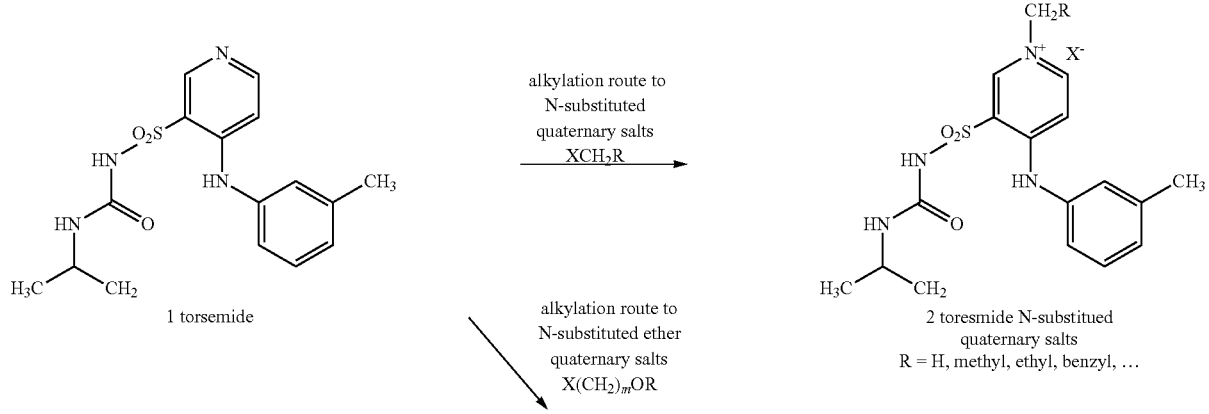

-continued

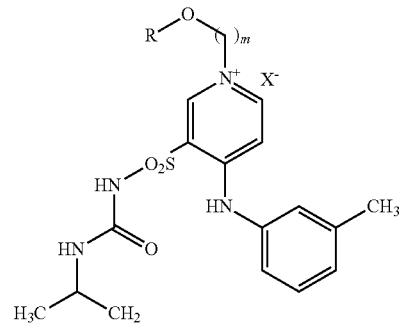

3 torsemide N-substituted ether quaternary
R = methyl, ethyl, benzyl, …
——CH$_2$CH$_2$(OCH$_2$CH$_2$)$_{n-1}$—Y
m = 1-5; n = 1-100 alkylation route to "axetil" quaternary salts
XCH(R)OCOR'

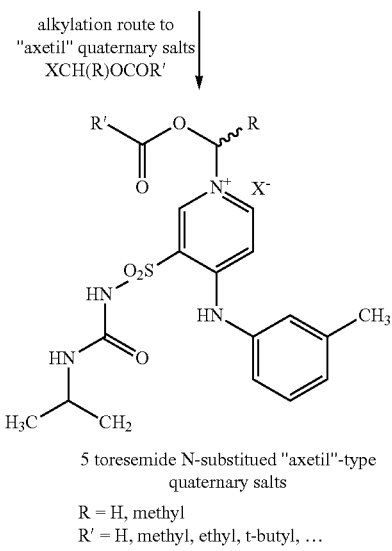

5 toresemide N-substitued "axetil"-type quaternary salts
R = H, methyl
R' = H, methyl, ethyl, t-butyl, … alkylation route to N-substitued thioether quaternary salts
X(CH$_2$)$_m$SR

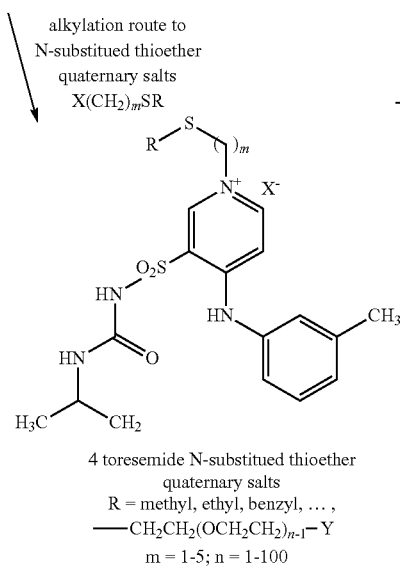

4 toresemide N-substitued thioether quaternary salts
R = methyl, ethyl, benzyl, …,
——CH$_2$CH$_2$(OCH$_2$CH$_2$)$_{n-1}$—Y
m = 1-5; n = 1-100

The substituted benzoic acids bumetanide, piretanide and furosemide can be selectively reduced to the corresponding bumetanide aldehyde, piretanide aldehyde and furosemide aldehyde using amine-substituted ammonium hydrides such as bis(4-methylpiperazinyl)aluminum hydride by literature methods. See Muraki, M. and Mukiayama, T., *Chem. Letters*, 1974, 1447; Muraki, M. and Mukiayama, T., *Chem. Letters*, 1975, 215; and Hubert, T. et al., *J. Org. Chem.*, 1984, 2279. It is well known that the more lipophilic benzaldehydes readily air-oxidize into the more hydrophilic benzoic acids and that benzaldehydes are also metabolized into the corresponding benzoic acids in vivo, via the use of NADPH co-factor and with a number of oxidative P450 enzymes.

Scheme 6. Synthesis of Exemplary Benzaldehyde Analogs of Bumetanide, Piretanide and Furosemide.

-continued

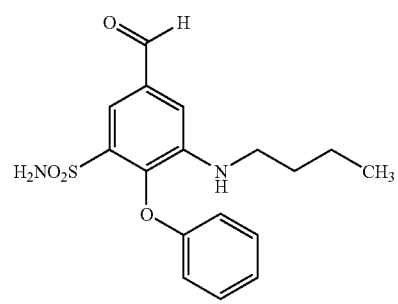

"bumetanide aldehyde"
R$_1$ = ——, R$_2$ = H
R$_3$ = O——aryl, R$_4$ = R$_5$ = H

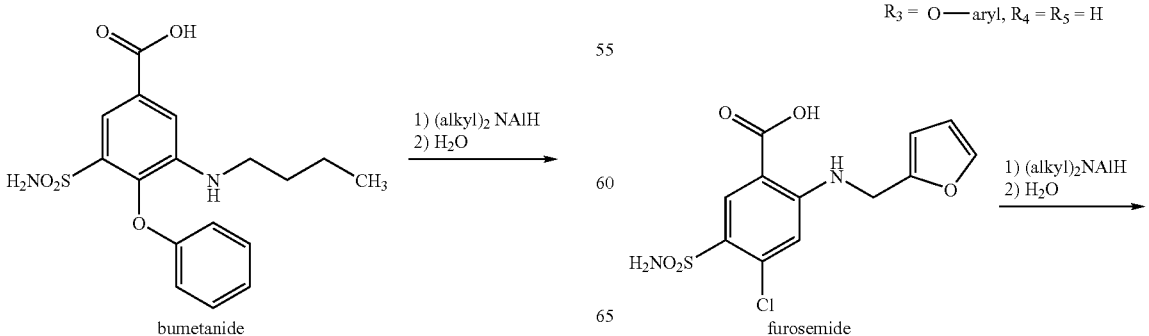

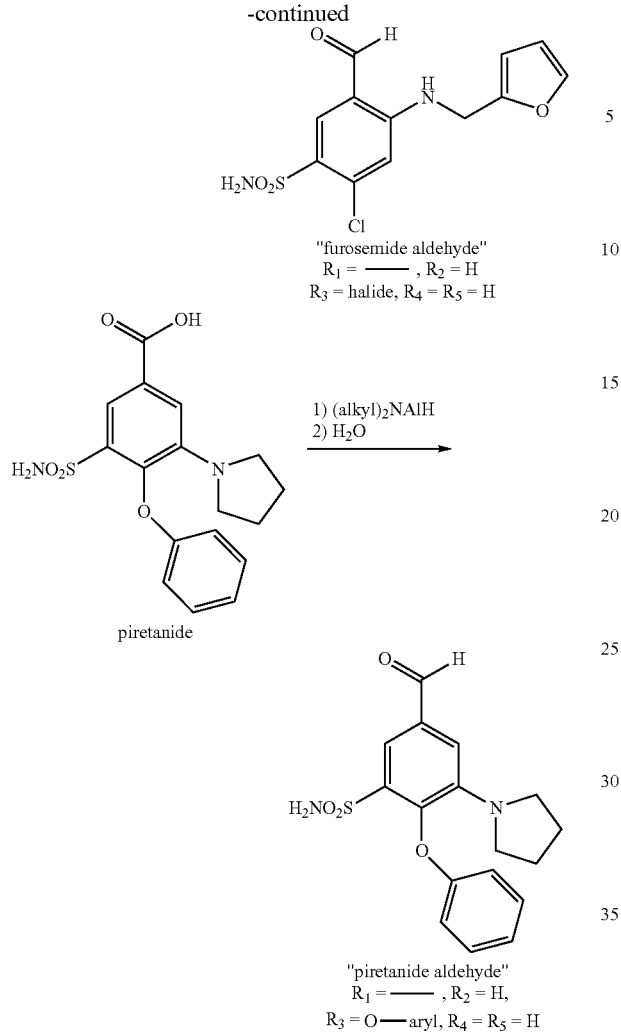
For reduction procedures used to convert benzoic acids to the corresponding benzaldehydes, see: Muraki, M. and Mukiayama, T., *Chem. Letters,* 1974, 1447; ibid, 1975, 215; Hubert, T., D., Eyman, D. P. and Wiemer, D. F., *J. Org. Chem.,* 1984, 2279.

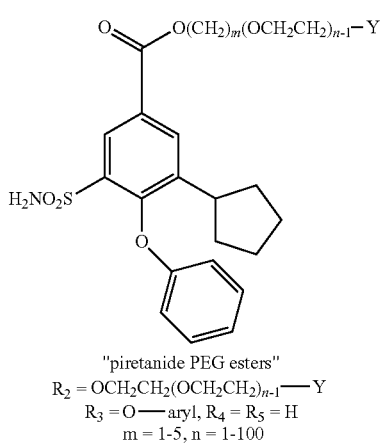

"piretanide PEG esters"
R₂ = OCH₂CH₂(OCH₂CH₂)$_{n-1}$—Y
R₃ = O—aryl, R₄ = R₅ = H
m = 1-5, n = 1-100

PEG-X is   X—(CH₂)$_m$(OCH₂CH₂)$_{n-1}$—Y, where X is halo or other leaving group (mesylate "OMs", tosylate "OTs") and Y is OH or an alcohol protecting group such as an alkyl group, an aryl group or an ester group, and where m = 1-5 and n = 1-100.

PEG-X is X—(CH₂)$_m$(OCH₂CH₂)$_{n-1}$—Y, where X is halo or other leaving group (mesylate "OMs", tosylate "OTs") and Y is OH or an alcohol protecting group such as an alkyl group, an aryl group, an acyl group or an ester group, and where m=1-5 and n=1-100.

Scheme 8. Synthesis of Exemplary Alkyl Polyethylene Glycol Ethers of Azosemide and Torsemide.

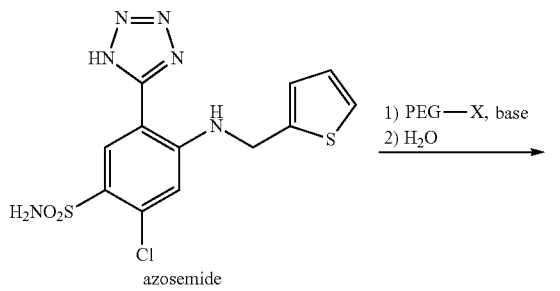

azosemide

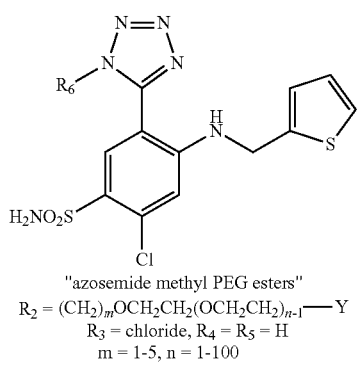

"azosemide methyl PEG esters"
R₂ = (CH₂)$_m$OCH₂CH₂(OCH₂CH₂)$_{n-1}$—Y
R₃ = chloride, R₄ = R₅ = H
m = 1-5, n = 1-100

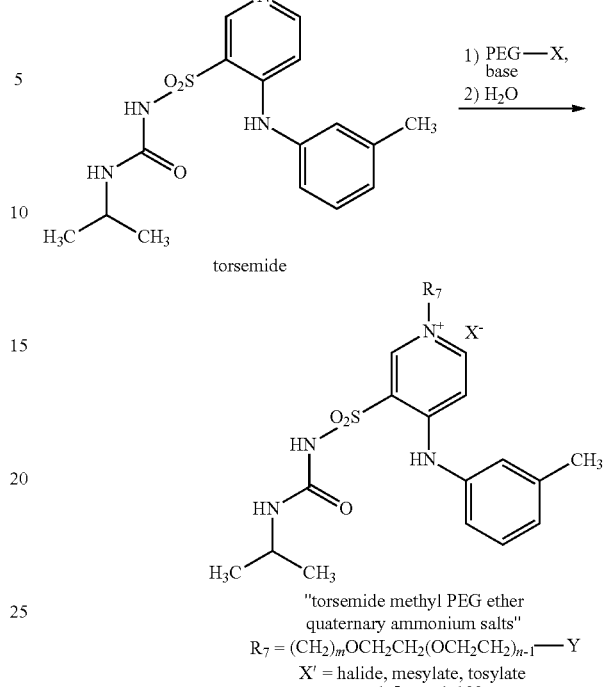

"torsemide methyl PEG ether quaternary ammonium salts"
R₇ = (CH₂)$_m$OCH₂CH₂(OCH₂CH₂)$_{n-1}$—Y
X' = halide, mesylate, tosylate
m = 1-5, n = 1-100

PEG—X is X—(CH₂)$_m$(OCH₂CH₂)$_{n-1}$—Y, where X is halo or other leaving group (mesylate "OMs", tosylate "OTs") and Y is OH or an alcohol protecting group such as an alkyl group, an aryl group, an acyl group or an ester group, and where m = 1-5 and n = 1-100.

Starting materials for synthesizing compounds of the present invention can further include compounds described in U.S. Pat. No. 3,634,583 to Feit; U.S. Pat. No. 3,806,534 to Fiet; U.S. Pat. No. 3,058,882 to Struem et al.; U.S. Pat. No. 4,010,273 to Bormann; U.S. Pat. No. 3,665,002 to Popelak; and U.S. Pat. No. 3,665,002 to Delarge, the disclosures of which are hereby incorporated by reference.

Compounds of the present invention can include isomers, tautomers, zwitterions, enantiomers, diastereomers, racemates or stereochemical mixtures thereof. The term "isomers" as used herein refers to compounds having the same number and kind of atoms, and hence the same molecular weight, but differing with respect to the arrangement or configuration of the atoms in space. Additionally, the term "isomers" includes stereoisomers and geometric isomers. The terms "stereoisomer" or "optical isomer" as used herein refer to a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structures can exist in some of the compounds of the present invention which may give rise to stereoisomerism, the invention contemplates stereoisomers and mixtures thereof. The compounds of the present invention and their salts can include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e. as individual enantiomers or diastereomers, or as stereoisomer-enriched mixtures. Tautomers are readily interconvertible constitutional isomers and there is a change in connectivity of a ligand, as in the keto and enol forms of ethyl acetoacetate. The inventive methods and compositions may employ tautomers of any of said compounds. Zwitterions are inner salts or dipolar compounds possessing acidic and basic groups in the same molecule. At neutral pH, the cation and anion of most zwitterions are equally ionized.

The present invention further provides prodrugs comprising the compounds described herein. The term "prodrug" is intended to refer to a compound that is converted under physiological conditions, by solvolysis or metabolically, to a specified compound that is pharmaceutically/pharmacologically active. The prodrug can be a compound of the present invention that has been chemically derivatized such that: (i) it retains some, all or none of the bioactivity of its parent drug compound, and (ii) it is metabolized in a subject to yield the parent drug compound. The prodrug of the present invention may also be a "partial prodrug" in that the compound has been chemically derivatized such that: (i) it retains some, all or none of the bioactivity of its parent drug compound, and (ii) it is metabolized in a subject to yield a biologically active derivative of the compound. The prodrugs can be formed utilizing a hydrolyzable coupling to the compounds described herein. A further discussion of prodrugs can be found in Ettmayer et al. *J. Med. Chem.* 47(10):2394-2404 (2004).

Prodrugs of the present invention are capable of passage across the blood-brain barrier and may undergo hydrolysis by CNS esterases to provide the active compound. Further, the prodrugs provided herein may also exhibit improved bioavailability, improved aqueous solubility, improved passive intestinal absorption, improved transporter-mediated intestinal absorption, protection against accelerated metabolism, tissue-selective delivery and/or passive enrichment in the target tissue.

Prodrugs of the present invention can include compounds according to formula I, II, III, IV and/or V described herein. Prodrugs of the present invention can further include bumetanide, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, furosemide, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide dibenzylamide, furosemide benzyltrimethyl-ammonium salt, furosemide cetyltrimethylammonium salt, furosemide N,N-dimethylglycolamide ester, furosemide pivaxetil ester, furosemide propaxetil ester, piretanide, piretanide methyl ester, piretanide cyanomethyl ester, piretanide benzyl ester, piretanide morpholinoethyl ester, piretanide 3-(dimethylaminopropyl) ester, piretanide N,N-diethylglycolamide ester, piretanide diethylamide, piretanide dibenzylamide, piretanide benzylltrimethylammonium salt, piretanide cetylltrimethylammonium salt, piretanide N,N-dimethylglycolamide ester, piretanide pivaxetil ester, piretanide propaxetil ester, tetrazolyl-substituted azosemides, pyridinium-substituted torsemide salts (also termed pyridine-substituted torsemide quaternary ammonium salts), as well as similar derivatives of indacrinone, and ozolinone. See previously presented schemes.

Moreover, as shown in the previously presented schemes, prodrugs can be formed by attachment of biocompatible polymers, such as those previously described including polyethylene glycol (PEG), to compounds of the present invention using linkages degradable under physiological conditions. See also Schacht, E. H. et al. *Poly(ethylene glycol) Chemistry and Biological Applications*, American Chemical Society, San Francisco, Calif. 297-315 (1997). Attachment of PEG to proteins can be employed to reduce immunogenicity and/or extend the half-life of the compounds provided herein. Any conventional PEGylation method can be employed, provided that the PEGylated agent retains pharmaceutical activity.

Compositions of the subject invention are suitable for human and veterinary applications and are preferably delivered as pharmaceutical compositions. Pharmaceutical compositions comprise one or more treatment agents, or a pharmaceutically acceptable salt thereof, and a physiologically acceptable carrier. A pharmaceutically acceptable salt, as used herein, refers to a salt form of a compound permitting its use or formulation as a pharmaceutical and which retains the biological effectiveness of the free acid and base of the specified compound and is not biologically or otherwise undesirable. Examples of such salts are described in *Handbook of Pharmaceutical Salts: Properties, Selection, and Use*, Wermuth, C. G. and Stahl, P. H. (eds.), Wiley-Verlag Helvetica Acta, Zürich, 2002 [ISBN 3-906390-26-8]. Examples of such salts include alkali metal salts and addition salts of free acids and bases. Examples of pharmaceutically acceptable salts, include, but are not limited to, sulfates, pyrosulfates, bisulfates, sulfites, bisulfites, phosphates, monohydrogen-phosphates, dihydrogen phosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, γ-hydroxybutyrates, glycollates, tartrates, methanesulfonates, ethane sulfonates, propanesulfonates, toluenesulfonates, naphthalene-1-sulfonates, naphthalene-2-sulfonates, and mandelates.

Pharmaceutical compositions of the present invention may also contain other compounds, which may be biologically active or inactive. For example, one or more treatment agents of the present invention may be combined with another agent, in a treatment combination, and administered according to a treatment regimen of the present invention. Such combinations may be administered as separate compositions, combined for delivery in a complementary delivery system, or formulated in a combined composition, such as a mixture or a fusion compound. Additionally, the aforementioned treatment combination may include a BBB permeability enhancer and/or a hyperosmotic agent.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like. Typical preparations for parenteral administration comprise the active ingredient with a carrier such as sterile water or parenterally acceptable oil including polyethylene glycol; polyvinyl pyrrolidone, lecithin, arachis oil or sesame oil, with other additives for aiding solubility or preservation may also be included. In the case of a solution, it can be lyophilized to a powder and then reconstituted immediately prior to use. For dispersions and suspensions, appropriate carriers and additives include aqueous gums, celluloses, silicates or oils.

The pharmaceutical compositions according to embodiments of the present invention include those suitable for oral, rectal, topical, nasal, inhalation (e.g., via an aerosol) buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used. Pharmaceutical compositions of the present invention are particularly suitable for oral, sublingual, parenteral, implantation, nasal and inhalational administration.

Compositions for injection will include the active ingredient together with suitable carriers including propylene glycol-alcohol-water, isotonic water, sterile water for injection (USP), emulPhor™-alcohol-water, cremophor-EL™ or other suitable carriers known to those skilled in the art. These carriers may be used alone or in combination with other conventional solubilizing agents such as ethanol, a glycol, or other agents known to those skilled in the art.

Where the compounds of the present invention are to be applied in the form of solutions or injections, the compounds may be used by dissolving or suspending in any conventional diluent. The diluents may include, for example, physiological-saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Compositions for nasal administration may be formulated as aerosols, drops, powders and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon.

Compositions suitable for buccal or sublingual administration include tablets, lozenges and pastilles, wherein the active ingredient is formulated with a carrier such as sugar and acacia, tragacanth or gelatin and glycerin.

Compositions for rectal administration include suppositories containing a conventional suppository base such as cocoa butter.

Compositions suitable for transdermal administration include ointments, gels and patches.

Other compositions known to those skilled in the art can also be applied for percutaneous or subcutaneous administration, such as plasters.

Further, in preparing such pharmaceutical compositions comprising the active ingredient or ingredients in admixture with components necessary for the formulation of the compositions, other conventional pharmacologically acceptable additives may be incorporated, for example, excipients, stabilizers, antiseptics, wetting agents, emulsifying agents, lubricants, sweetening agents, coloring agents, flavoring agents, isotonicity agents, buffering agents, antioxidants and the like. As the additives, there may be mentioned, for example, starch, sucrose, fructose, dextrose, lactose, glucose, mannitol, sorbitol, precipitated calcium carbonate, crystalline cellulose, carboxymethylcellulose, dextrin, gelatin, acacia, EDTA, magnesium stearate, talc, hydroxypropylmethylcellulose, sodium metabisulfite, and the like.

In further embodiments, the present invention provides kits including one or more containers comprising pharmaceutical dosage units comprising an effective amount of one or more compounds of the present invention.

When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

The compositions described herein may be administered as part of a sustained release formulation. Such formulations may generally be prepared using well-known technology and administered by, for example, oral, rectal or transdermal delivery systems, or by implantation of a formulation or therapeutic device at one or more desired target site(s). Sustained-release formulations may contain a treatment composition comprising an inventive treatment agent alone, or in combination with a second treatment agent, dispersed in a carrier matrix and/or contained within a reservoir surrounded by a rate controlling membrane. Carriers for use within such formulations are biocompatible, and may also be biodegradable. According to one embodiment, the sustained release formulation provides a relatively constant level of active composition release. According to another embodiment, the sustained release formulation is contained in a device that may be actuated by the subject or medical personnel, upon onset of certain symptoms, for example, to deliver predetermined dosages of the treatment composition. The amount of the treatment composition contained within a sustained release formulation depends upon the site of implantation, the rate and expected duration of release, and the nature of the condition to be treated or prevented.

In certain embodiments, compositions of the present invention for treatment of neuropathic pain and neuropsychiatric disorders are administered using a formulation and a route of administration that facilitates delivery of the treatment composition(s) to the central nervous system. Treatment compositions, such as NKCC1 antagonists, may be formulated to facilitate crossing of the blood brain barrier as described above, or may be co-administered with an agent that crosses the blood brain barrier. Treatment compositions may be delivered in liposome formulations, for example, that cross the blood brain barrier, or may be co-administered with other compounds, such as bradykinins, bradykinin analogs or derivatives, or other compounds, such as SERAPORT™, that cross the blood brain barrier. Alternatively, treatment compositions of the present invention may be delivered using a spinal tap that places the treatment composition directly in the circulating cerebrospinal fluid. For some treatment conditions, there may be transient or permanent breakdowns of the blood brain barrier and specialized formulation of the treatment composition to cross the blood brain barrier may not be necessary. We have determined, for example, that a bolus iv injection of 20 mg furosemide reduces or abolishes both spontaneous interictal activity and electrical stimulation-evoked epileptiform activity in human patients who are refractory to antiepileptic drugs (AEDs) (Haglund & Hochman *J. Neurophysiol.* (Feb. 23, 2005) doi:10.1152/jn.00944.2004).

Routes and frequency of administration of the therapeutic compositions disclosed herein, as well as dosages, vary according to the indication, and from individual to individual, and may be readily determined by a physician from information that is generally available, and by monitoring patients and adjusting the dosages and treatment regimen accordingly using standard techniques. In general, appropriate dosages and treatment regimen provide the active composition(s) in an amount sufficient to provide therapeutic and/or prophylactic benefit. Dosages and treatment regimen may be established by monitoring improved clinical outcomes in treated patients as compared to non-treated patients.

The term "effective amount" or "effective" is intended to designate a dose that causes a relief of symptoms of a disease or disorder as noted through clinical testing and evaluation, patient observation, and/or the like. "Effective amount" or "effective" further can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. Therapeutically effective dosages and treatment regimen will depend on the condition, the severity of the condition, and the general state of the patient being treated. Since the pharmacokinetics and pharmacodynamics of the treatment compositions of the present invention vary in different patients, a preferred method for determining a therapeutically effective dosage in a patient is to gradually escalate the dosage and monitor the clinical and laboratory indicia. For combination therapy, the two or more agents are coadministered such that each of the agents is present in a therapeutically effective amount for sufficient time to produce a therapeutic or prophylactic effect. The term "coadministration" is intended to encompass simultaneous or sequential administration of two or more agents in the same formulation or unit dosage form or in separate formulations. Appropriate dosages and treatment regimen for treatment of acute episodic conditions, chronic conditions, or prophylaxis will necessarily vary to accommodate the condition of the patient.

By way of example, for the treatment to neuropathic pain, furosemide may be administered orally to a patient in amounts of 10-40 mg at a frequency of 1-3 times per day, preferably in an amount of 40 mg three times per day. In an alternative example, bumetanide may be administered orally for the treatment of neuropathic pain in amounts of 1-10 mg at a frequency of 1-3 times per day. One of skill in the art will appreciate that smaller doses may be employed, for example, in pediatric applications.

In further embodiments, bumetanide analogs according to the present invention may be administered in amounts of 1.5 to 6 mg daily, for example 1 tablet or capsule three times a day. In some embodiments, furosemide analogs according to the present invention may be administered in amounts of 60 to 240 mg/day, for example 1 tablet or capsule three times a day. In other embodiments, piretanide analogs according to the present invention may be administered in amounts of 10 to 20 mg daily, for example 1 tablet or capsule once a day. In some embodiments, azosemide analogs according to the present invention may be administered in an amount of 60 mg per day.

In other embodiments, torsemide analogs according to the present invention may be administered in amounts of 10 to 20 mg daily, for example 1 tablet or capsule once a day. It should be noted that lower doses may be administered, particularly for IV administration.

Methods and systems of the present invention may also be used to evaluate candidate compounds and treatment regimen for the treatment and/or prophylaxis of neuropathic pain and neuropsychiatric disorders. Various techniques for generating candidate compounds potentially having the desired NKCC1 cotransporter antagonist activity may be employed. Candidate compounds may be generated using procedures well known to those skilled in the art of synthetic organic chemistry. Structure-activity relationships and molecular modeling techniques are useful for the purpose of modifying known NKCC1 antagonists, such furosemide, bumetanide, ethacrinic acid and related compounds, to confer the desired activities and specificities. Methods for screening candidate compounds for desired activities are described in U.S. Pat. Nos. 5,902,732, 5,976,825, 6,096,510 and 6,319,682, which are incorporated herein by reference in their entireties.

Candidate compounds may be screened for NKCC1 antagonist activity using screening methods of the present invention with various types of cells in culture such as glial cells, neuronal cells, renal cells, and the like, or in situ in animal models. Screening techniques to identify chloride cotransporter antagonist activity, for example, may involve altering the ionic balance of the extracellular space in the tissue culture sample, or in situ in an animal model, by producing a higher than "normal" anionic chloride concentration. The geometrical and/or optical properties of the cell or tissue sample subject to this altered ionic balance are determined, and candidate agents are administered. Following administration of the candidate agents, the corresponding geometrical and/or optical properties of the cell or tissue sample are monitored to determine whether the ionic imbalance remains, or whether the cells responded by altering the ionic balances in the extracellular and intracellular space. If the ionic imbalance remains, the candidate agent is likely a chloride cotransporter antagonist. By screening using various types of cells or tissues, candidate compounds having a high level of glial cell chloride cotransporter antagonist activity and having a reduced level of neuronal cell and renal cell chloride cotransporter antagonist activity may be identified. Similarly, effects on different types of cells and tissue systems may be assessed.

Additionally, the efficacy of candidate compounds may be assessed by simulating or inducing a condition, such as neuropathic pain, in situ in an animal model, monitoring the geometrical and/or optical properties of the cell or tissue sample during stimulation of the condition, administering the candidate compound, then monitoring the geometrical and/or optical properties of the cell or tissue sample following administration of the candidate compound, and comparing the geometrical and/or optical properties of the cell or tissue sample to determine the effect of the candidate compound. Testing the efficacy of treatment compositions for relief of neuropathic pain can be carried using well known methods and animal models, such as that described in Bennett, *Hosp. Pract.* (Off Ed). 33:95-98, 1998.

As discussed above, compositions for use in the inventive methods may comprise a treatment agent selected from the group consisting of: antibodies, or antigen-binding fragments thereof, that specifically bind to NKCC1; soluble ligands that bind to NKCC1; anti-sense oligonucleotides to NKCC1; and small interfering RNA molecules (siRNA or RNAi) that are specific for NKCC1.

Antibodies that specifically bind to NKCC1 are known in the art and include those available from Alpha Diagnostic International, Inc. (San Antonio, Tex. 78238). An "antigen-binding site," or "antigen-binding fragment" of an antibody refers to the part of the antibody that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A number of molecules are known in the art that comprise antigen-binding sites capable of exhibiting the binding properties of an antibody molecule. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment, which comprises both antigen-binding sites. An "Fv" fragment can be produced by preferential proteolytic cleavage of an IgM, IgG or IgA immunoglobulin molecule, but are more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Inbar et al. *Proc. Natl. Acad. Sci. USA* 69:2659-2662, 1972; Hochman et al. *Biochem* 15:2706-2710, 1976; and Ehrlich et al. *Biochem* 19:4091-4096, 1980).

Humanized antibodies that specifically bind to NKCC1 may also be employed in the inventive methods. A number of humanized antibody molecules comprising an antigen-binding site derived from a non-human immunoglobulin have been described, including chimeric antibodies having rodent V regions and their associated CDRs fused to human constant domains (Winter et al. *Nature* 349:293-299, 1991; Lobuglio et al. *Proc. Natl. Acad. Sci. USA* 86:4220-4224, 1989; Shaw et al. *J Immunol.* 138:4534-4538, 1987; and Brown et al. *Cancer Res.* 47:3577-3583, 1987); rodent CDRs grafted into a human supporting FR prior to fusion with an appropriate human antibody constant domain (Riechmann et al. *Nature* 332:323-327, 1988; Verhoeyen et al. *Science* 239:1534-1536, 1988; and Jones et al. *Nature* 321:522-525, 1986); and rodent CDRs supported by recombinantly veneered rodent FRs (European Patent Publication No. 519,596, published Dec. 23, 1992). These "humanized" molecules are designed to minimize unwanted immunological responses towards rodent antihuman antibody molecules which limit the duration and effectiveness of therapeutic applications of those moieties in human recipients.

Modulating the activity of NKCC1 may alternatively be accomplished by reducing or inhibiting expression of the polypeptide, which can be achieved by interfering with transcription and/or translation of the corresponding polynucleotide. Polypeptide expression may be inhibited, for example, by introducing anti-sense expression vectors, anti-sense oligodeoxyribonucleotides, anti-sense phosphorothioate oligodeoxy-ribonucleotides, anti-sense oligoribonucleotides or anti-sense phosphorothioate oligoribonucleotides; or by other means well known in the art. All such anti-sense polynucleotides are referred to collectively herein as "anti-sense oligonucleotides".

The anti-sense oligonucleotides for use in the inventive methods are sufficiently complementary to the NKCC1 polynucleotide to bind specifically to the polynucleotide. The sequence of an anti-sense oligonucleotide need not be 100% complementary to the of the polynucleotide in order for the anti-sense oligonucleotide to be effective in the inventive methods. Rather an anti-sense oligonucleotide is sufficiently complementary when binding of the anti-sense oligonucleotide to the polynucleotide interferes with the normal function of the polynucleotide to cause a loss of utility, and when non-specific binding of the oligonucleotide to other, non-target sequences is avoided. The design of appropriate anti-sense oligonucleotides is well known in the art. Oligonucleotides that are complementary to the 5' end of the message, for example the 5' untranslated sequence up to and including the AUG initiation codon, should work most efficiently at inhibiting translation. However, oligonucleotides complementary to either the 5'- or 3'-non-translated, non-coding, regions of the targeted polynucleotide may also be employed. Cell permeation and activity of anti-sense oligonucleotides can be enhanced by appropriate chemical modifications, such as the use of phenoxazine-substituted C-5 propynyl uracil oligonucleotides (Flanagan et al., *Nat. Biotechnol.* 17:48-52, 1999) or 2'-O-(2-methoxy) ethyl (2'-MOE)-oligonucleotides (Zhang et al., *Nat. Biotechnol.* 18:862-867, 2000). The use of techniques involving anti-sense oligonucleotides is well known in the art and is described, for example, in Robinson-Benion et al. (*Methods in Enzymol.* 254:363-375, 1995) and Kawasaki et al. (*Artific. Organs* 20:836-848, 1996).

Expression of the NKCC1 polypeptide may also be specifically suppressed by methods such as RNA interference (RNAi). A review of this technique is found in *Science,* 288: 1370-1372, 2000. Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAI also operates on a post-translational level and is sequence specific, but suppresses gene expression far more efficiently. Exemplary methods for controlling or modifying gene expression are provided in WO 99/49029, WO 99/53050 and WO01/75164, the disclosures of which are hereby incorporated by reference. In these methods, post-transcriptional gene silencing is brought about by a sequence-specific RNA degradation process which results in the rapid degradation of transcripts of sequence-related genes. Studies have shown that double-stranded RNA may act as a mediator of sequence-specific gene silencing (see, for example, Montgomery and Fire, *Trends in Genetics,* 14:255-258, 1998). Gene constructs that produce transcripts with self-complementary regions are particularly efficient at gene silencing.

It has been demonstrated that one or more ribonucleases specifically bind to and cleave double-stranded RNA into short fragments. The ribonuclease(s) remains associated with these fragments, which in turn specifically bind to complementary mRNA, i.e. specifically bind to the transcribed mRNA strand for the gene of interest. The mRNA for the gene is also degraded by the ribonuclease(s) into short fragments, thereby obviating translation and expression of the gene. Additionally, an RNA-polymerase may act to facilitate the synthesis of numerous copies of the short fragments, which exponentially increases the efficiency of the system. A unique feature of RNAi is that silencing is not limited to the cells where it is initiated. The gene-silencing effects may be disseminated to other parts of an organism.

The NKCC1 polynucleotide may thus be employed to generate gene silencing constructs and/or gene-specific self-complementary, double-stranded RNA sequences that can be employed in the inventive methods using delivery methods known in the art. A gene construct may be employed to express the self-complementary RNA sequences. Alternatively, cells may be contacted with gene-specific double-stranded RNA molecules, such that the RNA molecules are internalized into the cell cytoplasm to exert a gene silencing effect. The double-stranded RNA must have sufficient homology to the NKCC1 gene to mediate RNAi without affecting expression of non-target genes. The double-stranded DNA is at least 20 nucleotides in length, and is preferably 21-23 nucleotides in length. Preferably, the double-stranded RNA corresponds specifically to a polynucleotide of the present invention. The use of small interfering RNA (siRNA) molecules of 21-23 nucleotides in length to suppress gene expression in mammalian cells is described in WO 01/75164. Tools for designing optimal inhibitory siRNAs include that available from DNAengine Inc. (Seattle, Wash.).

One RNAi technique employs genetic constructs within which sense and anti-sense sequences are placed in regions flanking an intron sequence in proper splicing orientation with donor and acceptor splicing sites. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes.

For in vivo uses, a genetic construct, anti-sense oligonucleotide or RNA molecule may be administered by various art-recognized procedures (see, e.g., Rolland, *Crit. Rev. Therap. Drug Carrier Systems* 15:143-198, 1998, and cited references). Both viral and non-viral delivery methods have been used for gene therapy. Useful viral vectors include, for example, adenovirus, adeno-associated virus (AAV), retrovirus, vaccinia virus and avian poxvirus. Improvements have been made in the efficiency of targeting genes to tumor cells with adenoviral vectors, for example, by coupling adenovirus to DNA-polylysine complexes and by strategies that exploit receptor-mediated endocytosis for selective targeting (see, e.g., Curiel et al., *Hum. Gene Ther.*, 3:147-154, 1992; and Cristiano & Curiel, *Cancer Gene Ther.* 3:49-57, 1996). Non-viral methods for delivering polynucleotides are reviewed in Chang & Seymour, (Eds) *Curr. Opin. Mol. Ther.*, vol. 2, 2000. These methods include contacting cells with naked DNA, cationic liposomes, or polyplexes of polynucleotides with cationic polymers and dendrimers for systemic administration (Chang & Seymour, Ibid.). Liposomes can be modified by incorporation of ligands that recognize cell-surface receptors and allow targeting to specific receptors for uptake by receptor-mediated endocytosis (see, for example, Xu et al., *Mol. Genet. Metab.*, 64:193-197; 1998; and Xu et al., *Hum. Gene Ther.*, 10:2941-2952, 1999).

Tumor-targeting bacteria, such as *Salmonella*, are potentially useful for delivering genes to tumors following systemic administration (Low et al., *Nat. Biotechnol.* 17:37-41, 1999). Bacteria can be engineered ex vivo to penetrate and to deliver DNA with high efficiency into, for example, mammalian epithelial cells in vivo (see, e.g., Grillot-Courvalin et al., *Nat. Biotechnol.* 16:862-866, 1998). Degradation-stabilized oligonucleotides may be encapsulated into liposomes and delivered to patients by injection either intravenously or directly into a target site (for example, the origin of neuropathic pain). Alternatively, retroviral or adenoviral vectors, or naked DNA expressing anti-sense RNA for the inventive polypeptides, may be administered to patients. Suitable techniques for use in such methods are well known in the art.

The treatment compositions and methods of the present invention have been described, above, with respect to certain preferred embodiments. The Examples set forth below describe the results of specific experiments and are not intended to limit the invention in any fashion.

Example 1

Methyl 3-Aminosulfonyl-5-butylamino-4-phenoxybenzoate (Bumetanide Methyl Ester)

To a slurry of bumetanide (1.2 g, 3.29 mmol) in methanol (12 mL) under nitrogen, was added a mixture of thionyl chloride (70 uL) in methanol (6 mL) over 5 minutes. After stirring for 5 minutes the reaction mixture became soluble. The reaction was stirred for an additional 30 minutes, at which time the reaction was complete as determined by thin layer chromatography (TLC). The methanol was removed under reduced pressure and the residue was brought up in ethyl acetate and washed with saturated sodium bicarbonate, water and brine. The ethyl acetate was dried over anhydrous magnesium sulfate and concentrated to yield 1.1 g (89%) of methyl 3-aminosulfonyl-5-butylamino-4-phenoxybenzoate as a white solid.

Example 2

Cyanomethyl 3-Aminosulfonyl-5-butylamino-4-phenoxybenzoate (Bumetanide Cyanomethyl Ester)

Bumetanide (1.0 g, 2.7 mmol) was dissolved in dimethylformamide (DMF) and chloroacetonitrile (195 uL, 2.7 mmol) was added followed by triethylamine (465 uL). The reaction was heated to 100° C. for 12 hours, at which time TLC and liquid chromatography-coupled mass spectrometry (LC/MS) indicated the reaction was complete. The reaction was cooled to room temperature, brought up in dichloromethane and washed with water, saturated with ammonium chloride and reduced to a slurry. To the slurry was added water (25 mL) and crude product precipitated as an off white solid. Pure cyanomethyl 3-3minosulfonyl-5-butylamino-4-phenoxybenzoate (850 mg) was obtained via recrystallization in acetonitrile.

Example 3

Benzyl 3-Aminosulfonyl-5-butylamino-4-phenoxybenzoate (Bumetanide Benzyl Ester)

Bumetanide (1.15 g, 3.15 mmol) was dissolved in dimethylformamide (DMF, 10 mL) and benzyl chloride (400 uL, 2.8 mmol) was added followed by triethylamine (480 uL). The reaction was heated to 80° C. for 12 hours, at which time TLC and LC/MS indicated the reaction was complete. The reaction was cooled to room temperature, brought up in dichloromethane and washed with water, saturated ammonium chloride and concentrated to a thick slurry. To the slurry was added water (25 mL). The resultant solids were filtered and dried in a vacuum oven at 50° C. for 12 hours to yield 1.0 g (80%) of benzyl 3-aminosulfonyl-5-butylamino-4-phenoxybenzoate.

Example 4

2-(4-Morpholino)ethyl 3-Aminosulfonyl-5-butylamino-4-phenoxybenzoate (Bumetanide Morpholinoethyl Ester)

Bumetanide (1.2 g, 3.29 mmol) was dissolved in dimethylformamide (DMF, 12 mL) and 4-(2-chloroethyl)morpholine hydrochloride (675 mg, 3.62 mmol) was added followed by triethylamine (1 mL) and sodium iodide (500 mg 3.33 mmol). The reaction was heated to 95° C. for 8 hours, at which time TLC and LC/MS indicated the reaction was complete. The reaction was cooled to room temperature brought up in dichloromethane and washed with water, saturated ammonium chloride and concentrated to dryness. After purification via biotage flash chromatography, the purified elute, on evaporation under vacuum, yielded 2-(4-morpholino) ethyl 3-aminosulfonyl-5-butylamino-4-phenoxybenzoate as a white solid (600 mg, 62%).

Example 5

3-(N,N-Dimethylaminopropyl) 3-Aminosulfonyl-5-butylamino-4-phenoxybenzoate [Bumetanide 3-(Dimethylaminopropyl)Ester]

In a similar manner to Example 31, bumetanide can be reacted with 3-(dimethylamino)propyl chloride hydrochloride, triethylamine and sodium iodide in dimethylformamide (DMF) to yield 3-(N,N-dimethylaminopropyl) 3-aminosulfonyl-5-butylamino-4-phenoxybenzoate.

Example 6

N,N-Diethylaminocarbonylmethyl 3-Aminosulfonyl-5-butylamino-4-phenoxybenzoate (Bumetanide N,N-Diethyllycolamide Ester)

Bumetanide (1.2 g, 3.29 mmol) was dissolved in dimethylformamide (12 mL) and 2-chloro-N,N-diethylacetamide (500 mg, 3.35 mmol) was added followed by triethylamine (0.68 mL) and sodium iodide (500 mg 3.33 mmol). The reaction was heated to 95° C. for 8 hours, at which time TLC and LC/MS indicated the reaction was complete. The reaction was cooled to room temperature brought up in dichloromethane and washed with water, saturated ammonium chloride and reduced to a thick slurry. To the slurry was added water (25 mL), and the resultant solids precipitated from the solution. The product was filtered and dried in a vacuum oven at 50° C. for 12 hours to yield 1.0 g of N,N-diethylaminocarbonylmethyl 3-aminosulfonyl-5-butylamino-4-phenoxybenzoate.

Example 7

N,N-Diethyl 3-Aminosulfonyl-5-butylamino-4-phenoxybenzamide (Bumetanide Diethylamide)

Bumetanide (1.16 g, 3.2 mmol) was dissolved in dichloromethane (10 mL) and 1-ethyl-3-(3-dimethylaminopropyl) carbodiimide (EDC, 690 mg, 3.6 mmol) was added. After 5 minutes N-hydroxybenzotriazole (HOBt, 498 mg, 3.6 mmol) was added and the solution was stirred for an additional 5 minutes. Diethylamine (332 uL, 3.2 mmol) was added and the reaction was stirred for 2 hours. The reaction was washed with saturated sodium bicarbonate, water and brine, and dried with magnesium sulfate. The dichloromethane was removed under reduced pressure to yield 860 mg (65%) of pure N,N-diethyl 3-aminosulfonyl-5-butylamino-4-phenoxybenzamide.

Example 8

N,N-Dibenzyl 3-Aminosulfonyl-5-butylamino-4-phenoxybenzamide (Bumetanide Dibenzylamide)

Bumetanide (960 mg, 2.6 mmol) was dissolved in dimethyiformamide (DMF, 10 mL) and 1-ethyl-3-(3-dimethylaminopropyl)carbodiimide (EDC, 560 mg, 3.6 mmol) was added. After 10 minutes 1-hydroxybenzotriazole (HOBt, 392 mg, 2.9 mmol) was added and the solution was stirred for an additional 10 minutes. Dibenzylamine (1 mL, 5.2 mmol) was added and the reaction was stirred for 2 hours, at which time the reaction was complete by LC/MS. The reaction was poured into saturated ammonium chloride (20 mL) and extracted with ethyl acetate (2×100 mL). The ethyl acetate, was washed with saturated sodium bicarbonate, water and brine, and dried over anhydrous magnesium sulfate. The ethyl acetate was removed under reduced pressure to yield 1.0 g (75%) of N,N-dibenzyl 3-aminosulfonyl-5-butylamino-4-phenoxybenzamide as white solid.

Example 9

Benzyltrimethylammonium 3-Aminosulfonyl-5-butylamino-4-phenoxybenzoate (Bumetanide Benzylltrimethylammonium Salt)

To a solution of benzyltrimethylammonium hydroxide (451 mg, 2.7 mmol) in water (1 mL) was added bumetanide (1 g, 2.7 mmol) over a period of 5 minutes. The reaction mixture became clear after 10 minutes of stirring. The water was removed under reduced pressure to yield a crude colorless oil. Pure product was obtained from recrystallization of the oil with water and heptane to yield 690 mg of benzyltrimethylammonium 3-aminosulfonyl-5-butylamino-4-phenoxybenzoate as light pink crystals.

Example 10

Cetyltrimethylammonium 3-Aminosulfonyl-5-butylamino-4-phenoxybenzoate (Bumetanide Cetylltrimethylammonium Salt)

In a similar manner to Example 9, bumetanide can be reacted with cetyltrimethylammonium hydroxide in water to yield cetyltrimethylammonium 3-aminosulfonyl-5-butylamino-4-phenoxybenzoate.

Example 11

N,N-Dimethylaminocarbonylmethyl 3-Aminosulfonyl-5-butylamino-4-phenoxybenzoate (Bumetanide N,N-Dimethylglycolamide Ester)

Bumetanide (1.2 g, 3.29 mmol) was dissolved in dimethylformamide (DMF, 10 mL) and 2-chloro-N,N-dimethylamide (410 uL, 3.9 mmol) was added, followed by triethylamine (0.70 mL) and sodium iodide (545 mg, 3.6 mmol). The reaction was heated to 50° C. for 10 hours, at which time TLC and LC/MS indicated the reaction was complete. The solvent was removed under reduced pressure and the residue was dissolved in ethyl acetate and washed with saturated sodium bicarbonate, water and brine, and dried over anhydrous magnesium sulfate. The ethyl acetate was removed under reduced pressure and the product was purified via flash chromatography to yield 685 mg (60%) of pure N,N-dimethylaminocarbonylmethyl 3-aminosulfonyl-5-butylamino-4-phenoxybenzoate.

Example 12 t-Butylcarbonyloxymethyl 3-Aminosulfonyl-5-butylamino-4-phenoxybenzoate (Bumetanide Pivaxetil Ester)

Bumetanide (1.2 g, 3.29 mmol) was dissolved in dimethylformamide (DMF, 10 mL) and chloromethyl pivalate (575 uL, 3.9 mmol) was added followed by triethylamine (0.70 mL) and sodium iodide (545 mg, 3.6 mmol). The reaction was heated to 50° C. for 10 hours, at which time TLC and LC/MS indicated the reaction was complete. The solvent was removed under reduced pressure and the residue was dissolved in ethyl acetate and washed with saturated sodium bicarbonate, water and brine, and dried over anhydrous magnesium sulfate. The ethyl acetate was removed under reduced pressure and the product was purified via flash chromatography to yield 653 mg (60%) of pure t-butylcarbonyloxymethyl 3-aminosulfonyl-5-butylamino-4-phenoxybenzoate.

Example 13

Ethylcarbonyloxymethyl 3-Aminosulfonyl-5-butylamino-4-phenoxybenzoate (Bumetanide Propaxetil Ester)

In a similar manner to Example 12, bumetanide can be reacted with chloromethyl propionate, triethylamine and sodium iodide in dimethylformamide (DMF) to yield ethylcarbonyloxymethyl 3-aminosulfonyl-5-butylamino-4-phenoxybenzoate.

Example 14

Methyl 3-Aminosulfonyl-4-phenoxy-5-(1-pyrrolidinyl)benzoate (Piretanide Methyl Ester)

In a similar manner to Example 1, piretanide can be reacted with thionyl chloride and methanol to yield methyl 3-aminosulfonyl-4-phenoxy-5-(1-pyrrolidinyl)benzoate.

Example 15

Cyanomethyl 3-Aminosulfonyl-4-phenoxy-5-(1-pyrrolidinyl)benzoate (Piretanide Cyanomethyl Ester)

In a similar manner to Example 2, piretanide can be reacted with chloroacetonitrile in DMF to yield cyanomethyl 3-aminosulfonyl-4-phenoxy-5-(1-pyrrolidinyl)benzoate.

Example 16

Benzyl 3-Aminosulfonyl-4-phenoxy-5-(1-pyrrolidinyl)benzoate (Piretanide Benzyl Ester)

In a similar manner to Example 3, piretanide can be reacted with benzyl chloride in DMF to yield benzyl 3-aminosulfonyl-4-phenoxy-5-(1-pyrrolidinyl)benzoate.

Example 17

2-(4-Morpholino)ethyl 3-Aminosulfonyl-4-phenoxy-5-(1-pyrrolidinyl)benzoate (Piretanide Morpholinoethyl Ester)

In a similar manner to Example 4, piretanide can be reacted with 4-(2-chloroethyl)morpholine hydrochloride, triethylamine and sodium iodide in DMF to yield 2-(4-morpholino) ethyl 3-aminosulfonyl-4-phenoxy-5-(1-pyrrolidinyl)benzoate.

Example 18

3-(N,N-Dimethylaminopropyl 3-Aminosulfonyl-4-phenoxy-5-(1-pyrrolidinyl)benzoate [Piretanide 3-(Dimethylaminopropyl)Ester]

In a similar manner to Example 31, piretanide can be reacted with 3-(dimethylamino)propyl chloride hydrochloride, triethylamine and sodium iodide in dimethylformamide (DMF) to yield 3-(N,N-dimethylaminopropyl 3-aminosulfonyl-4-phenoxy-5-(1-pyrrolidinyl)benzoate.

Example 19

N,N-Diethylaminocarbonylmethyl 3-Aminosulfonyl-4-phenoxy-5-(1-pyrrolidinyl)benzoate (Piretanide N,N-Diethylglycolamide Ester)

In a similar manner to Example 6, piretanide can be reacted with 2-chloro-N,N-diethylacetamide, triethylamine and sodium iodide in dimethylformamide (DMF) to yield N,N-diethylaminocarbonylmethyl 3-aminosulfonyl-4-phenoxy-5-(1-pyrrolidinyl)benzoate.

Example 20

N,N-Diethyl 3-Aminosulfonyl-4-phenoxy-5-(1-pyrrolidinyl)benzoate (Piretanide Diethylamide)

In a similar manner to Example 7, piretanide can be reacted with EDC, HOBt and diethylamine in DMF to yield N,N-diethyl 3-aminosulfonyl-4-phenoxy-5-(1-pyrrolidinyl)-benzamide.

Example 21

N,N-Dibenzyl 3-Aminosulfonyl-4-phenoxy-5-(1-pyrrolidinyl)benzoate (Piretanide Dibenzylamide)

In a similar manner to Example 8, piretanide can be reacted with EDC, HOBt and dibenzylamine in DMF to yield N,N-dibenzyl 3-aminosulfonyl-4-phenoxy-5-(1-pyrrolidinyl) benzamide.

Example 22

Benzyltrimethylammonium 3-Aminosulfonyl-4-phenoxy-5-(1-pyrrolidinyl)benzoate (Piretanide Benzyltrimethylammonium Salt)

In a similar manner to Example 9, piretanide can be reacted with benzyltrimethylammonium hydroxide to yield benzyltrimethylammonium 3-aminosulfonyl-4-phenoxy-5-(1-pyrrolidinyl)benzoate.

Example 23

Cetyltrimethylammonium 3-Aminosulfonyl-4-phenoxy-5-(1-pyrrolidinyl)benzoate (Piretanide Cetyltrimethylammonium Salt)

In a similar manner to Example 10, piretanide can be reacted with cetyltrimethylammonium hydroxide in water to yield cetyltrimethylammonium 3-aminosulfonyl-4-phenoxy-5-(1-pyrrolidinyl)benzoate.

Example 24

N,N-Dimethylaminocarbonylmethyl 3-Aminosulfonyl-4-phenoxy-5-(1-pyrrolidinyl)-benzoate (Piretanide N,N-Dimethylglycolamide Ester)

In a similar manner to Example 11, piretanide can be reacted with 2-chloro-N,N dimethylacetamide, triethylamine and sodium iodide in DMF to yield N,N-dimethylaminocarbonylmethyl 3-aminosulfonyl-4-phenoxy-5-(1-pyrrolidinyl)benzoate.

Example 25 t-Butylcarbonyloxymethyl 3-Aminosulfonyl-4-phenoxy-5-(1-pyrrolidinyl)benzoate (Piretanide Pivaxetil Ester)

In a similar manner to Example 12, piretanide can be reacted with chloromethyl pivalate, triethylamine and sodium iodide in DMF to yield_t-butylcarbonyloxymethyl 3-aminosulfonyl-4-phenoxy-5-(1-pyrrolidinyl)benzoate.

Example 26

Ethylcarbonyloxymethyl 3-Aminosulfonyl-4-phenoxy-5-(1-pyrrolidinyl)benzoate (Piretanide Propaxetil Ester)

In a similar manner to Example 13, piretanide can be reacted with chloromethyl propionate, triethylamine and sodium iodide in DMF to yield ethylcarbonyloxymethyl 3-aminosulfonyl-4-phenoxy-5-(1-pyrrolidinyl)benzoate.

Example 27

Ethyl 5-Aminosulfonyl4-chloro-2-[(2-furanylmethyl)amino]benzoate (Furosemide Ethyl Ester)

The method of Bundgaard, H., Norgaard, T. and Nielsen, N. M., *Int. J. Pharmaceutics,* 1988, 42, 217-224, can be employed to prepare ethyl 5-aminosulfonyl-4-chloro-2-[(2-furanylmethyl)amino]benzoate, m.p. 163-1650.

Example 28

Cyanomethyl 5-Aminosulfonyl-4-chloro-2-[(2-furanylmethyl)amino]benzoate (Furosemide Cyanomethyl Ester)

In a similar manner to Example 2, furosemide can be reacted with chloroacetonitrile in DMF to yield cyanomethyl 5-aminosulfonyl-4-chloro-2-[(2-furanylmethyl)amino]-benzoate.

Example 29

Benzyl 5-Aminosulfonyl-4-chloro-2-[(2-furanylmethyl)amino]benzoate (Furosemide Benzyl Ester)

In a similar manner to Example 3, furosemide can be reacted with benzyl chloride in DMF to yield benzyl 5-aminosulfonyl-4-chloro-2-[(2-furanylmethyl)amino]benzoate.

Example 30

2-(4-Morpholino)ethyl 5-Aminosulfonyl-4-chloro-2-[(2-furanylmethyl)amino]benzoate (Furosemide Morpholinoethyl Ester)

The method of Mork, N., Bundgaard, H., Shalmi, M. and Christensen, S., *Int. J. Pharmaceutics,* 1990, 60, 163-169, can be employed to prepare 2-(4-morpholino)ethyl 5-aminosulfonyl-4-chloro-2-[(2-furanylmethyl)amino]benzoate, m.p. 134-135°.

Example 31

3-(N,N-Dimethylaminopropyl 5-Aminosulfonyl-4-chloro-2-[(2-furanylmethyl)amino]benzoate (Furosemide 3-(Dimethylaminopropyl) Ester)

The method of Mork, N., Bundgaard, H., Shalmi, M. and Christensen, S., *Int. J. Pharmaceutics,* 1990, 60, 163-169, can be employed to prepare 3-(N,N-dimethylaminopropyl 5-aminosulfonyl-4-chloro-2-[(2-furanylmethyl)amino]benzoate, m.p. 212-213°.

Example 32

N,N-Diethylaminocarbonylmethyl 5-Aminosulfonyl-4-chloro-2-[(2-furanylmethyl)amino]benzoate (Furosemide N,N-Diethylglycolamide Ester)

The method of Mork, N., Bundgaard, H., Shalmi, M. and Christensen, S., *Int. J. Pharmaceutics,* 1990, 60, 163-169, can be employed to prepare N,N-diethyl-aminocarbonylmethyl 5-aminosulfonyl-4-chloro-2-[(2-furanylmethyl)amino]benzoate, m.p. 135-136°.

Example 33

N,N-Diethyl 5-Aminosulfonyl-4-chloro-2-[(2-furanylmethyl)amino]benzamide (Furosemide Diethylamide)

In a similar manner to Example 7, furosemide can be reacted with EDC, HOBt and diethylamine in DMF to yield N,N-diethyl 5-aminosulfonyl-4-chloro-2-[(2-furanylmethyl)-amino]benzamide.

Example 34

N,N-Dibenzyl 5-Aminosulfonyl-4-chloro-2-[(2-furanylmethyl)amino]benzamide (Furosemide Dibenzylamide)

In similar manner to Example 8, furosemide can be reacted with EDC, HOBt and dibenzylamine in DMF to yield N,N-dibenzyl 5-aminosulfonyl-4-chloro-2-[(2-furanylmethyl)amino]benzamide.

Example 35

Benzyltrimethylammonium 5-Aminosulfonyl-4-chloro-2-[(2-furanylmethyl)amino]benzoate (Furosemide Benzyltrimethylammonium Salt)

In similar manner to Example 9, furosemide can be reacted with benzyltrimethylammonium hydroxide to yield benzyltrimethylammonium 5-aminosulfonyl-4-chloro-2-[(2-furanylmethyl)amino]benzoate.

Example 36

Cetyltrimethylammonium 5-Aminosulfonyl-4-chloro-2-[(2-furanylmethyl)amino]benzoate (Furosemide Cetyltrimethylammonium Salt)

In similar manner to Example 10, furosemide can be reacted with cetyltrimethylammonium hydroxide in water to yield cetyltrimethylammonium 5-aminosulfonyl-4-chloro-2-[(2-furanylmethyl)amino]benzoate.

Example 37

N,N-Dimethylaminocarbonylmethyl 5-Aminosulfonyl-4-chloro-2-[(2-furanylmethyl)amino]benzoate (Furosemide N,N-Dimethylelycolamide Ester)

The method of Bundgaard, H., Norgaard, T. and Nielsen, N. M., *Int. J. Pharmaceutics*, 1988, 42, 217-224, can be employed to prepare N,N-dimethylaminocarbonylmethyl 5-aminosulfonyl-4-chloro-2-[(2-furanylmethyl)amino]-benzoate, m.p. 193-194°.

Example 38 t-Butylcarbonyloxymethyl 5-Aminosulfonyl-4-chloro-2-[(2-furanylmethyl)amino]benzoate (Furosemide Pivaxetil Ester)

The method of Mork, N., Bundgaard, H., Shalmi, M. and Christensen, S., *Int. J. Pharmaceutics*, 1990, 60, 163-169, can be employed to prepare t-butylcarbonyloxymethyl 5-aminosulfonyl-4-chloro-2-[(2-furanylmethyl)amino]benzoate.

Example 39

Ethylcarbonyloxymethyl 5-Aminosulfonyl-4-chloro-2-[(2-furanylmethyl)amino]benzoate (Furosemide Propaxetil Ester)

The method of Mork, N., Bundgaard, H., Shalmi, M. and Christensen, S., *Int. J. Pharmaceutics*, 1990, 60, 163-169, can be employed to prepare ethylcarbonyloxymethyl 5-aminosulfonyl-4-chloro-2-[(2-furanylmethyl)amino]benzoate, m.p. 141-142°.

Example 40

5-[1-(t-Butylcarbonyloxymethyl)-1H-tetrazol-5-yl]-2-chloro-4-[(2-thienylmethyl)amino]benzenesulfonamide (Tetrazolyl-Substituted Azosemide)

In a similar manner to Example 12, azosemide can be reacted with chloromethyl pivalate, triethylamine and sodium iodide in DMF to yield 5-[1-(t-Butylcarbonyloxymethyl)-1H-tetrazol-5-yl]-2-chloro-4-[(2-thienylmethyl)amino]benzenesulfonamide.

Example 41

2-Chloro-5-[1-(ethylcarbonyloxymethyl)-1H-tetrazol-5-yl]-4-[(2-thienylmethyl)amino]benzenesulfonamide (Tetrazolyl-Substituted Azosemide)

In similar manner to Example 12, azosemide can be reacted with chloromethyl propionate, triethylamine and sodium iodide in DMF to yield 2-chloro-5-[1-(ethylcarbonyloxymethyl)-1H-tetrazol-5-yl]-4-[(2-thienylmethyl)amino]benzenesulfonamide.

Example 42

2-Chloro-5-[1-(hydroxymethyl)-1H-tetrazol-5-yl]-4-[(2-thienylmethyl)amino]benzenesulfonamide (Tetrazolyl-Substituted Azosemide)

Azosemide can be reacted with formaldehyde in methylene chloride, methylene chloride-DMF mixtures or DMF to yield 2-chloro-5-[1-(hydroxymethyl)-1H-tetrazol-5-yl]-4-[(2-thienylmethyl)amino]benzenesulfonamide.

Example 43

2-Chloro-5-[1-(methoxymethyl)-1H-tetrazol-5-yl]-4-[(2-thienylmethyl)amino]benzenesulfonamide (Tetrazolyl-Substituted Azosemide)

Azosemide can be reacted with formaldehyde and methanol in methylene chloride, methylene chloride-DMF mixtures or DMF to yield 2-chloro-5-[1-(methoxymethyl)-1H-tetrazol-5-yl]-4-[(2-thienylmethyl)amino] benzenesulfonamide.

Example 44

2-Chloro-5-[1-(methylthiomethyl)-1H-tetrazol-5-yl]-4-[(2-thienylmethyl)amino]benzenesulfonamide (Tetrazolyl-Substituted Azosemide)

Azosemide can be reacted with formaldehyde and methanethiol in methylene chloride, methylene chloride-DMF mixtures or DMF to yield 2-chloro-5-[1-(methylthiomethyl)-1H-tetrazol-5-yl]-4-[(2-thienylmethyl)amino]benzenesulfonamide.

Example 45

5-[1-(Benzyloxymethyl)-1H-tetrazol-5-yl]-2-chloro-4-[(2-thienylmethyl)amino]benzenesulfonamide (Tetrazolyl-Substituted Azosemide)

Azosemide can be reacted with benzyl chloromethyl ether, triethylamine and sodium iodide in DMF to yield 5-[1-(benzyloxymethyl)-1H-tetrazol-5-yl]-2-chloro-4-[(2-thienylmethyl)amino]benzenesulfonamide.

Example 46

Benzyltrimethylammonium Salt of 2-Chloro-5-(1H-tetrazol-5-yl)-4-[(2-thienylmethyl)amino]benzenesulfonamide (Azosemide Benzyltrimethylammonium Salt)

In similar manner to Example 9, azosemide can be reacted with benzyltrimethylammonium hydroxide in water to yield the benzyltrimethylammonium salt of 2-chloro-5-(1H-tetrazol-5-yl)-4-[(2-thienylmethyl)amino]benzenesulfonamide.

Example 47

Cetyltrimethylammonium Salt of 2-Chloro-5-(1H-tetrazol-5-yl)-4-[(2-thienylmethyl)amino]benzenesulfonamide (Azosemide Cetyltrimethylammonium Salt)

In similar manner to Example 9, azosemide can be reacted with cetyltrimethylammonium hydroxide in water to yield the cetyltrimethylammonium salt of 2-chloro-5-(1H-tetrazol-5-yl)-4-[(2-thienylmethyl)amino]benzenesulfonamide.

Example 48

3-Isopropylcarbamylsulfonamido-4-(3'-methylphenyl)aminopyridinium t-Butylcarbonyloxymethochloride (Pyridinium-Substituted Torsemide Salt)

In similar manner to Example 12, torsemide can be reacted with chloromethyl pivalate, triethylamine and sodium iodide in DMF to yield 3-isopropylcarbamylsulfonamido-4-(3'-methylphenyl)aminopyridinium t-butylcarbonyloxymethochloride and some 3-isopropylcarbamylsulfonamido-4-(3'-methylphenyl)aminopyridinium t-butylcarbonyloxymethoiodide.

Example 49

3-Isopropylcarbamylsulfonamido-4-(3'-methylphenyl)aminopyridinium Ethylcarbonyloxymethochloride (Pyridinium-Substituted Torsemide Salt)

In similar manner to Example 12, torsemide can be reacted with chloromethyl propionate, triethylamine and sodium iodide in DMF to yield 3-isopropylcarbamylsulfonamido-4-(3'-methylphenyl)aminopyridinium ethylcarbonyloxymethochloride and some 3-isopropylcarbamylsulfonamido-4-(3'-methylphenyl)-aminopyridinium ethylcarbonyloxymethoiodide.

Example 50

3-Isopropylcarbamylsulfonamido-4-(3'-methylphenyl)aminopyridinium benzyloxymethochloride (Pyridinium-Substituted Torsemide Salt)

In a similar manner to Example 3, torsemide can be reacted with benzyl chloromethyl ether and triethylamine in DMF to yield 3-isopropylcarbamylsulfonamido-4-(3'-methylphenyl) aminopyridinium benzyloxymethochloride.

Example 51

3-Isopropylcarbamylsulfonamido-4-(3'-methylphenyl)aminopyridinium methoxymethochloride (Pyridinium-Substituted Torsemide Salt)

In a similar manner to Example 3, torsemide can be reacted with methyl chloromethyl ether and triethylamine and in DMF to yield 3-isopropylcarbamylsulfonamido-4-(3'-methylphenyl)aminopyridinium methoxymethochloride.

Example 52

3-Isopropylcarbamylsulfonamido-4-(3'-methylphenyl)aminopyridinium phenylmethochloride (Pyridinium-Substituted Torsemide Salt)

In a similar manner to Example 3, torsemide can be reacted with benzyl chloride and triethylamine in DMF to yield 3-isopropylcarbamylsulfonamido-4-(3'-methylphenyl)-aminopyridinium phenylmethochloride.

Example 53

3-Isopropylcarbamylsulfonamido-4-(3'-methylphenyl)aminopyridinium Benzylthiomethochloride (Pyridinium-Substituted Torsemide Salt)

In a similar manner to Example 3, torsemide can be reacted with benzyl chloromethyl thioether and triethylamine in DMF to yield 3-isopropylcarbamylsulfonamido-4-(3'-methylphenyl)aminopyridinium benzylthiamethochloride.

Example 54

3-Isopropylcarbamylsulfonamido-4-(3'-methylphenyl)aminopyridinium Methylthiomethochloride (Pyridinium-Substituted Torsemide Salt)

In a similar manner to Example 3, torsemide can be reacted with methyl chloromethyl thioether and triethylamine and in DMF to yield 3-isopropylcarbamylsulfonamido-4-(3'-methylphenyl)aminopyridinium methylthiametho-chloride.

Example 55

Methoxy(polyethyleneoxy)$_{n-1}$-ethyl 3-Aminosulfonyl-5-butylamino-4-phenoxybenzoate (Bumetanide mPEG350 Esters)

In a manner similar to Example 3, bumetanide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 3-aminosulfonyl-5-butylamino-4-phenoxybenzoate where n is in the 7-8 range.

Example 56

Methoxy(polyethyleneoxy)$_{n-1}$-ethyl 3-Aminosulfonyl-5-butylamino-4-phenoxybenzoate (Bumetanide mPEG1000 Esters)

In a manner similar to Example 3, bumetanide can be reacted with MeO-PEG1000-OTs (Biolink Life Sciences, Inc., Cary, N.C., BLS-107-1000) and triethylamine in DMF to yield methoxy(polyethyleneoxy)$_{n-1}$-ethyl 3-aminosulfonyl-5-butylamino-4-phenoxybenzoate where n is in the 19-24 range.

Example 57

Methoxy(polyethyleneoxy)$_{n-1}$-ethyl 3-Aminosulfonyl-4-phenoxy-5-(1-pyrrolidinyl)benzoate (Piretanide mPEG350 Esters)

In similar manner to Example 3, piretanide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 3-aminosulfonyl-4-phenoxy-5-(1-pyrrolidinyl)benzoate where n is in the 7-8 range.

Example 58

Methoxy(polyethyleneoxy)$_{n-1}$-ethyl 3-Aminosulfonyl-4-phenoxy-5-(1-pyrrolidinyl)benzoate (Piretanide mPEG1000 Esters)

In similar manner to Example 3, piretanide can be reacted with MeO-PEG1000-OTs (Biolink Life Sciences, Inc., Cary, N.C., BLS-107-1000) and triethylamine in DMF to yield methoxy(polyethyleneoxy)$_{n-1}$-ethyl 3-amino sulfonyl-4-phenoxy-5-(1-pyrrolidinyl)benzoate where n is in the 19-24 range.

Example 59

Methoxy(polyethyleneoxy)$_{n-1}$-ethyl 5-Aminosulfonyl-4-chloro-2-[(2-furanylmethyl)amino]benzoate (Furosemide mPEG350 Esters)

In similar manner to Example 3, furosemide can be reacted with MeO-PEG350-Cl (Biolink Life Sciences, Inc., Cary, N.C., BLS-106-350) and triethylamine in DMF to yield methoxy(polyethyleneoxy)$_{n-1}$-ethyl 5-aminosulfonyl-4-chloro-2-[(2-furanylmethyl)amino]-benzoate where n is in the 7-8 range.

Example 60

Methoxy(polyethyleneoxy)$_{n-1}$-ethyl 5-Aminosulfonyl-4-chloro-2-[(2-furanylmethyl)amino]benzoate (Furosemide mPEG1000 Esters)

In similar manner to Example 3, furosemide can be reacted with MeO-PEG1000-OTs (Biolink Life Sciences, Inc., Cary, N.C., BLS-107-1000) and triethylamine in DMF to yield methoxy(polyethyleneoxy)$_{n-1}$-ethyl 5-aminosulfonyl-4-chloro-2-[(2-furanylmethyl)amino]-benzoate where n is in the 19-24 range.

Example 61

5-[1-[Methoxy(polyethyleneoxy)$_{n-1}$-ethyl]-1H-tetrazol-5-yl]-2-chloro-4-[(2-thienylmethyl)amino]benzenesulfonamides (N-mPEG350-Tetrazolyl-Substituted Azosemides)

In similar manner to Example 3, azosemide can be reacted with MeO-PEG350-Cl (Biolink Life Sciences, Inc., Cary, N.C., BLS-106-350) and triethylamine in DMF to yield 5-[1-[methoxy(polyethyleneoxy)$_{n-1}$-ethyl]-1H-tetrazol-5-yl]-2-chloro-4-[(2-thienylmethyl)-amino]benzenesulfonamides where n is in the 7-8 range.

Example 62

5-[1-[Methoxy(polyethyleneoxy)$_{n-1}$-ethyl]-1H-tetrazol-5-yl]-2-chloro-4-[(2-thienylmethyl)amino]benzenesulfonamides (N-mPEG1000-Tetrazolyl-Substituted Azosemides)

In similar manner to Example 3, azosemide can be reacted with MeO-PEG1000-OTs (Biolink Life Sciences, Inc., Cary, N.C., BLS-107-1000) and triethylamine in DMF to yield 5-[1-[methoxy(polyethyleneoxy)$_{n-1}$-ethyl]-1H-tetrazol-5-yl]-2-chloro-4-[(2-thienylmethyl)-amino]benzenesulfonamides where n is in the 19-24 range.

Example 63

3-Isopropylcarbamylsulfonamido-4-(3'-methylphenyl)aminopyridinium Methoxy(polyethyleneoxy)$_{n-1}$-ethochlorides (N-mPEG350-Pyridinium Torsemide Salts)

In similar manner to Example 3, torsemide can be reacted with MeO-PEG350-Cl (Biolink Life Sciences, Inc., Cary, N.C., BLS-106-350) and triethylamine in DMF to yield 3-isopropylcarbamylsulfonamido-4-(3'-methylphenyl)aminopyridinium methoxy(polyethyleneoxy)$_{n-1}$-ethochlorides where n is in the 7-8 range.

Example 64

3-Isopropylcarbamylsulfonamido-4-(3'-methylphenyl)aminopyridinium Methoxy(polyethyleneoxy)$_{n-1}$-ethochlorides (N-mPEG1000-Pyridinium Torsemide Salts)

In similar manner to Example 3, torsemide can be reacted with MeO-PEG1000-OTs (Biolink Life Sciences, Inc., Cary, N.C., BLS-107-1000) and triethylamine in DMF to yield 3-isopropylcarbamylsulfonamido-4-(3'-methylphenyl)aminopyridinium methoxy(polyethyleneoxy)$_{n-1}$-ethochlorides where n is in the 19-24 range.

Example 65

3-Aminosulfonyl-5-butylamino-4-phenoxybenzaldehyde (Bumetanide Aldehyde)

By the method of Muraki and Mukiayama (*Chem. Letters*, 1974, 1447 and *Chem. Letters*, 1975, 215), bumetanide can be reacted with bis(4-methylpiperazinyl)aluminum hydride to yield 3-aminosulfonyl-5-butylamino-4-phenoxybenzaldehyde.

Example 66

3-Aminosulfonyl-4-phenoxy-5-(1-pyrrolidinyl)benzaldehyde (Piretanide Aldehyde)

By the method of Muraki and Mukiayama (*Chem. Letters*, 1974, 1447 and *Chem. Letters*, 1975, 215), piretanide can be reacted with bis(4-methylpiperazinyl)aluminum hydride to yield 3-aminosulfonyl-4-phenoxy-5-(1-pyrrolidinyl)benzaldehyde.

Example 67

5-Aminosulfonyl-4-chloro-2-[(2-furanylmethyl)amino]benzaldehyde (Furosemide Aldehyde)

By the method of Muraki and Mukiayama (*Chem. Letters*, 1974, 1447 and *Chem. Letters*, 1975, 215), furosemide can be reacted with bis(4-methylpiperazinyl)aluminum hydride to yield 5-aminosulfonyl-4-chloro-2-[(2-furanylmethyl)amino]benzaldehyde.

Example 68

The Effects of Furosemide on Epileptiform Discharges in Hippocampal Slices

During these studies, spontaneous epileptiform activity was elicited by a variety of treatments. Sprague-Dawley rats (males and females; 25-35 days old) were decapitated, the top of the skull was rapidly removed, and the brain chilled with ice-cold oxygenated slicing medium. The slicing medium was a sucrose-based artificial cerebrospinal fluid (sACSF) consisting of 220 mM sucrose, 3 mM KCl, 1.25 mM $NaH_2PO_4$, 2 mM $MgSO_4$, 26 mM $NaHCO_3$, 2 mM $CaCl_2$, and 10 mM dextrose (295-305 mOsm). A hemisphere of brain containing hippocampus was blocked and glued (cyanoacrylic adhesive) to the stage of a Vibroslicer (Frederick Haer, Brunsick, Me.). Horizontal or transverse slices 400 µm thick were cut in 4° C., oxygenated (95% $O_2$; 5% $CO_2$) slicing medium. The slices were immediately transferred to a holding chamber where they remained submerged in oxygenated bathing medium (ACSF) consisting of 124 mM NaCl, 3 mM KCl, 1.25 mM $NaH_2PO_4$, 2 mM $MgSO_4$, 26 mM $NaHCO_3$, 2 mM $CaCl_2$, and 10 mM dextrose (295-305 mOsm). The slices were held at room temperature for at least 45 minutes before being transferred to a submersion-style recording chamber (all other experiments). In the recording chamber, the slices were perfused with oxygenated recording medium at 34-35° C. All animal procedures were conducted in accordance with NIH and University of Washington animal care guidelines.

In most slice experiments, simultaneous extracellular field electrode recordings were obtained from CA1 and CA3 areas. A bipolar tungsten stimulating electrode was placed on the Schaffer collaterals to evoke synaptically-driven field responses in CA1. Stimuli consisted of 100-300 µsec duration pulses at an intensity of four times the population-spike threshold. After discharges were evoked by a 2 second train of such stimuli delivered at 60 Hz. Spontaneous interictal-like bursts were observed in slices treated by the following modifications or additions to the bathing medium: 10 mM potassium (6 slices; 4 animals; average—81 bursts/min.); 200-300 µM 4-aminopyridine (4 slices; 2 animals; average—33 burst/min.); 50-100 µM bicuculline (4 slices; 3 animals; average—14 bursts/min); M $Mg^{++}$ (1 hour of perfusion—3 slices; 2 animals; average—20 bursts/min. or 3 hours of perfusion—2 slices; 2 animals); zero calcium/6 mM KCl and 2 mM EGTA (4 slices; 3 animals). In all treatments, furosemide was added to the recording medium once a consistent level of bursting was established.

In the first of these procedures, episodes of after discharges were evoked by electrical stimulation of the Schaffer collaterals (Stasheff et al., *Brain Res.* 344:296, 1985) and the extracellular field response was monitored in the CA1 pyramidal cell region (13 slices; 8 animals). The concentration of $Mg^{++}$ in the bathing medium was reduced to 0.9 mM and after discharges were evoked by stimulation at 60 Hz for 2 seconds at an intensity 4 times the population spike threshold (population spike threshold intensity varied between 20-150 µA at 100-300 µsec pulse duration). The tissue was allowed to recover for 10 minutes between stimulation trials. In each experiment, the initial response of CA1 to synaptic input was first tested by recording the field potential evoked by a single stimulus pulse. In the control condition, Schaffer collateral stimulation evoked a single population spike (FIG. 1A, inset). Tetanic stimulation evoked approximately 30 seconds after discharge (FIG. 1A, left) associated with a large change in intrinsic signal (FIG. 1A, right).

For imaging of intrinsic optical signals, the tissue was placed in a perfusion chamber located on the stage of an upright microscope and illuminated with a beam of white light (tungsten filament light and lens system; Dedo Inc.) directed through the microscope condenser. The light was controlled and regulated (power supply—Lamda Inc.) to minimize fluctuations and filtered (695 nm longpass) so that the slice was transilluminated with long wavelengths (red). Field of view and magnification were determined by the choice of microscope objectives (4× for monitoring the entire slice). Image-frames were acquired with: a charge-coupled device (CCD) camera (Dage MTI Inc.) at 30 HZ and were digitized at 8 bits with a spatial resolution of 512×480 pixels using an Imaging Technology Inc. Series 151 imaging system; gains and offsets of the camera-control box and the A/D board were adjusted to optimize the sensitivity of the system. Imaging hardware was controlled by a 486-PC compatible computer. To increase signal/noise, an averaged-image was composed from 16 individual image-frames, integrated over 0.5 sec and averaged together. An experimental series typically involved the continuous acquisition of a series of averaged-images over a several minute time period; at least 10 of these averaged-images were acquired as control-images prior to stimulation. Pseudocolored images were calculated by subtracting the first control-image from subsequently acquired images and assigning a color lookup table to the pixel values. For these images, usually a linear low-pass filter was used to remove high frequency noise and a linear-histogram stretch was used to map the pixel values over the dynamic range of the system. All operations on these images were linear so that quantitative information was preserved. Noise was defined as the maximum standard deviation of fluctuations of AR/R of the sequence of control images within a given acquisition series, where AR/R represented the magnitude of the change in light-transmission through the tissue. Delta R/R was calculated by taking all the difference-images and dividing by the first control image: (subsequent image—first-control-image)/first-control-image. The noise was always <0.01 for each of the chosen image sequences. The absolute change in light transmission through the tissue was estimated during some experiments by acquiring images after placing neutral density filters between the camera and the light source. On average, the camera electronics and imaging system electronics amplified the signal 10-fold prior to digitization so that the peak absolute changes in light transmission through the tissue were usually between 1% and 2%.

The gray-scale photo shown in FIG. 1D is a video image of a typical hippocampal slice in the recording chamber. The fine gold-wire mesh that was used to hold the tissue in place can be seen as dark lines running diagonally across the slice. A stimulating electrode can be seen in the upper right on the stratum radiatum of CA1. The recording electrode (too thin to be seen in the photo) was inserted at the point indicated by the white arrow. FIG. 1A illustrates that two seconds of stimulation at 60 Hz elicited after discharge activity and shows a typical after discharge episode recorded by the extracellular electrode. The inset of FIG. 1A shows the CA1 field response to a single 200 sec test pulse (artifact at arrow) delivered to the Schaffer collaterals. FIG. 1A1 shows a map of the peak change in optical transmission through the tissue evoked by Schaffer collateral stimulation. The region of maximum optical change corresponds to the apical and basal dendritic regions of CA1 on either side of the stimulating electrode. FIG. 1B illustrates sample traces showing responses to stimulation after 20 minutes of perfusion with medium containing 2.5 mM furosemide. Both the electrical after discharge activity (shown in FIG. 1B) and the stimulation-evoked optical changes (shown in FIG. 1B1) were blocked. However, there was a hyper-excitable field response (multiple population spikes) to the test pulse (inset). FIGS. 1C and 1C1 illustrate that restoration of initial response patterns was seen after 45 minutes of perfusion with normal bathing medium.

The opposing effects of furosemide-blockade of the stimulation-evoked after discharges and a concomitant increase of the synaptic response to a test-pulse illustrate the two key results: (1) furosemide blocked epileptiform activity, and (2) synchronization (as reflected by spontaneous epileptiform activity) and excitability (as reflected by the response to a single synaptic input) were dissociated. Experiments in which the dose-dependency of furosemide was examined determined that a minimum concentration of 1.25 mM was required to block both the after discharges and optical changes.

Example 69

Figure 2B:
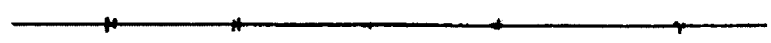
Figure 2C:
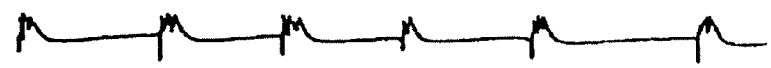
Figure 2D:
Figure 2E:
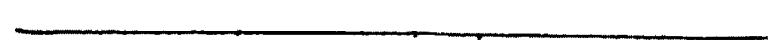
Figure 2F:
Figure 2G:
Figure 2H:
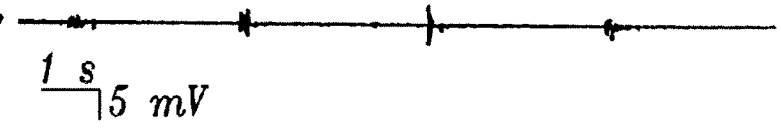

The Effects of Furosemide on Epileptiform Discharges in Hippocampal Slices Perfused with High-$K^+$ (10 mM) Bathing Medium Rat hippocampal slices, prepared as described above, were perfused with a high-$K^+$ solution until extended periods of spontaneous interictal-like bursting were recorded simultaneously in CA3 (top traces) and CA1 (lower traces) pyramidal cell regions (FIGS. 2A and 2B). After 15 minutes of perfusion with furosemide-containing medium (2.5 mM furosemide), the burst discharges increased in magnitude (FIGS. 2C and 2D). However, after 45 minutes of furosemide perfusion, the bursts were blocked in a reversible manner (FIGS. 2E, 2F, 2G and 2H). During this entire sequence of furosemide perfusion, the synaptic response to a single test pulse delivered to the Schaffer colalterals was either unchanged or enhanced (data not shown). It is possible that the initial increase in discharge amplitude reflected a furosemide-induced decrease in inhibition (Misgeld et al., *Science* 232:1413, 1986; Thompson et al., *J. Neurophysiol.* 60:105, 1988; Thompson and Gahwiler, *J. Neuropysiol.* 61:512, 1989; and Pearce, *Neuron* 10:189, 1993). It has previously been reported (Pearce, *Neuron* 10:189, 1993) that furosemide blocks a component of the inhibitory currents in hippocampal slices with a latency (<15 min.) similar to the time to onset of the increased excitability observed here. The longer latency required for the furosemide-block of the spontaneous bursting might correspond to additional time required for a sufficient block of the furosemide-sensitive cellular volume regulation mechanisms under high-$K^+$ conditions.

Figure 2I:
Figure 2J:
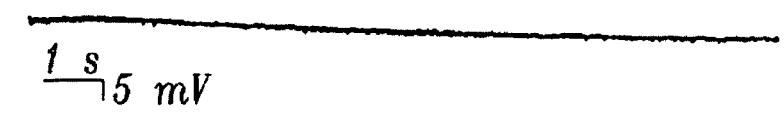

After testing the effects of furosemide on slices perfused with high-$K^+$, similar studies were performed with a variety of other commonly studied in vitro models of epileptiform discharge (Galvan et al., *Brain Res.* 241:75, 1982; Schwartzkroin and Prince, *Brain Res.*183:61, 1980; Anderson et al., *Brain Res.* 398:215, 1986; and Zhang et al., *Epilepsy Res.* 20:105, 1995). After prolonged exposure (2-3 hours) to magnesium-free medium (0-$Mg^{++}$), slices have been shown to develop epileptiform discharges that are resistant to common clinically used anticonvulsant drugs (Zhang et al., *Epilepsy Res.* 20:105, 1995). Recordings from entorhinal cortex (FIG. 2I) and subiculum (not shown) showed that after 3 hours of perfusion with 0-$Mg^{++}$ medium, slices developed bursting patterns that appeared similar to these previously described "anticonvulsant resistant" bursts. One hour after the addition of furosemide to the bathing medium, these bursts were blocked (FIG. 2J). Furosemide also blocked spontaneous burst discharges observed with the following additions/modifications to the bathing medium: (1) addition of 200-300 µM 4-aminopyridine (4-AP; a potassium channel blocker) (FIGS. 2K and 2L); (2) addition of the GABA antagonist, bicuculline, at 50-100 µM (FIGS. 2M and 2N); (3) removal of magnesium (0-$Mg^{++}$)—1 hours perfusion (FIGS. 2O and 2P); and (4) removal of calcium plus extracellular chelation (0-$Ca^{++}$) (FIGS. 2Q and 2R). With each of these manipulations, spontaneous interictal-like patterns were simultaneously recorded from CA1 and CA3 subfields (FIGS. 2K, 2L, 2M and 2N show only the CA3 trace and FIGS. 2O, 2P, 2Q, and 2R show only the CA1 trace). In the 0-$Ca^{++}$ experiments, 5 mM furosemide blocked the bursting with a latency of 15-20 minutes. For all other protocols, bursting was blocked by 2.5 mM furosemide with a latency of 20-60 minutes. Furosemide reversibly blocked the spontaneous bursting activity in both CA1 and CA3 in all experiments (FIGS. 2L, 2N, 2P and 2R).

Example 70

The Effects of Furosemide on Epileptiform Activity Induced by i.v. Injection of Kainic Acid in Anesthetized Rats This example illustrates an in vivo model in which epileptiform activity was induced by i.v. injection of kainic acid (KA) into anesthetized rats (Lothman et al., *Neurology* 31:806, 1981). The results are illustrated in FIGS. 3A-3H. Sprague-Dawley rats (4 animals; weights 250-270 g) were anesthetized with urethane (1.25 g/kg i.p.) and anesthesia maintained by additional urethane injections (0.25 g/kg i.p.) as needed. Body temperature was monitored using a rectal temperature probe and maintained at 35-37° C. with a heating pad; heart rate (EKG) was continuously monitored. The jugular vein was cannulated on one side for intravenous drug administration. Rats were placed in a Kopf stereotaxic device (with the top of the skull level), and a bipolar stainless-steel microelectrode insulated to 0.5 mm of the tip was inserted to a depth of 0.5-1.2 mm from the cortical surface to record electroencephalographic (EEG) activity in the fronto-parietal cortex. In some experiments, a 2M NaCl-containing pipette was lowered to a depth of 2.5-3.0 mm to record hippocampal EEG. Data were stored on VHS videotape and analyzed off-line.

Following the surgical preparation and electrode placement, animals were allowed to recover for 30 minutes before the experiments were initiated with an injection of kainic acid (10-12 mg/kg i.v.). Intense seizure activity, an increased heart rate, and rapid movements of the vibrissae were induced with a latency of about 30 minutes. Once stable electrical seizure was evident, furosemide was delivered in 20 mg/kg boluses every 30 minutes to a total of 3 injections. Experiments were terminated with the intravenous administration of urethane. Animal care was in accordance with NIH guidelines and approved by the University of Washington Animal Care Committee.

FIGS. 3A-3H show furosemide blockade of kainic acid-evoked electrical "status epilepticus" in urethane-anesthetized rats. EKG recordings are shown as the top traces and EEG recordings are shown as the bottom traces. In this model, intense electrical discharge (electrical "status epilepticus") was recorded from the cortex (or from depth hippocampal electrodes) 30-60 minutes after KA injection (10-12 mg/kg) (FIGS. 3C and 3D). Control experiments (and previous reports, Lothman et al., *Neurology*, 31:806, 1981) showed that this status-like activity was maintained for well over 3 hours. Subsequent intravenous injections of furosemide (cumulative dose: 40-60 mg/kg) blocked seizure activity with a latency of 30-45 minutes, often producing a relatively flat EEG (FIGS. 3E, 3F, 3G and 3H). Even 90 minutes after the furosemide injection, cortical activity remained near normal baseline levels (i.e., that observed prior to the KA and furosemide injections). Studies on the pharmacokinetics of furosemide in the rat indicate that the dosages used in this example were well below toxic levels (Hammarlund and Paalzow, *Biopharmaceutics Drug Disposition*, 3:345, 1982).

Experimental Methods for Examples 71-74

Hippocampal slices were prepared from Sprague-Dawley adult rats as described previously. Transverse hippocampal slices 100 μm thick were cut with a vibrating cutter. Slices typically contained the entire hippocampus and subiculum. After cutting, slices were stored in an oxygenated holding chamber at room temperature for at least one hour before recording. All recordings were acquired in an interface type chamber with oxygenated (95% $O_2$, 5% $CO_2$) artificial cerebral spinal fluid (ACSF) at 34°-35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose.

Sharp-electrodes for intracellular recordings from CA1 and CA3 pyramidal cells were filled with 4 M potassium acetate. Field recordings from the CA1 and CA3 cell body layers were acquired with low-resistance glass electrodes filled with 2 M NaCl. For stimulation of the Schaffer collateral or hilar pathways, a small monopolar tungsten electrode was placed on the surface of the slice. Spontaneous and stimulation-evoked activities from field and intracellular recordings were digitized (Neurocorder, Neurodata Instruments, New York, N.Y.) and stored on videotape. AxoScope software (Axon Instruments) on a personal computer was used for off-line analysis of data.

In some experiments, normal or low-chloride medium was used containing bicuculline. (20 μM), 4-amino pyridine (4-AP) (100 EM), or high-$K^+$ (7.5 or 12 mM). In all experiments, low-chloride solutions (7, and 21 mM $[Cl^-]_o$) were prepared by equimolar replacement of NaCl with $Na^+$-gluconate (Sigma). All solutions were prepared so that they had a pH of approximately 7.4 and an osmolarity of 290-300 mOsm at 35° C. and at equilibrium from carboxygenation with 95% $O_2$/5% $CO_2$.

After placement in the interface chamber, slices were superfused at approximately 1 ml/min. At this flow-rate, it took 8-10 minutes for changes in the perfusion media to be completed. All of the times reported here have taken this delay into account and have an error of approximately ±2 minutes.

Example 71

Timing of Cessation of Spontaneous Epileptiform Bursting in Areas in CA1 and CA3

The relative contributions of the factors that modulate synchronized activity vary between areas CA1 and CA3. These factors include differences in the local circuitry and region-specific differences in cell packing and volume fraction of the extracellular spaces. If the anti-epileptic effects of anion or chloride-cotransport antagonism are due to a desynchronization in the timing of neuronal discharge, chloride-cotransport blockade might be expected to differentially affect areas CA1 and CA3. To test this, a series of experiments was performed to characterize differences in the timing of the blockade of spontaneous epileptiform activity in areas CA1 and CA3.

Field activity was recorded simultaneously in areas CA1 and CA3 (approximately midway between the most proximal and distal extent the CA3 region), and spontaneous bursting was induced by treatment with high-$[K^+]_o$ (12 μM; n=12), bicuculline (20 mM; n=12), or 4-AP (100 μM; n=5). Single electrical stimuli were delivered to the Schaffer collaterals, midway between areas CA1 and CA3, every 30 seconds so that the field responses in areas CA1 and CA3 could be monitored throughout the duration of each experiment. In all experiments, at least 20 minutes of continuous spontaneous epileptiform bursting was observed prior to switching to low $[Cl^-]_o$ (21 mM) or furosemide-containing (2.5 mM) medium.

In all cases, after 30-40 minutes exposure to furosemide or low-chloride medium, spontaneous bursting ceased in area CA1 before the bursting ceased in area CA3. The temporal sequence of events typically observed included an initial increase in burst frequency and amplitude of the spontaneous field events, then a reduction in the amplitude of the burst discharges which was more rapid in CA1 than in CA3. After CA1 became silent, CA3 continued to discharge for 5-10 minutes, until it too no longer exhibited spontaneous epileptiform events.

This temporal pattern of burst cessation was observed with all epileptiform-inducing treatments tested, regardless of whether the agent used for blockade of spontaneous bursting was furosemide or low-$[Cl^-]_o$ medium. Throughout all stages of these experiments, stimulation of the Schaffer collaterals evoked hyperexcited field responses in both the CA1 and CA3 cell body layers. Immediately after spontaneous bursting was blocked in both areas CA1 and CA3, hyperexcited population spikes could still be evoked.

We considered the possibility that the observed cessation of bursting in CA1 prior to CA3 was an artifact of the organization of synaptic contacts between these areas relative to our choice of recording sites. It is known that the projections of the various subregions of CA3 terminate in an organized fashion in CA1; CA3 cells closer to the dentate gyrus (proximal CA3) tend to project most heavily to the distal portions of CA1 (near the subicular border), whereas CA3 projections arising from cells located more distally in CA3 terminate more heavily in portions of CA1 located closer to the CA2 border. If the cessation of bursting occurs in the different subregions of CA3 at different times, the results of the above set of experiments might arise not as a difference between CA1 and CA3, but rather as a function of variability in bursting activity across CA3 subregions. We tested this possibility in three experiments. Immediately after the spontaneous bursting ceased in CA1, we surveyed the CA3 field with a recording electrode. Recordings from several different CA3 locations (from the most proximal to the most distal portions of CA3), showed that all subregions of area CA3 were spontaneously bursting during the time that CA1 was silent.

The observation that CA3 continued to discharge spontaneously after CA1 became silent was unexpected since population discharges in CA3 are generally thought to evoke discharges in CA1 through excitatory synaptic transmission. As previously described, single-pulse stimuli delivered to the Schaffer collaterals still evoked multiple population spikes in CA1 even after the blockade of spontaneous bursting; thus, hyperexcited excitatory synaptic transmissions in CA3-to-CA1 synapse was intact. Given this maintained efficacy of synaptic transmission, and the continued spontaneous field discharges in CA3, we postulated that the loss of spontaneous bursting in CA1 was due to a decrease in synchronization of incoming excitatory drive. Further, since spontaneous epileptiform discharge in CA3 also eventually ceased, perhaps this desynchronization process occurred at different times in the two hippocampal subfields.

Example 72

Effect of Chloride-Cotransport Antagonism on the Synchronization of CA1 and CA3 Field Population Discharges The observation from Example 4 suggested a temporal relationship between the exposure time to low-$[Cl^-]_o$ or furosemide-containing medium and the characteristics of the spontaneous burst activity. Further, this relationship was different between areas CA1 and CA3. In order to better characterize the temporal relationships, we compared the occurrences of CA1 action potentials and the population spike events in the field responses of CA1 and CA3 subfields during spontaneous and stimulation-evoked burst discharge.

Intracellular recordings were obtained from CA1 pyramidal cells, with the intracellular electrode placed close (<100 μM) to the CA1 field electrode. The slice was stimulated every 20 seconds with single stimuli delivered to the Schaffer collaterals. After continuous spontaneous bursting was established for at least 20 minutes, the bathing medium was switched to bicuculline-containing low-$[Cl^-]_o$ (21 mM) medium. After approximately 20 minutes, the burst frequency and amplitude was at its greatest. Simultaneous field and intracellular recordings during this time showed that the CA1 field and intracellular recordings were closely synchronized with the CA3 field discharges. During each spontaneous discharge, the CA3 field response preceded the CA1 discharge by several milliseconds. During stimulation-evoked events, action potential discharges of the CA1 pyramidal cell were closely synchronized to both CA3 and CA1 field discharges.

With continued exposure to low-$[Cl^-]_o$ medium, the latency between the spontaneous discharges of areas CA1 and CA3 increased, with a maximum latency of 30-40 milliseconds occurring after 30-40 minutes exposure to the bicuculline-containing low-chloride medium. During this time, the amplitude of both the CA1 and CA3 spontaneous field discharges decreased. Stimulation-evoked discharges during this time closely mimicked the spontaneously occurring discharges in morphology and relative latency. However, the initial stimulus-evoked depolarization of the neuron (presumably, the monosynaptic EPSP) began without any significant increase in latency. The time interval during which these data were acquired corresponds to the time immediately prior to the cessation of spontaneous bursting in CA1.

After 40-50 minutes perfusion with low-$[Cl^-]_o$ medium, the spontaneous bursts were nearly abolished in CA1 but were unaffected in CA3. Schaffer collateral stimulation during this time showed that monosynaptically-triggered responses of CA1 pyramidal cells occurred without any significant increase in latency, but that stimulation-evoked field responses were almost abolished. The time interval during which these data were acquired corresponds to the moments immediately prior to the cessation of spontaneous bursting in CA3.

After prolonged exposure to low-$[Cl^-]_o$ medium, large increases (>30 milliseconds) developed in the latency between Schaffer collateral stimulation and the consequent CA3 field discharge. Eventually, no field responses could be evoked by Schaffer collateral stimulation in either areas CA1 and CA3. However, action potential discharge from CA1 pyramidal cells in response to Schaffer collateral stimulation could be evoked with little change in response latency. Indeed, for the entire duration of the experiments (greater than two hours), action potential discharges form CA1 pyramidal cells could be evoked at short latency by Schaffer collateral stimulation. Further, although stimulation-evoked hyperexcited discharges of CA3 were eventually blocked after prolonged exposure to low-$[Cl^-]_o$ medium, the antidromic response in CA3 appeared to be preserved.

Example 73

Effects of Chloride-Cotransport Antagonism on the Synchronization of Burst Discharges in CA1 Pyramidal Cells The foregoing data suggest the disappearance of the field responses may be due to a desynchronization of the occurrence of action potentials among neurons. That is, although synaptically-driven excitation of CA1 pyramidal cells was not preserved, action potential synchrony among the CA1 neuronal population was not sufficient to summate into a measurable DC field response. In order to test this, paired intracellular recordings of CA1 pyramidal cells were acquired simultaneously with CA1 field responses. In these experiments, both the intracellular electrodes and the field recording electrodes were placed within 200 μm of one another.

During the period of maximum spontaneous activity induced by bicuculline-containing low-$[Cl^-]_o$ medium, recordings showed that action potentials between pairs of CA1 neurons and the CA1 field discharges were tightly synchronized both during spontaneous and stimulation-evoked discharges. After continued exposure to low-$[Cl^-]_o$ medium, when the amplitude of the CA1 field discharge began to broaden and diminish, both spontaneous and stimulation-evoked discharges showed a desynchronization in the timing of the occurrences of action potentials between pairs of CA1 neurons, and between the action potentials and the field responses. This desynchronization was coincident with the suppression of CA1 field amplitude. By the time that spontaneous bursting in CA1 ceased, a significant increase in latency had developed between Schaffer collateral stimulation and CA1 field discharge. At this time, paired intracellular recordings showed a dramatic desynchronization in the timing of action potential discharge between pairs of neurons and between the occurrence of action potentials and the field discharges evoked by Schaffer collateral stimulation.

It is possible that the observed desynchronization of CA1 action potential discharge is due to the randomization of mechanisms necessary for synaptically-driven action potential generation, such as a disruption in the timing of synaptic release or random conduction failures at neuronal processes. If this were the case, then one would expect that the occurrence of action potentials between a given pair of neurons would vary randomly with respect to one another, from stimulation to stimulation. We tested this by comparing the patterns of action potential discharge of pairs of neurons between multiple consecutive stimuli of the Schaffer collaterals. During each stimulation event, the action potentials occurred at nearly identical times with respect to one another, and showed an almost identical burst morphology from stimulation to stimulation. We also checked to see whether the occurrence of action potentials between a given pair of neurons during spontaneous field discharges was fixed in time. The patterns of action potential discharges from a given pair of CA1 neurons was compared between consecutive spontaneous field bursts during the time when the occurrence of action potentials was clearly desynchronized. Just as in the case of stimulation-evoked action potential discharge described above, the action potentials generated during a spontaneous population discharge occurred at nearly identical times with respect to one another, and showed a nearly identical burst morphology from one spontaneous discharge to the next.

Example 74

Effects of Low-Chloride Treatment on Spontaneous Synaptic Activity

It is possible that the anti-epileptic effects associated with chloride-cotransport antagonism are mediated by some action on transmitter release. Blockade of chloride-cotransport could alter the amount or timing of transmitter released from terminals, thus affecting neuronal synchronization. To test whether low-$[Cl^-]_o$ exposure affected mechanisms associated with transmitter release, intracellular CA1 responses were recorded simultaneously with CA1 and CA3 field responses during a treatment which dramatically increases spontaneous synaptic release of transmitter from presynaptic terminals.

Increased spontaneous release of transmitter was induced by treatment with 4-AP (100 µM). After 40 minutes exposure to 4-AP-containing medium, spontaneous synchronized burst discharges were recorded in area CA1 and CA3. Switching to 4-AP-containing low-$[Cl^-]_o$ medium led initially, as was shown previously, to enhanced spontaneous bursting. High-grain intracellular recordings showed that high-amplitude spontaneous synaptic activity was elicited by 4-AP treatment. Further exposure to low-chloride medium blocked spontaneous burst discharge in CA1, although CA3 continued to discharge spontaneously. At this time, CA1 intracellular recordings showed that spontaneous synaptic noise was further increased, and remained so for prolonged exposure times to 4-AP-containing low-chloride medium. These data suggest that mechanisms responsible for synaptic release from terminals are not adversely affected by low-chloride exposure in a manner that could explain the blockade of 4-AP-induced spontaneous bursting in CA1. These results also eliminate the possibility that the effects of low-$[Cl^-]_o$ exposure are due to alterations in CA1 dendritic properties which would compromise their efficiency in conducting PSPs to the soma.

Experimental Methods for Examples 75 to 79

In all of the following experiments, $[Cl^-]_o$ was reduced by equimolar replacement of NaCl with $Na^+$-gluconate. Gluconate was used rather than other anion replacements for several reasons. First, patch-clamp studies have demonstrated that gluconate appears to be virtually impermeant to chloride channels, whereas other anions (including sulfate, isethionate, and acetate) are permeable to varying degrees. Second, transport of extracellular potassium through glial NKCC1 cotransport is blocked when extracellular chloride is replaced by gluconate but is not completely blocked when replaced by isethionate. Since this furosemide-sensitive cotransporter plays a significant role in cell swelling and volume changes of the extracellular space (ECS), we wished to use the appropriate anion replacement so that the effects of our treatment would be comparable to previous furosemide experiments (Hochman et al. *Science,* 270:99-102, 1995; U.S. Pat. No. 5,902,732). Third, formate, acetate, and proprionate generate weak acids when employed as $Cl^-$ substitutes and lead to a prompt fall in intracellular pH; gluconate remains extracellular and has not been reported to induce intracellular pH shifts. Fourth, for purposes of comparison we wished to use the same anion replacement that had been used in previous studies examining the effects of low-$[Cl^-]_o$ on activity-evoked changes of the ECS.

There is some suggestion that certain anion-replacements might chelate calcium. Although subsequent work has failed to demonstrate any significant ability of anion-substitutes to chelate calcium, there is still some concern in the literature regarding this issue. Calcium chelation did not appear to be an issue in the following experiments, since resting membrane potentials remained normal and synaptic responses (indeed, hyperexcitable synaptic responses) could be elicited even after several hours of exposure to medium in which $[Cl^-]_o$ had been reduced by gluconate substitution. Further, we confirmed that calcium concentration in our low-$[Cl^-]_o$-medium was identical to that in our control-medium by measurements made with $Ca^{2+}$-selective microelectrodes.

Sprague-Dawley adult rats were prepared as previously described. Briefly, transverse hippocampal slices, 400 µm thick, were cut using a vibrating cutter. Slices typically contained the entire hippocampus and subiculum. After cutting, slices were stored in an oxygenated holding chamber for at least one hour prior to recording. All recordings were acquired in an interface type chamber with oxygenated (95% $O_2$/5% $CO_2$) artificial cerebral spinal fluid (ACSF) at 34°-35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose. In some experiments, normal or low-chloride medium was used containing bicuculline (20 µM), 4-AP (100 µM), or high-$K^+$ (12 mM). Low-chloride solutions (7, 16, and 21 mM $[Cl^-]_o$) were prepared by equimolar replacement of NaCl with $Na^+$-gluconate (Sigma Chemical Co., St. Louis, Mo.). All solutions were prepared so that they had a pH of approximately 7.4 and an osmolarity of 290-300 mOsm at 35° C. and at equilibrium from carboxygenation with 95% $O_2$/5% $CO_2$.

Sharp-electrodes filled with 4 M potassium acetate were used for intracellular recordings from CA1 pyramidal cells. Field recordings from the CA1 or CA3 cell body layers were acquired with low-resistance glass electrodes filled with NaCl (2 M). For stimulation of the Schaffer collateral pathway, a small monopolar electrode was placed on the surface of the slice midway between areas CA1 and CA3. Spontaneous and stimulation-evoked activities from field and intracellular recordings were digitized (Neurocorder, Neurodata Instruments, New York, N.Y.), and stored on video tape. Axo-Scope software (Axon Instruments Inc.) on a PC-computer was used for off-line analyses of data.

Ion-selective microelectrodes were fabricated according to standard methods well known in the art. Double-barreled pipettes were pulled and broken to a tip diameter of approximately 3.0 µm. The reference barrel was filled with ACSF and the other barrel was sylanized and the tip back-filled with a resin selective for $K^+$ (Corning 477317). The remainder of the sylanized barrel was filled with KCl (140 mM). Each barrel was led, via Ag/AgCl wires, to a high impedance dual-differential amplifier (WPI FD223). Each ion-selective microelectrode was calibrated by the use of solutions of known ionic composition and was considered suitable if it was characterized by a near-Nernstian slope response and if it remained stable throughout the duration of the experiment.

After placement in the interface chamber, slices were superfused at approximately 1 ml/minute. At this flow-rate, it took approximately 8-10 minutes for changes in perfusion media to be completed. All of the times reported here have taken this time-delay into account and have an error of approximately ±2 minutes.

Example 75

Effects of Low-[Cl—]$_o$ on CA1 Field Recordings

Other studies have shown that prolonged exposure of cortical and hippocampal slices to low-[Cl$^-$]$_o$ does not affect basic intrinsic and synaptic properties such as input resistance, resting membrane potential, depolarization-induced action-potential generation, or excitatory synaptic transmission. A previous study has also partly characterized the epileptogenic properties of low-[Cl$^-$]$_o$ exposure to the CA1 area of hippocampus. The following studies were performed to observe the times of onset and possible cessation of low-[Cl$^-$]$_o$-induced hyperexcitability and hypersynchronization. Slices (n=6) were initially perfused with normal medium until stable intracellular and field recordings were established in a CA1 pyramidal cell and the CA1 cell body layer, respectively. In two experiments, the same cell was held throughout the entire length of the experiment (greater than 2 hours). In the remaining experiments (n=4), the initial intracellular recording was lost during the sequence of medium changes and additional recordings were acquired from different cells. Patterns of neuronal activity in these experiments were identical to those seen when a single cell was observed.

The field and intracellular electrodes were always placed in close proximity to one another (<200 μm). In each case, after approximately 15-20 minutes exposure to the low-[Cl$^-$]$_o$-medium (7 mM), spontaneous bursting developed, first at the cellular level, and then in the field. This spontaneous field activity, representing synchronized burst discharge in a large population of neurons, lasted from 5-10 minutes, after which time the field recording became silent. When the field first became silent, the cell continued to discharge spontaneously. This result suggests that population activity has been "desynchronized" while the ability of individual cells to discharge has not been impaired. After approximately 30 minutes exposure to low-[Cl$^-$]$_o$-medium, intracellular recording showed that cells continued to discharge spontaneously even though the field remained silent. The response of the cell to intracellular current injection at two time points demonstrated that the cell's ability to generate action potentials had not been impaired by low-[Cl$^-$]$_o$ exposure. Further, electrical stimulation in CA1 stratum radiatum elicited burst discharges, indicating that a hyperexcitable state was maintained in the tissue.

Example 76

Effects of Low-[Cl$^-$]$_o$ on High-[K$^+$]$_o$-Induced Epileptiform Activity in CA1

The previous set of experiments showed that tissue exposure to low-[Cl$^-$]$_o$ medium induced a brief period of spontaneous field potential bursting which ceased within 10 minutes. If a reduction of [Cl$^-$]$_o$ is indeed eventually capable of blocking spontaneous epileptiform (i.e. synchronized) bursting, then these results suggest that anti-epileptic effects would likely be observable only after this initial period of bursting activity has ceased. We therefore examined the temporal effects of low-[Cl$^-$]$_o$-treatment on high-[K$^+$]$_o$-induced bursting activity. Slices (n=12) were exposed to medium in which [K$^+$]$_o$ had been increased to 12 mM, and field potentials were recorded with a field electrode in the CA1 cell body layer. Spontaneous field potential bursting was observed for at least 20 minutes, and then the slices were exposed to medium in which [K$^+$]$_o$ was maintained at 12 mM, but [Cl$^-$]$_o$ was reduced to 21 mM. Within 15-20 minutes after the tissue was exposed to the low-[Cl$^-$]$_o$/high-[K$^+$]$_o$-medium, the burst amplitude increased and each field event had a longer duration. After a brief period of this facilitated field activity (lasting 5-10 minutes), the bursting stopped. To test whether this blockade was reversible, after at least 10 minutes of field potential silence, we switched back to high-[K$^+$]$_o$-medium with normal [Cl$^-$]$_o$. The bursting returned within 20-40 minutes. Throughout each experiment, the CA1 field response to Schaffer collateral stimulation was monitored. The largest field responses were recorded just before the cessation of spontaneous bursting, during the period when the spontaneous bursts had the largest amplitude. Even after the blockade of spontaneous bursting, however, multiple population spikes were elicited by Schaffer collateral stimulation, indicating that synaptic transmission was intact, and that the tissue remained hyperexcitable.

In four slices, intracellular recordings from CA1 pyramidal cells were acquired along with the CA1 field recording. During the period of high-[K$^+$]$_o$-induced spontaneous bursting, hyperpolarizing current was injected into the cell so that postsynaptic potentials (PSPs) could be better observed. After low-[Cl$^-$]$_o$-blockade of spontaneous bursting, spontaneously occurring action potentials and PSPs were still observed. These observations further support the view that synaptic activity, per se, was not blocked by the low-[Cl$^-$]$_o$ treatment.

Example 77

Low-[Cl$^-$]$_o$-Blockade of Epileptiform Activity Induced by 4-AP, High-[K$^+$]$_o$, and Bicuculline in CA1 and CA3

We next tested whether low-[Cl$^-$]$_o$ treatment could block epileptiform activity in areas CA1 and CA3, which was elicited by different pharmacological treatments, as we had shown for furosemide treatment. For this set of experiments, we chose to test the effects of low-[Cl$^-$]$_o$ treatment on spontaneous bursting which had been induced by high-[K$^+$]$_o$ (12 mM) (n=5), 4-AP (100 μM) (n=4), and bicuculline (20 and 100 μM) (n=5). In each set of experiments, field responses were recorded simultaneously from areas CA1 and CA3, and in each case, the spontaneous epileptiform activity in both areas CA1 and CA3, was reversibly blocked within 30 minutes after [Cl$^-$]$_o$ in the perfusion medium had been reduced to 21 mM. These data suggest that, like furosemide, low-[Cl$^-$]$_o$ reversibly blocks spontaneous bursting in several of the most commonly studied in vitro models of epileptiform activity.

Example 78

Comparison Between Low-[Cl$^-$]$_o$ and Furosemide on Blockade of High-[K$^+$]$_o$-Induced Epileptiform Activity The data from the previous sets of experiments are consistent with the hypothesis that the anti-epileptic effects of both low-[Cl$^-$]$_o$ and furosemide are mediated by their actions on the same physiological mechanisms. To further test this hypothesis, we compared the temporal sequence of effects of low-$[Cl^-]_o$ (n=12) and furosemide (2.5 and 5 mM) (n=4) on high-$[K^+]_o$-induced bursting, as recorded with a field electrode in CA1. We found that both low-$[Cl^-]_o$ and furosemide treatment induced a similar temporal sequence of effects: an initial brief period of increased amplitude of field activity, and then blockade (reversible) of spontaneous field activity. In both cases, electrical stimulation of the Schaffer collaterals elicited hyperexcited responses even after the spontaneous bursting had been blocked.

Example 79

Consequences of Prolonged Exposure to Low-$[Cl^-]_o$ Medium with Varied $[K^+]_o$ In the preceding experiments, we monitored field activity in some slices for >1 hour after the spontaneous bursting had been blocked by low-$[Cl^-]_o$ exposure. After such prolonged low-$[Cl^-]_o$ exposure, spontaneous, long-lasting, depolarizing shifts developed. The morphology and frequency of these late-occurring field events appeared to be related to the extracellular potassium and chloride concentrations. Motivated by these observations, we performed a set of experiments in which we systematically varied $[Cl^-]_o$ and $[K^+]_o$ and observed the effects of these ion changes on the late-occurring spontaneous field events.

In our first set of experiments, slices were exposed to medium containing low-$[Cl^-]_o$ (7 mM) and normal-$[K^+]_o$ (3 mM) (n=6). After 50-70 minutes exposure to this medium, spontaneous events were recorded in area CA1; these events appeared as 5-10 mV negative shifts in the DC field, with the first episode lasting for 30-60 seconds. Each subsequent episode was longer than the previous one. This observation suggested that ion-homeostatic mechanisms were diminished over time as a result of the ion concentrations in the bathing medium. In some experiments (n=2) in which these negative DC field shifts had been induced, intracellular recordings from CA1 pyramidal cells were acquired simultaneously with the CA1 field recordings.

For these experiments, the intracellular and field recordings were acquired close to one another (<200 μm). Prior to each negative field shift (10-20 seconds), the neuron began to depolarize. Cellular depolarization was indicated by a decrease in resting membrane potential, an increase in spontaneous firing frequency, and a reduction of action potential amplitude. Coincident with the onset of the negative field shifts, the cells became sufficiently depolarized so that they were unable to fire spontaneous or current-elicited (not shown) action potentials. Since neuronal depolarization began 10-20 seconds prior to the field shift, it may be that a gradual increase in extracellular potassium resulted in the depolarization of a neuronal population, thus initiating these field events. Such an increase in $[K^+]_o$ might be due to alterations of the chloride-dependent glial cotransport mechanisms that normally move potassium from extracellular to intracellular spaces. To test whether increases in $[K^+]_o$ preceded these negative field shifts (and paralleled cellular depolarization), experiments (n=2) were performed in which a $K^+$-selective microelectrode was used to record changes in $[K^+]_o$.

In each experiment, the $K^+$-selective microelectrode and a field electrode were placed in the CA1 pyramidal layer close to one another (<200 μm), and a stimulation pulse was delivered to the Schaffer collaterals every 20 seconds so that the magnitude of the population spike could be monitored. Multiple spontaneously occurring negative field shifts were evoked by perfusion with low-$[Cl^-_o]$ (7 mM) medium. Each event was associated with a significant increase in $[K^+]_o$, with the $[K^+]_o$ increase starting several seconds prior to the onset of negative field shift. A slow 1.5-2.0 mM increase in $[K^+]_o$ occurred over a time interval of approximately 1-2 minute seconds prior to the onset of each event. The stimulation-evoked field responses slowly increased in amplitude over time, along with the increasing $[K^+]_o$, until just before the negative field shift.

In a second set of experiments (n=4), $[K^+]_o$ was increased to 12 mM and $[Cl^-]_o$ was increased to 16 mM. After 50-90 minutes exposure to this medium, slow oscillations were recorded in area CA1. These oscillations were characterized by 5-10 mV negative DC shifts in the field potential and had a periodicity of approximately 1 cycle/40 seconds. Initially, these oscillations occurred intermittently and had an irregular morphology. Over time, these oscillations became continuous and developed a regular waveform. Upon exposure to furosemide (2.5 mM), the amplitude of the oscillations was gradually decreased and the frequency increased until the oscillations were completely blocked. Such low-$[Cl^-]_o$-induced oscillations in tissue slices have not been previously reported. However, the temporal characteristics of the oscillatory events bear a striking resemblance to the low-$[Cl^-]_o$-induced $[K^+]_o$ oscillations which were previously described in a purely axonal preparation.

In a third set of experiments (n=5) $[Cl^-]_o$ was further increased to 21 mM and $[K^+]_o$ was reduced back to 3 mM. In these experiments, single, infrequently occurring negative shifts of the field potential developed within 40-70 minutes (data not shown). These events (5-10 mV) lasting 40-60 seconds, occurred at random intervals, and maintained a relatively constant duration throughout the experiment. These events could sometimes be elicited by a single electrical stimulus delivered to the Schaffer collaterals.

Finally, in a final set of experiments (n=5), $[Cl^-]_o$ was kept at 21 mM and $[K^+]_o$ was raised to 12 mM. In these experiments, late-occurring spontaneous field events were not observed during the course of the experiments (2-3 hours).

Example 80

Changes in $[K^+]_o$ During Low-Chloride Exposure

Sprague-Dawley adult rats were prepared as previously described. Transverse hippocampal slices, 400 μm thick, were cut with a vibrating cuter and stored in an oxygenated holding chamber for 1 hour before recording. A submersion-type chamber was used for $K^+$-selective microelectrode recordings. Slices were perfused with oxygenated (95% $O_2$/5% $CO_2$) artificial cerebrospinal fluid (ACSF) at 34-35° C. Normal ACSF contained 10 mM dextrose, 124 mM NaCl, 3 mM KCl, 1.25 mM $NaH_2PO_4$, 1.2 mM $MgSO_4$, 26 mM $NaHCO_3$ and 2 mM $CaCl_2$. In some experiments, normal or low-chloride medium was used containing 4-aminopyridine (4-AP) at 100 μM. Low-chloride solutions (21 mM $[Cl]_0$) were prepared by equimolar replacement of NaCl with Na+-gluconate (Sigma Chemical Co.).

Field recordings from the CA1 or CA3 cell body layers were acquired with low-resistance glass electrodes filled with NaCl (2M). For stimulation of the Schaffer collateral pathway, a monopolar stainless-steel electrode was placed on the surface of the slide midway between areas CA1 and CA3. All recordings were digitized (Neurorocorder, Neurodata Instruments, New York, N.Y.) and stored on videotape.

$K^+$ selective microelectrodes were fabricated according to standard methods. Briefly, the reference barrel of a double-barreled pipette was filled with ACSF, and the other barrel was sylanized and the tip back-filled with KCl with $K^+$-selective resin (Corning 477317). Ion-selective microelectrodes were calibrated and considered suitable if they had a Nemstian slope response and remained stable throughout the duration of the experiment.

Exposure of hippocampal slices to low-$[Cl-]_o$ medium has been shown to include a temporally-dependent sequence of changes on the activity of CA1 pyramidal cells, with three characteristics phases, as described above. In brief, exposure to low-$[Cl-]_o$ medium results in a brief period of increased hyperexcitability and spontaneous epileptiform discharge. With further exposure to low-$[Cl^-]_o$ medium, spontaneous epileptiform activity is blocked, but cellular hyperexcitability remains, and action potential firing times become less synchronized with one another. Lastly, with prolonged exposure, the action potential firing times become sufficiently desynchronized so that stimulation-evoked field responses completely disappear, yet individual cells continue to show monosynapticlly-evoked responses to Schaffer collateral stimulation. The following results demonstrate that the antiepileptic effects of furosemide on chloride-cotransport antagonism are independent of direct actions on excitatory synaptic transmission, and are a consequence of a desynchronization of population activity with our any associated decrease in excitability.

In six hippocampal slices, $K^+$-selective and field microelectrodes were placed in the CA1 cell body layer, and a stimulating electrode was placed on the Schaffer collateral pathway, and single-pulse stimuli (300 μs) were delivered every 20 seconds. After stable baseline $[K^+]_o$ was observed for at least 20 minutes, the perfusion was switched to low-$[Cl^-]_o$ medium. Within 1-2 minutes of exposure to low-$[Cl^-]_o$ medium, the field responses became hyperexcitable as the $[K^+]_o$ began to rise. After approximately 4-5 minutes of exposure to low-$[Cl^-]_o$ medium, the magnitude of the field response diminished until it was completely abolished. The corresponding recording of $[K^+]_o$ showed that potassium began to rise immediately after exposure to low-$[Cl^-]_o$ medium, and that the peak of this $[K^+]_o$ rise corresponded in time to the maximally hyperexcitable CA1 field response. Coincident with the reduction of the magnitude of the field response, the $[K^+]_o$ began to diminish until after 8-10 minutes exposure to low-$[Cl^-]_o$ medium, it became constant for the remainder of the experiment at 1.8-2.5 mM above control levels. Four slices were switched back to control medium and allowed to fully recover. The experiment was then repeated with the $K^+$-selective microelectrode placed in the stratum radiatum. A similar sequence of changes in $[K^+]_o$ was observed in the dendritic layer, with the values of $[K^+]_o$ being 0.2-0.3 mM less than those observed in the cell body layers.

In four hippocampal slices, the responses of stimulation-evoked changes in $[K^+]_o$ between control conditions and after the CA1 field response was completely abolished by low-$[Cl^-]_o$ exposure were compared. In each slice, the $[K^+]_o$-selective measurements were acquired first in the cell body layer, and then after allowance for complete recovery in control medium, the experiment was repeated with the $K^+$-selective electrode moved to the stratum radiatum. Each stimulation trial consisted of a 10 Hz volley delivered to the Schaffer collateral for 5 seconds. The peak rises in $[K^+]_o$ were similar between control conditions an after prolonged exposure to low-$[Cl^-]_o$ medium, and between the cell body and dendritic layers. However, the recovery times observed after prolonged exposure to low-$[Cl^-]_o$ were significantly longer than those observed during control conditions.

These results demonstrate that the administration of furosemide resulted in increased $[K^+]_o$ in the extracellular spaces. Exposure of the brain tissue to low-$[Cl^-]_o$ medium immediately induced a rise in $[K^+]_o$ by 1-2 mM, which remained throughout the duration of exposure, and was coincident with the initial increase in excitability and the eventual abolishment of the CA1 field response. This loss of CA1 field response during low-$[Cl^-]_o$ exposure is most likely due to the desynchronization of neuronal firing times. Significantly, the stimulation-evoked increases in $[K^+]_o$, in both the cell body and dendritic layers were nearly identical before and after the complete low-$[Cl^-]_o$ blockade of the CA1 field response. This data suggests that comparable stimulation-evoked synaptic drive and action potential generation occurred under control conditions and after low $[Cl^-]_o$ blockade of the field. Together these data demonstrate that the antiepileptic and desynchronizing effects of the chloride-cotransport antagonist, furosemide, are independent of direct actions on excitatory synaptic transmission and are a consequence of a desynchronization of population activity without decrease in excitability.

Example 81

Changes in Extracellular pH During Low-Chloride Exposure

Antagonists of the anion/chloride-dependent cotransporter, such as furosemide and low-$[Cl-]_o$, may affect extracellular pH transients that might contribute to the maintenance of synchronized population activity. Rat hippocampal brain slices were prepared as described in Example 80, except the $NaHCO_3$ was substituted by equimolar amount of HEPES (26 nM) and an interface-type chamber was used.

In four hippocampal brain slices continuous spontaneous bursting was elicited by exposure to medium containing 100 μM 4-AP, as described in Example 13. Field recordings were acquired simultaneously from the cell body layers in areas CA1 and CA3. A stimulus delivered every 30 seconds to the Schaffer collaterals throughout the duration of the experiments. After at least 20 minutes of continuous bursting was observed, the slices were exposed to nominally bicarbonate free, 4-AP-containing HEPES medium. There were no significant changes observed in the spontaneous or stimulation-evoked field responses resulting from prolonged exposure (0.2 hours) to HEPES medium. After the slices had been exposed for at least 2 hours to the HEPES medium, the perfusion was switched to 4-AP-containing HEPES medium in which the $[Cl^-]_o$ had been reduced to 21 mM. Exposure to the low-$[Cl^-]_o$ HEPES medium induced the identical sequences of events, and at the same time course, as had previously been observed with low-$[Cl^-]_o$ $NaHCO_3$-containing medium. After complete blockade of spontaneous bursting, the perfusion medium was switched back to HEPES medium with normal $[Cl^-]_o$. Within 20-40 minutes, spontaneous bursting resumed. At the time the spontaneous bursting had resumed, the slices had been perfused with nominally bicarbonate-free HEPES medium for greater than 3 hours.

This data suggests that the actions of chloride-cotransport antagonism on synchronization and excitability are independent of affects on the dynamics of extracellular pH.

Figure 4A:
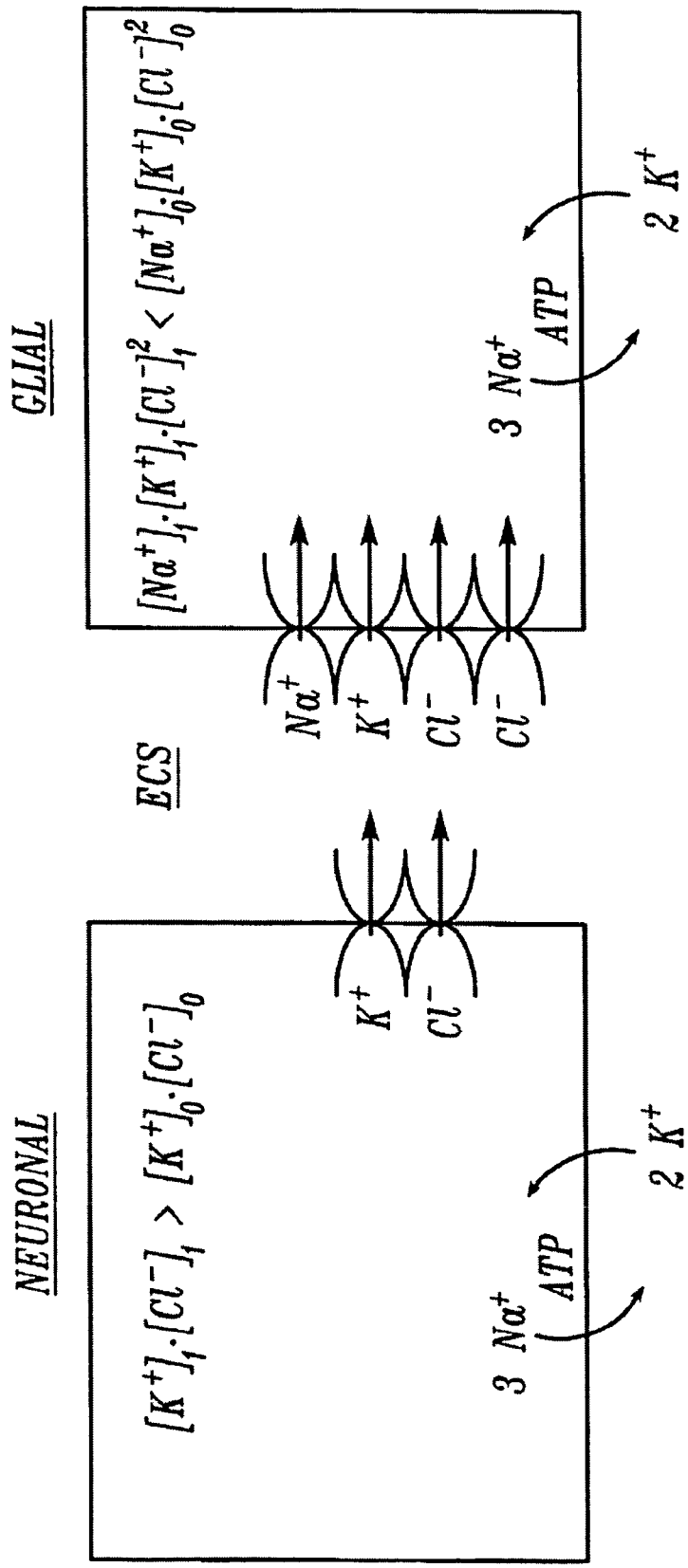
FIGS. 4A and 4B show a schematic diagram of ion co-transport under conditions of reduced chloride concentration.

FIG. 4 illustrates a schematic model of ion cotransport under conditions of reduced $[Cl^-]$. FIG. 4A, left panel, shows that the chloride gradient necessary for the generation of IPSPs in neurons is maintained by efflux of ions through a furosemide-sensitive $K^+$, $Cl^-$ cotransporter. Under normal conditions, a high concentration of intracellular potassium (maintained by the $3Na^+$, $2K^+$-ATPase pump) serves as the driving force for the extrusion of $Cl^-$ against its concentration gradient. In glial cells, as shown in the right panel of FIG. 4A, the movement of ions through the furosemide-sensitive NKCC co-transporter is from extracellular to intracellular spaces. The ion-gradients necessary for this cotransport are maintained, in part, by the "transmembrane sodium cycle": sodium ions taken into glial cells through NKCC cotransport are continuously extruded by the $3Na^+,2K^+$,-ATPase pump so that a low intracellular sodium concentration is maintained. The rate and direction of ion-flux through the furosemide-dependent cotransporters are functionally proportional to their ion-product differences written as $[K^+]_i \times [Cl^-]_i — [K^+]_o \times [Cl^-]_o$) for neuronal $K^+$, $Cl^-$ cotransport and as $[Na^+]_i \times [K^+]_i \times [Cl^-]^2_i — [Na^+]_o \times [K^+]_o \times [Cl^-]^2_o$) for glial NKCC cotransport. The sign of these ion-product differences show the direction of ion transport with positive being from intracellular to extracellular spaces.

Figure 4B:
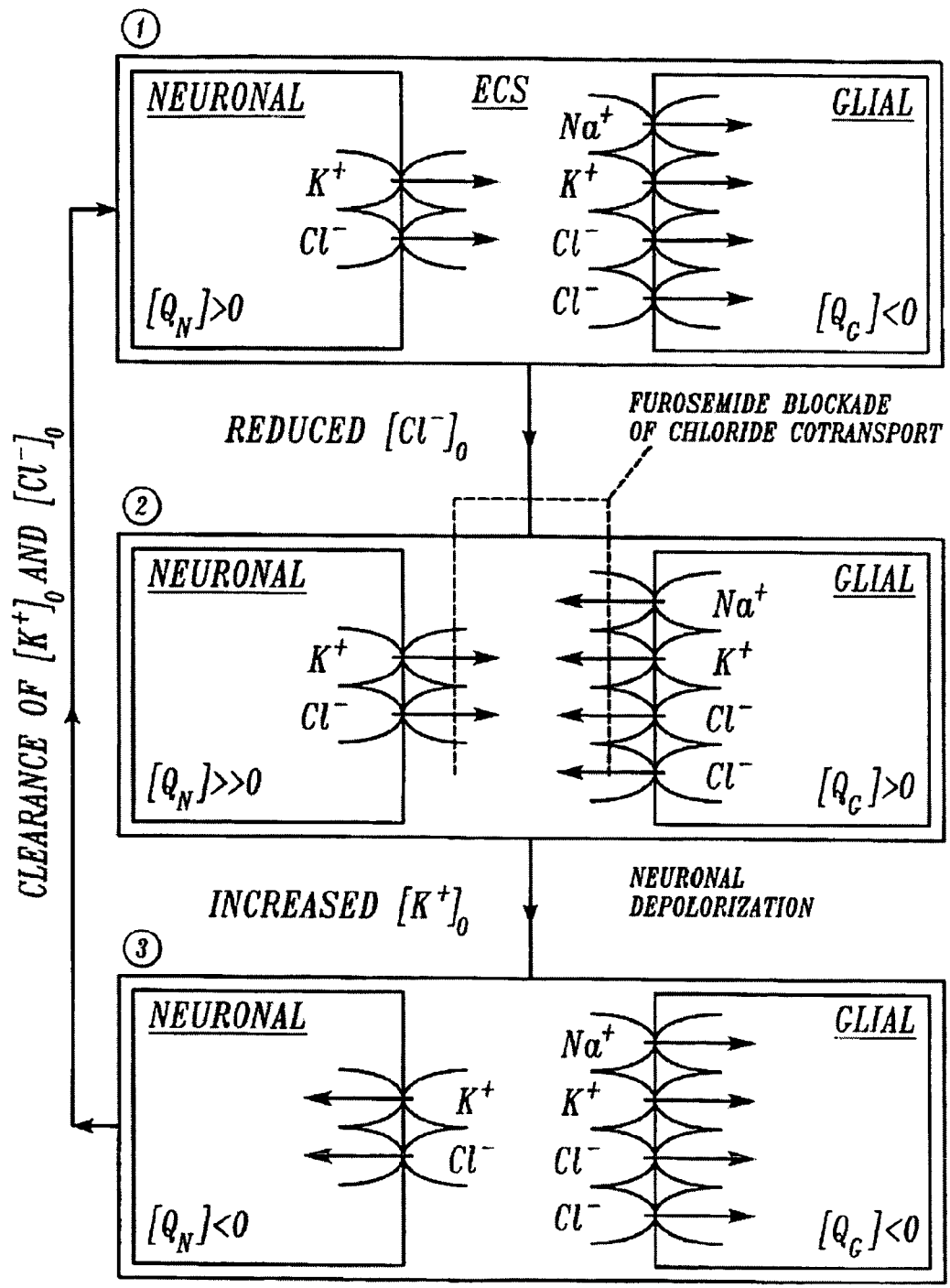

FIG. 4B shows a schematic phenomenological model that explains the emergence of the late-occurring spontaneous field events that arise as a result of prolonged low $—[Cl^-]_o$ exposure. We denote the ion-product differences for neurons and glia as $Q_N$ and $Q_G$, respectively. Under control conditions (1), the differences of the ion-products for neurons are such that $K^+$ and $Cl^-$ are cotransported from intracellular to extracellular spaces ($Q_N>0$); the differences in ion-products for glial cells are such that $Na^+$, $K^+$ and $Cl^-$ are cotransported from the ECS to intracellular compartments ($Q_G<0$). When $[Cl^-]_o$ is reduced (2), the ion-product differences are altered so that neuronal efflux of KCl is increased; however, the glial icon cotransport is reversed ($Q_G>0$), so that there is a net efflux of KCl and NaCl from intracellular to extracellular spaces. These changes result in buildup of extracellular potassium over time. Eventually, $[K^+]_o$ reaches a level that induces the depolarization of neuronal populations, resulting in an even larger accumulation of $[K_+]_o$. This large accumulation of extracellular ions then serves to reverse the ion-product differences so that KCl is moved from extracellular to intracellular spaces ($Q_N<0$, $Q_G<0$) (3). Further clearance of the extracellular potassium eventually resets the transmembrane ion gradients to initial conditions. By cycling through this process, repetitive negative field events are generated.

Example 82

Therapeutic Efficacy of Furosemide in the Alleviation of Pain Symptoms in an Animal Model of Neuropathic Pain The ability of furosemide to alleviate pain will be examined in rodents using the Chung model of neuropathic pain (see, for example, Walker et al. *Mol. Med. Today* 5:319-321, 1999). Sixteen adult male Long-Evans rats will be used in this study. All rats will receive spinal ligation of the L5 nerve as detailed below. Eight of the sixteen rats will receive an injection (intravenous) of furosemide and the remaining eight will receive intravenous injection of vehicle only. Pain threshold will be assessed immediately using the mechanical paw withdrawal test. Differences in pain thresholds between the two groups will be compared. If furosemide alleviates pain, the group with the furosemide treatment will exhibit a higher pain threshold than the group that received vehicle.

Chung Model of Neuropathy

Spinal nerve ligation is performed under isoflourane anesthesia with animals placed in the prone position to access the left L4-L6 spinal nerves. Under magnification, approximately one-third of the transverse process is removed. The L5 spinal nerve is identified and carefully dissected free from the adjacent L4 spinal nerve and then tightly ligated using a 6-0 silk suture. The wound is treated with an antiseptic solution, the muscle layer is sutured, and the incision is closed with wound clips. Behavioral testing of mechanical paw withdrawal threshold takes place within a 3-7 day period following the incision. Briefly, animals are placed within a Plexiglas chamber (20×10.5×40.5 cm) and allowed to habituate for 15 min. The chamber is positioned on top of a mesh screen so that mechanical stimuli can be administered to the plantar surface of both hindpaws. Mechanical threshold measurements for each hindpaw are obtained using an up/down method with eight von Frey monofilaments (5, 7, 13, 26, 43, 64, 106, and 202 mN). Each trial begins with a von Frey force of 13 mN delivered to the right hindpaw for approximately 1 sec, and then the left hindpaw. If there is no withdrawal response, the next higher force is delivered. If there is a response, the next lower force is delivered. This procedure is performed until no response is made at the highest force (202 mN) or until four stimuli are administered following the initial response. The 50% paw withdrawal threshold for each paw is calculated using the following formula: [Xth]log= [vFr]log+ky where [vFr] is the force of the last von Frey used, k=0.2268 which is the average interval (in log units) between the von Frey monofilaments, and y is a value that depends upon the pattern of withdrawal responses. If an animal does not respond to the highest von Frey hair (202 mN), then y=1.00 and the 50% mechanical paw withdrawal response for that paw is calculated to be 340.5 mN. Mechanical paw withdrawal threshold testing is performed three times and the 50% withdrawal values are averaged over the three trials to determine the mean mechanical paw withdrawal threshold for the right and left paw for each animal.

Example 83

Therapeutic Efficacy of Furosemide and Bumetanide in Alleviating the Symptoms of Intense Anxiety or Post Traumatic Stress Disorder The therapeutic usefulness of furosemide and bumetanide in the treatment of post traumatic stress disorder is examined by determining the ability of these compounds to alleviate intense anxiety in contextual fear conditioning in rats.

Contextual fear conditioning involves pairing an aversive event, in this case moderate foot shock, with a distinctive environment. The strength of the fear memory is assessed using freezing, a species-typical defensive reaction in rats, marked by complete immobility, except for breathing. If rats are placed into a distinctive environment and are immediately shocked they do not learn to fear the context. However, if they are allowed to explore the distinctive environment sometime before the immediate shock, they show intense anxiety and fear when placed back into the same environment. We can take advantage of this fact and, by procedurally dividing contextual fear conditioning into two phases, we can separately study effects of treatments on memory for the context (specifically a hippocampus based process) from learning the association between context and shock or experiencing the aversiveness of the shock (which depend upon emotional response circuitry including amygdala). Post traumatic stress syndrome (PTSD) in humans has been shown to be related to emotional response circuitry in the amygdala, and for this reason contextual memory conditioning is a widely accepted model for PTSD.

The experiment employed 24 rats. Each rat received a single 5 min episode of exploration of a small, novel environment. Seventy-two hours later they were placed into the same environment and immediately received two moderate footshocks (1 milliamp) separated by 53 sec. Twenty-four hours later, 8 of the rats received an injection (I.V.) of furosemide (100 mg/kg) in vehicle (DMSO), and 8 of the rats were injected I.V. with bumetanide (50 mg/kg) in vehicle (DMSO). The remaining 8 rats received an injection of DMSO alone. Each rat was again placed into the same environment for 8 min during which time freezing was measured, as an index of Pavlovian conditioned fear.

Four identical chambers (20×20×15 cm) were used. All aspects of the timing and control of events were under microcomputer control (MedPC, MedAssociates Inc., Vermont, USA). Measurement of freezing was accomplished through an overhead video camera connected to the microcomputer and was automatically scored using a specialty piece of software, FreezeFrame (OER Inc., Reston, Va.). Total freezing time was analyzed in a one-way analysis of variance (ANOVA) test, with drug dose as the within-groups factor.

Figure 5:
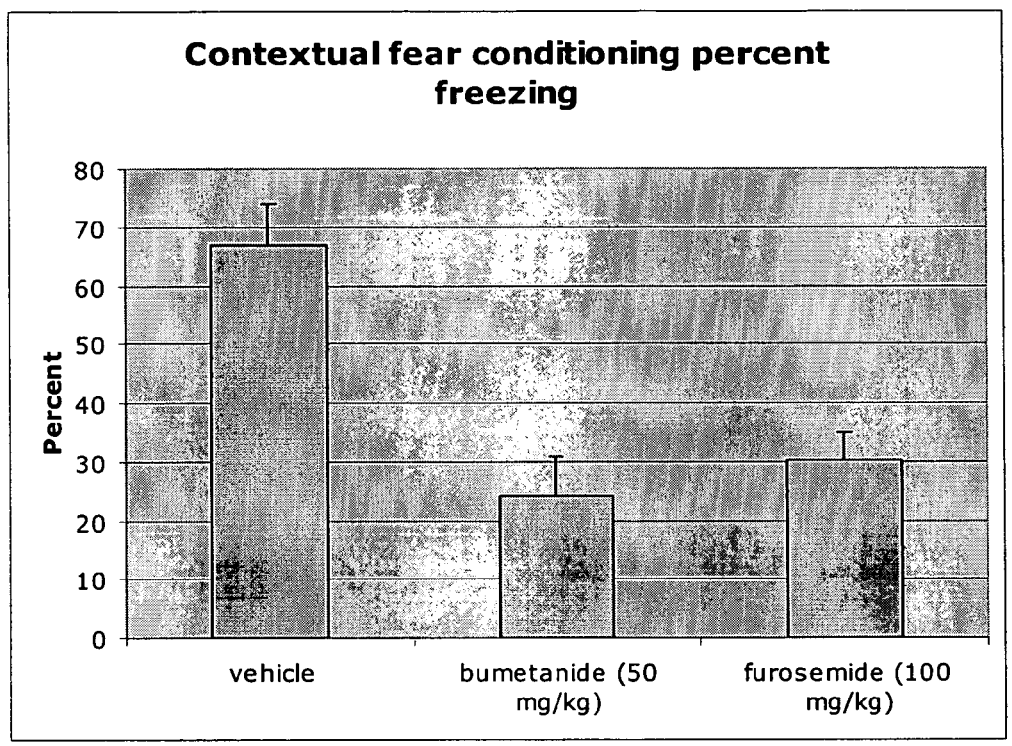
FIG. 5 shows that significantly less freezing was observed in animals treated with either bumetanide or furosemide than in animals receiving vehicle alone in a test of contextual fear conditioning in rats.

As shown in FIG. 5 significantly less freezing was observed in animals treated with either bumetanide or furosemide than in animals receiving vehicle alone, indicating that bumetanide and furosemide may be effectively employed in the treatment of post traumatic stress disorder.

Example 84

Therapeutic Efficacy of Furosemide and Bumetanide in Alleviating Anxiety

The therapeutic efficacy of furosemide and bumetanide in alleviating anxiety was examined by evaluating the effects of these compounds in fear potentiated startle (FPS) test in rats. This test is commonly used to distinguish anxiolytic drug effects from non-specific effects, such as sedation/muscle relaxation Twenty-four rats received a 30 min period of habituation to the FPS apparatus. Twenty-four hours later, baseline startle amplitudes were collected. The rats were then divided into three matched groups based on baseline startle amplitudes. One of the rats exhibited a significantly higher baseline startle than the others and was excluded from the experiments. Groups 1 and 2 therefore consisted of 8 rats each, with Group 3 consisting of 7 rats. Following baseline startle amplitude collection, 20 light/shock pairings were delivered on two sessions over two consecutive days (i.e., 10 light/shock pairings per day). On the final day (day 5), Groups 2 and 3 received an injection (i.v.) of either furosemide (100 mg/kg) or bumetanide (70 mg/kg) in vehicle (DMSO) and Group 1 received vehicle alone. Immediately following injections, startle amplitudes were assessed during startle alone trials and startle plus fear (light followed by startle) trials. Fear potentiated startle (light+startle amplitudes minus startle alone amplitudes) was compared between the treatment groups.

Animals were trained and tested in four identical stabilimeter devices (Med-Associates). Briefly, each rat was placed in a small Plexiglas cylinder. The floor of each stabilimeter consisted of four 6-mm-diameter stainless steel bars spaced 18 mm apart through which shock can be delivered. Cylinder movements result in displacement of an accelerometer where the resultant voltage is proportional to the velocity of the cage displacement. Startle amplitude is defined as the maximum accelerometer voltage that occurs during the first 0.25 sec after the startle stimulus is delivered. The analog output of the accelerometer was amplified, digitized on a scale of 0-4096 units and stored on a microcomputer. Each stabilimeter was enclosed in a ventilated, light-, and sound-attenuating box. All sound level measurements were made with a Precision Sound Level Meter. The noise of a ventilating fan attached to a sidewall of each wooden box produced an overall background noise level of 64 dB. The startle stimulus was a 50 ms burst of white noise (5 ms rise-decay time) generated by a white noise generator. The visual conditioned stimulus employed was illumination of a light bulb adjacent to the white noise source. The unconditioned stimulus was a 0.6 mA foot shock with duration of 0.5 sec, generated by four constant-current shockers located outside the chamber. The presentation and sequencing of all stimuli were under the control of the microcomputer.

FPS procedures consisted of 5 days of testing; during days 1 and 2 baseline startle responses were collected, days 3 and 4 light/shock pairings were delivered, day 5 testing for fear potentiated startle was conducted.

Matching: On the first two days all rats were placed in the Plexiglas cylinders and 3 min later presented with 30 startle stimuli at a 30 sec interstimulus interval. An intensity of 105 dB was used. The mean startle amplitude across the 30 startle stimuli on the second day was used to assign rats into treatment groups with similar means.

Training: On the following 2 days, rats were placed in the Plexiglas cylinders. Each day following 3 min after entry, 10 CS-shock pairings were delivered. The shock was delivered during the last 0.5 sec of the 3.7 sec CSs at an average intertrial interval of 4 min (range, 3-5 min).

Testing: Rats were placed in the same startle boxes where they were trained and after 3 min were presented with 18 startle-eliciting stimuli (all at 105 dB). These initial startle stimuli were used to again habituate the rats to the acoustic startle stimuli. Thirty seconds after the last of these stimuli, each animal received 60 startle stimuli with half of the stimuli presented alone (startle alone trials) and the other half presented 3.2 sec after the onset of the 3.7 sec CS (CS-startle trials). All startle stimuli are presented at a mean 30 sec interstimulus interval, randomly varying between 20 and 40 sec.

Measures: The treatment groups were compared on the difference in startle amplitude between CS-startle and startle-alone trials (fear potentiation).

Figure 6:
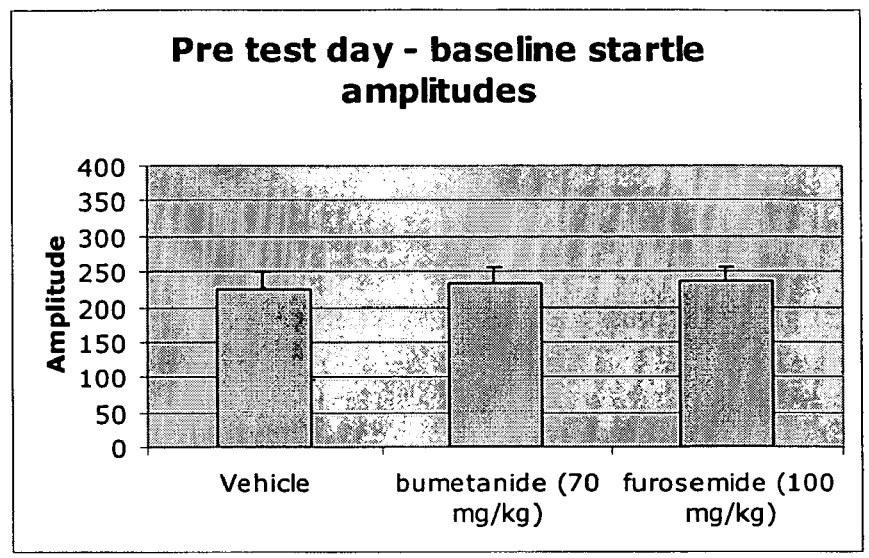
FIG. 6 shows baseline startle amplitudes in a fear potentiated startle test in rats
Figure 7:
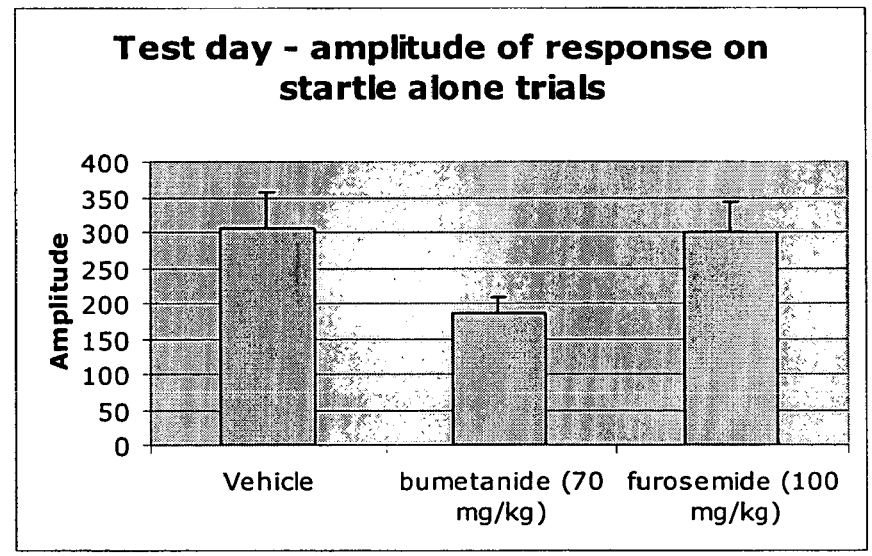
FIG. 7 shows the amplitude of response in rats on startle alone trials determined immediately following administration of either DMSO alone, bumetanide or furosemide.
Figure 8:
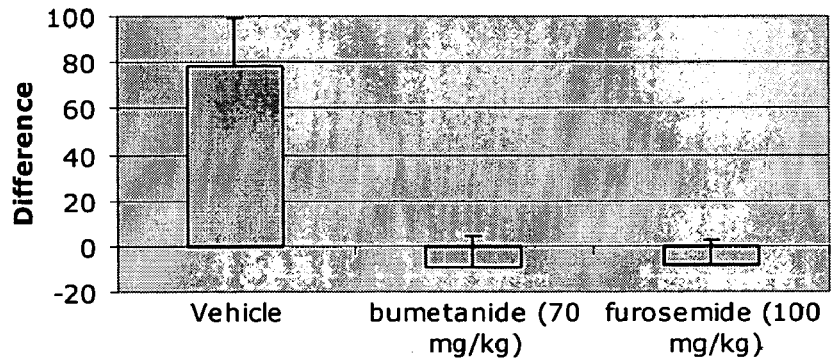
FIG. 8 shows the difference score (startle alone—fear potentiated startle) on the test day in rats treated with either DMSO, bumetanide or furosemide

FIG. 6 shows the baseline startle amplitudes for each group of rats determined prior to the test day. FIG. 7 shows the amplitude of response on startle alone trials determined on the test day immediately following injection of either DMSO alone, bumetanide or furosemide, with FIG. 8 showing the difference score (startle alone—fear potentiated startle) on the test day. As shown in the figures, a statistically significantly lower difference score was observed in rats treated with either furosemide or bumetanide than in rats treated with vehicle alone, indicating that both furosemide and bumetanide are effective in reducing anxiety.

Figure 9:
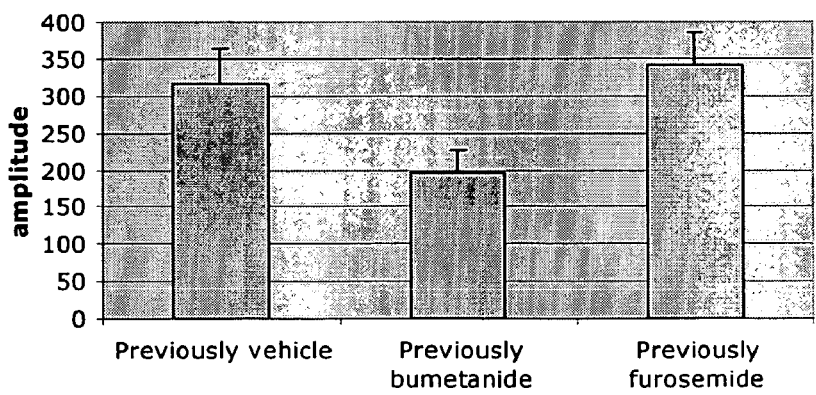
FIG. 9 shows the startle alone amplitude in rats one week after administration of either DMSO, bumetanide or furosemide.
Figure 10:
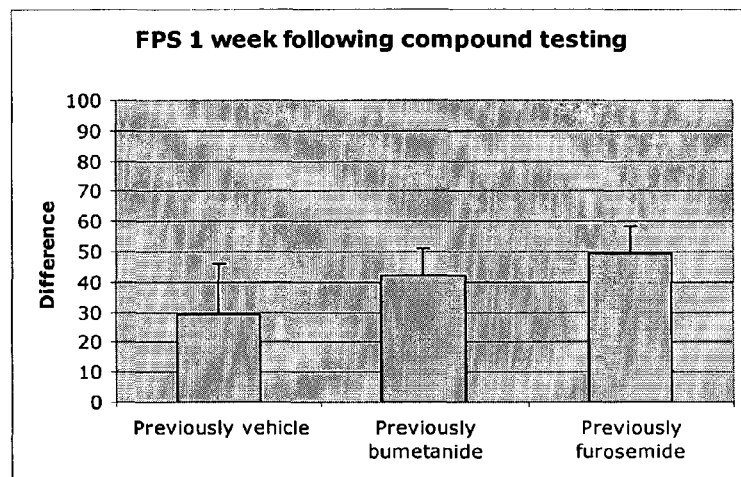
FIG. 10 shows the difference score in rats one week after administration of either DMSO, bumetanide or furosemide.

FIGS. 9 and 10 show the startle alone amplitude and the difference score, respectively, one week after treatment with either furosemide or bumetanide. Animals treated with either furosemide or bumetanide were found to have a higher difference score than animals treated with vehicle alone. However, as the error bars are so large for the vehicle-treated animals, the data does not imply any statistically significant difference between vehicle and bumetanide, with possibly a small difference between vehicle and furosemide.

Example 85

Therapeutic Efficacy of Bumetanide Analogs in Alleviating Anxiety

The therapeutic efficacy of several bumetanide analogs in alleviating anxiety was examined using the fear potentiated startle (FPS) test in rats as described above.

Figure 11:
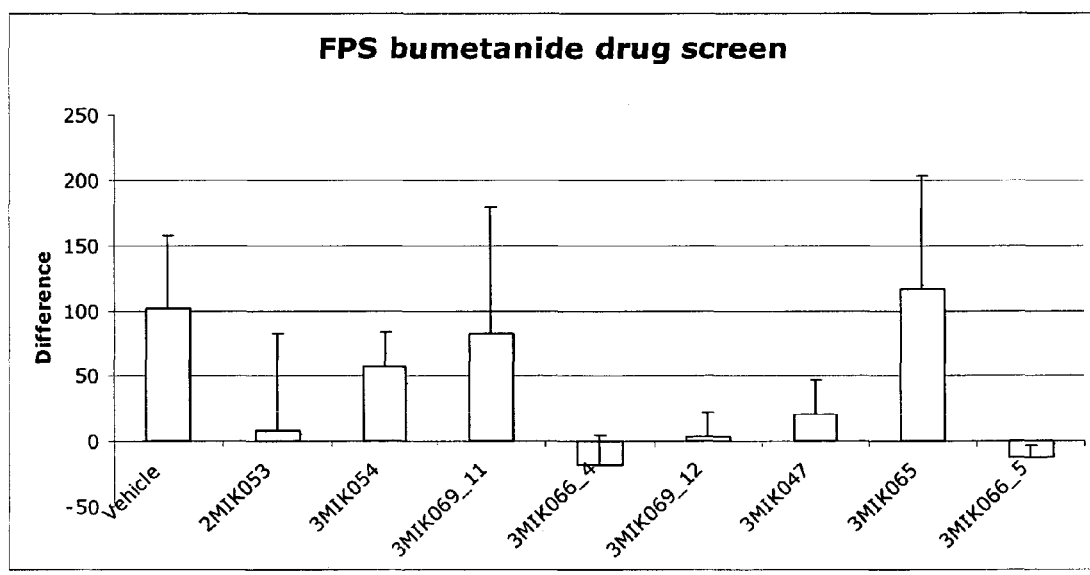
FIG. 11 shows the difference score (startle alone—fear potentiated startle) on the test day in rats treated with one of the following bumetanide analogs: bumetanide N,N-diethylglycolamide ester (referred to as 2MIK053); bumetanide methyl ester (referred to as 3MIK054); bumetanide N,N- dimethylglycolamide ester (referred to as 3MIK069-11); bumetanide morpholinodethyl ester (referred to as 3MIK066-4); bumetanide pivaxetil ester (referred to as 3MIK069-12); bumetanide cyanomethyl ester (referred to as 3MIK047); bumetanide dibenzylamide (referred to as 3MIK065); and bumetanide 3-(dimethylaminoproply) ester (referred to as 3MIK066-5). The vehicle was DMSO.

FIG. 11 shows the difference score (startle alone—fear potentiated startle) on the test day in rats treated with one of the following bumetanide analogs: bumetanide N,N-diethylglycolamide ester (referred to as 2MIK053); bumetanide methyl ester (referred to as 3MIK054); bumetanide N,N-dimethylglycolamide ester (referred to as 3MIK069-11); bumetanide morpholinodethyl ester (referred to as 3MIK066-4); bumetanide pivaxetil ester (referred to as 3MIK069-12); bumetanide cyanomethyl ester (referred to as 3MIK047); bumetanide dibenzylamide (referred to as 3MIK065); or bumetanide 3-(dimethylaminoproply) ester (referred to as 3MIK066-5). The vehicle was DMSO. As can be seen from FIG. 11, the difference score obtained after administration of most of the bumetanide analogs was significantly lower than that observed following administration of vehicle alone, demonstrating that these analogs may be effectively employed to reduce anxiety. In addition, several of the bumetanide analogs were observed to have significantly lower diuretic effects than those generally associated with either furosemide or bumetanide.

While the present invention has been described with reference to the specific embodiments thereof, it will be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All patents and publications cited herein and PCT Application WO 00/37616, published Jun. 29, 2000, are specifically incorporated by reference herein in their entireties.

SEQ ID NO: 1-2 are set out in the attached Sequence Listing. The codes for polynucleotide and polypeptide sequences used in the attached Sequence Listing conform to WIPO Standard ST.25 (1988), Appendix 2.

We claim:

1. A compound of formula I:

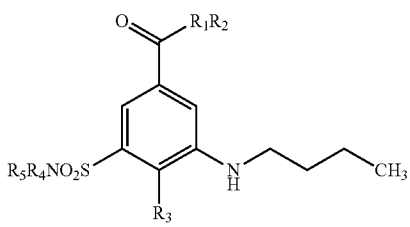

or a pharmaceutically acceptable salt or tautomer thereof, wherein $R_1$ is not present, or O;

when $R_1$ is O, $R_2$ is selected from the group consisting of: alkyloxycarbonylalkyl and alkylamide unsubstituted or substituted with alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, or ureido, and when $R_1$ is not present, $R_2$ is selected from the group consisting of dialkylamino and diarylalkylamino, unsubstituted or substituted with alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, or ureido;

$R_3$ is selected from the group consisting of aryl, halo, hydroxy, alkoxy, and aryloxy, unsubstituted or substituted with alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, or ureido; and $R_4$ and $R_5$ are each independently selected from the group consisting of hydrogen, alkylaminodialkyl, alkylhydroxyaminodialkyl, unsubstituted or substituted with alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, or ureido.

2. The compound of claim 1, selected from the group consisting of: bumetanide dibenzylamide and bumetanide diethylamide, or a pharmaceutically acceptable salt or tautomer thereof.

3. A pharmaceutical composition comprising a compound of claim 1, or a pharmaceutically acceptable salt or tautomer thereof, and a pharmaceutically acceptable carrier, excipient or diluent.

4. A pharmaceutical composition comprising a compound of claim 2, or a pharmaceutically acceptable salt or tautomer thereof, and a pharmaceutically acceptable carrier, excipient or diluent.

5. A compound which is bumetanide benzyl ester, bumetanide morpholinoethyl ester; bumetanide 3-(dimethylaminopropyl) ester; bumetanide N,N-diethylglycolamide ester; bumetanide dimethylglycolamide ester; bumetanide pivaxetil ester; bumetanide propaxetil ester, or pharmaceutically acceptable salts or tautomers thereof.

* * * * *